(12) United States Patent
Mercep et al.

(10) Patent No.: US 7,091,187 B2
(45) Date of Patent: *Aug. 15, 2006

(54) COMPOUNDS, COMPOSITIONS AND METHODS FOR TREATMENT OF INFLAMMATORY DISEASES AND CONDITIONS

(75) Inventors: Mladen Mercep, Zagreb (HR); Milan Mesic, Zagreb (HR); Linda Tomaskovic, Zagreb (HR); Stribor Markovic, Karlovac (HR); Oresta Makaruha, Zagreb (HR); Visnja Poljak, Zadar (HR)

(73) Assignee: Pliva-Istrazivacki Institut D.o.o., Zagreb (HR)

( * ) Notice: Subject to any disclaimer, the term of this patent is extended or adjusted under 35 U.S.C. 154(b) by 0 days.

This patent is subject to a terminal disclaimer.

(21) Appl. No.: 10/615,716

(22) Filed: Jul. 8, 2003

(65) Prior Publication Data

US 2004/0014685 A1 Jan. 22, 2004

Related U.S. Application Data

(60) Provisional application No. 60/394,670, filed on Jul. 8, 2002.

(51) Int. Cl.
*A61K 31/70* (2006.01)
*C07H 17/08* (2006.01)

(52) U.S. Cl. ............... 514/29; 514/26; 536/5; 536/7.4

(58) Field of Classification Search .......... 536/5, 536/7.4; 514/26, 29, 8; 530/322
See application file for complete search history.

(56) References Cited

U.S. PATENT DOCUMENTS

| | | | |
|---|---|---|---|
| 4,474,768 A | 10/1984 | Bright | |
| 4,710,495 A | 12/1987 | Bodor | |
| 5,747,467 A | 5/1998 | Agouridas et al. | |
| 6,228,346 B1 | 5/2001 | Zhang et al. | |
| 6,273,086 B1 | 8/2001 | Ohki et al. | |
| 6,297,260 B1 | 10/2001 | Bandarage et al. | |
| 6,402,733 B1 | 6/2002 | Daugherty | |
| 2001/0006962 A1 | 7/2001 | Myhren et al. | |
| 2004/0005641 A1 | 1/2004 | Burnet et al. | |
| 2004/0033969 A1 | 2/2004 | Burnet et al. | |
| 2004/0087517 A1 | 5/2004 | Burnet et al. | |
| 2004/0186063 A1 | 9/2004 | Gutke et al. | |

FOREIGN PATENT DOCUMENTS

| EP | 0283055 | 8/1990 |
|---|---|---|
| EP | 0771564 | 5/1997 |
| EP | 0775489 | 5/1997 |
| EP | 0 283 055 | 9/1998 |
| EP | 00680967 | 10/1998 |
| EP | 0 895 999 | 2/1999 |
| EP | 0984019 A1 | 3/2000 |
| EP | 0984019 | 3/2000 |
| GB | 2 327 084 | 1/1999 |
| WO | WO 94/13690 | 6/1992 |
| WO | WO 92/13872 | 8/1992 |
| WO | WO 92/13873 | 8/1992 |
| WO | WO 94/14834 | 7/1994 |
| WO | WO-97/41255 | 11/1997 |
| WO | WO 98/56801 | 12/1998 |
| WO | WO 99/51616 | 10/1999 |
| WO | WO-99/64040 | 12/1999 |
| WO | WO 00/42055 | 7/2000 |
| WO | WO-00/64882 | 11/2000 |
| WO | WO-02/055531 | 7/2002 |
| WO | WO-03/070173 A2 | 8/2003 |
| WO | WO-03/070174 A2 | 8/2003 |
| WO | WO-03/070254 | 8/2003 |

OTHER PUBLICATIONS

Burnet et al., "Conjugates of biologically active compounds, methods for their preparation and use, formulation, and pharmaceutical applications thereof," U.S. Provisional Appl. No. 60/357,789, filed Feb. 15, 2002.

Brandt–Rauf et al., "Fluorescent Assay For Estimating the Binding of Erythromycin Derivatives to Ribosomes," Antimicrobiol Agents and Chemotherapy, American Society for Microbiology, Washington, D.C., 14(1):88–94, (1978).

Gladue R. P. et al.,"In Vitro and In Vivo Uptake of Azithromycin (CP–62,993) by Phagocytic Cells: Possible Mechanism of Delivery and Release at Sites of Infection," *Antimicrob. Agents and Chemother.*, 33. 1989, 277–282.

(Continued)

*Primary Examiner*—Elli Peselev
(74) *Attorney, Agent, or Firm*—Darby & Darby

(57) ABSTRACT

The present invention relates (a) to new compounds represented by Formula I:

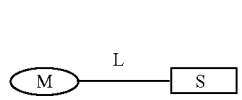

wherein M represents a macrolide subunit (macrolide moiety) derived from macrolide possessing the property of accumulation in inflammatory cells, S represents a steroid subunit (steroid moiety) derived from steroid drug with anti-inflammatory activity and L represents a linker molecule linking M and S, (b) to their pharmacologically acceptable salts, prodrugs and solvates, (c) to processes and intermediates for their preparation, and (d) to their use in the treatment of inflammatory diseases and conditions in humans and animals. Such compounds inhibit many cytokines and immune mediators involved in immune responses which cause inflammation, allergy, or alloimmunity, including without limitation IL-1, 2, 4, 5, 6, 10, 12, GMCSF, ICAM, and TNF-α. Importantly, anti-inflammatory steroids exert a direct anti-inflammatory effect through binding to the glucocorticosteroid receptor.

60 Claims, 4 Drawing Sheets

OTHER PUBLICATIONS

Olsen K. M. et al., "Intrapulmonary Pharmacokinetics of Zithromycin in Healthy Volunteers Given Five Oral Doses," *Antimicrob. Agents and Chemother.*, 40, 1996, 2582–2585.

Mikasa, K. et al., "The anti–inflammatory effect of erythromycin in zymosan–induced peritonitis of mice,"*J. Antimicrob. Chemother.*, 30, 1992, 339–348.

"Discussion, Genomic organization of axolotl 1g genes," *J. Immunol.*, 159, 1997, 3395–4005.

Takizawa, H. et al., "Erythromycin Modulates IL–8 Expression in Normal and Inflamed Human Bronchial Epithelial Cells," *Am. J. Respir. Crit. Care Med.*, 156, 1997, 266–271.

Labro, M.T., "Anti–inflammatory activity of macrolides: a new therapeutic potential?" *J. Antimicrob. Chemother.*, 41, 1998, 37–46.

Cazzola, M., et al., "Potential role of macrolides in the treatment of asthma," *Mondaldi Arch. Chest Dis.*, 55, 2000, 231–236.

Avila, P.C. et al., "Macrolides, asthma, inflammation, and infection," *Ann. Allergy Asthma Immunol*, 84, 2000, 565–568.

Amayasu, H. et al., "Clarithromycin suppresses bronchial hyperresponsisveness associated with eosinophilic inflammation in patients with asthma," *Ann. Allergy, Asthma & Immunol*, 84, 2000, 594–598.

Shoji, T. et al., "Anti–inflammatory effect of roxithromycin in patients with aspirin–intolerant asthma," *Clin. Exp. Allergy*, 29, 999, 950–956.

Griffith, E.C., et al., "Yeast Three–Hybrid System for Detecting Ligand–Receptor Interactions," *Methods in Enzymology*, 328m 2000, 89–110.

Denis A. et al., "Synthesis and Antibacterial Activity of HMR 36K47, A New Ketolide Highly Potent Against Erythromycin–Resistant and Susceptible Pathogens," *Bioorg. & Med. Chem. Lett*, 9, 1999, 3075–3080.

Agouridas C. et al., "Synthesis and Antibacterial Activity of Ketolides (6–O–Methyl–3–oxoerythromycin Derivatives): A New Class of Antibacterials Highly Potent against Macrolide–Resistant and –Susceptible Respiratory Pathogens," *J. Med. Chem.*, 41, 1998, 4080–4100.

Sun, Or Y. et al. *J. Med. Chem.* 2000, 43, 1045–1049.

McFarland, J. W. et al., "Repromicin Derivatives with Potent Antibacterial Activity against *Pasteurella multocida*," *J. Med. Chem.*, 50, 1997, 1041–1045.

Denis A. et al., Synthesis of 6–O–Methyl–Azithromycin and Its Ketolide Analogue via Beckmann Rearrangement of 9(E)–6–O–Methyl–Erythromycin Oxime, *Bioorg.& Med. Chem. Lett.*, 8, 1998, 2427–2432.

Lartey et al., Synthesis of 4"–Deoxy Motilides: Identification of a Potent and Orally Active Prokinetic Drug Candidate, *J. Med. Chem.*, 38, 1998, 1793–1798.

Kirst, H.A. et al., "34. Metabolism of macrolides," Bryskier, A. J. et al., Ed. *Macrolides, Chemistry, Pharmacology and Clinical Use*; Bryskier, Arnette Blackwell: Paris, 1993; pp 485–491.

Ma, Z. et al., "Discovery and Development of Ketolides as a New Generation of Macrolide Antimicrobial Agents," *Current Medicinal Chemistry—Anti–Infective Agents*, 1, 2002, 15–34.

Pascual A. et al., "Uptake and intracellular activity of ketolide HMR 3647 in human phagocytic and non–phagocytic cells," *Clin. Microbiol. Infect.*, 7, 2001, 65–69.

Hand, W. L. et al., "Characteristics and mechanisms of azithromycin accumulation and efflux in human polymorphonuclear leukocytes," *Int. J. Antimicrob. Agents*, 18, 2001, 419–425.

Amsden, G. W., "Advanced–generation macrolides: tissue–directed antibiotics," *Int. J. Antimicrob. Agents*, 18, 2001, 11–15.

Johnson, J. D. et al., "Antibiotic uptake by alveolar macrophages," *J. Lab. Clin. Med.*, 95, 1980, 429–439.

Wildfeuer, A. et al., "Uptake of Azithromycin by Various Cells and its Intracellular Activity under In Vivo Conditions," *Antimicrob. Agents Chemother.*, 40, 1996, 75–79.

Scorneaux, B. et al., "Intracellular Accumulation, Subcellular Distribution, and Efflux of Tilmicosin in Chicken Phagocytes," *Poult. Sci.*, 77, 1998, 1510–1521.

Mtairag, E. M. et al., "Investigation of dirithromycin and erythromycylamine uptake by human neutrophils in vitro," *J. Antimicrob. Chemother.* 33, 1994, 523–536.

Anderson R. et al., "An in–vitro evaluation of the cellular uptake and intraphagocytic bioactivity of clarithromycin (A–56268, TE–031), a new macrolide antimicrobial agent," *J. Antimicrob. Chemother.*, 22, 1988, 923–933.

Tasaka, Y. et al., "Rokitamycin Uptake by Alveolar Macrophages," *Jpn. J. Antibiot.* 41, 1988, 836–840.

Harf, R. et al., "Spiramycin uptake by alveolar macrophages," *J. Antimicrob. Chemother.*, 22, 1988, 135–140.

Suzuki, T. et al., "General and facile method for determination of configuration of steroid–17–yl–methyl glycolates at C–20 based on kinetic examination," *Chem. Soc.*, Perkin Trans. 1, 1998, 3831–3836.

McLean, H.M. et al., "Novel Fluorinated Antiinflammatory Steroid with Reduced Side Effects: Methyl 9α–Fluoroprednisolone–16–carboxylate," *J. Pharm. Sci.* 1994, 83, 476–480.

Little, R.J. et al., "Soft Drugs Based on Hydrocortisone: The Inactive Metabolite Approach and Its Application to Steroidal Antiinflammatory Agents," *Pharm. Res.*, 16, 1999, 961–967.

Kertesz, D.J. et al., "Thiol Esters from Steroid 17β–Carboxylic Acids: Carboxylate Activation and Internal Participation by 17α–Acylates," *J. Org. Chem.*, 51, 1986, 2315–2328.

Phillipps, G. et al., "Synthesis and Structure—Activity Relationships in a Series of Antiinflammatory Corticosteroid Analogues, Halomethyl Androstane–17β–carbothioates and 17β–carboselenoates," *J. Med. Chem.* 37, 1994, 3717–3729.

Bright, G.M. et al., "Synthesis, In Vitro and In Vivo Activity of Novel 9–Deoxo–9a–AZA–9a–Homoerythromycin A Derivatives; A new Class of Macrolide Antibiotics, the Azalides" *J. Antibiot.*, 41, 1998, 1029–1047.

Costa, A.M. et al., "Hybrids of macrolides and nucleobases or nucleosides," *Tetrahedron Letters*, 41, 2000, 3371–3375.

Newman, S.P. et al., "Evaluation of jet nebulisers for use with gentamicin solution," *Thorax*, 40, 1985, 671–676.

Berenberg, M.J. et al., "Comparison of Metered–Dose Inhaler Attached to an Aerochamber with an Updraft Nebulizer for the Administration of Metaproterenol in Hospitalized Patients," *J. Asthma USA*, 22, 1985, 87–92.

Figure 1: Inhibition of Hybridoma 13 Proliferation
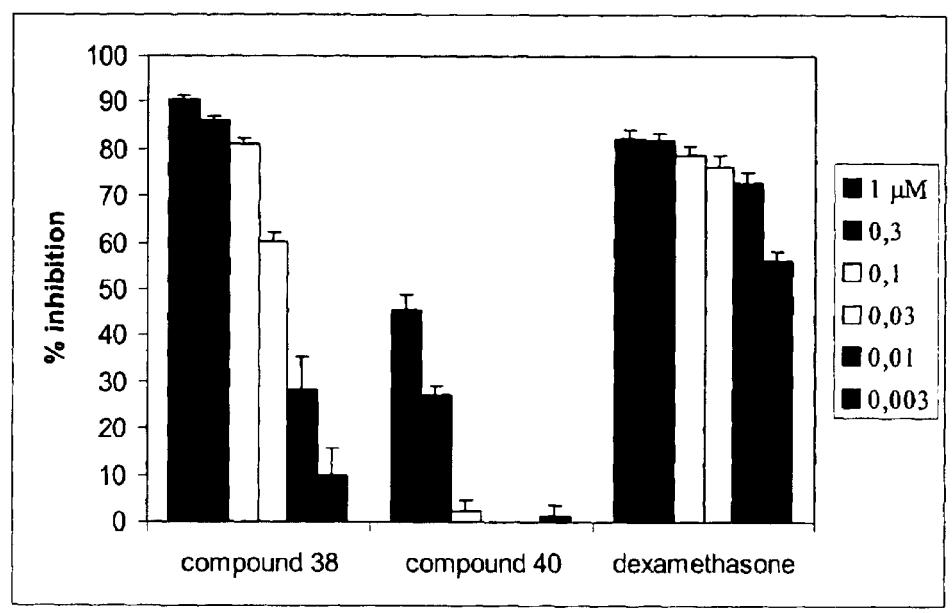
Inhibition of concanavalin A stimulated interleukin-4 and interleukin-5 production in splenocytes Figure 2: Inhibition of ConA stimulated production of interleukin 4 in murine splenocytes.
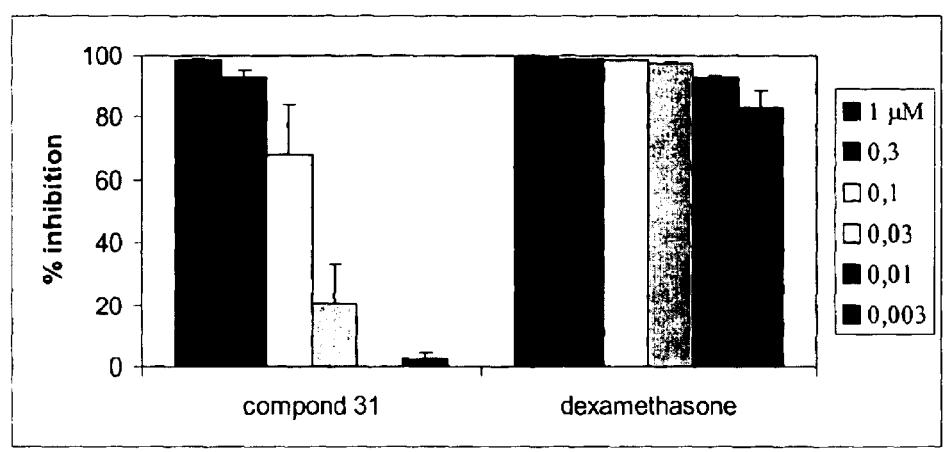

Figure 3: Inhbition of ConA stimulated production of interleukin 5 in murine splenocytes
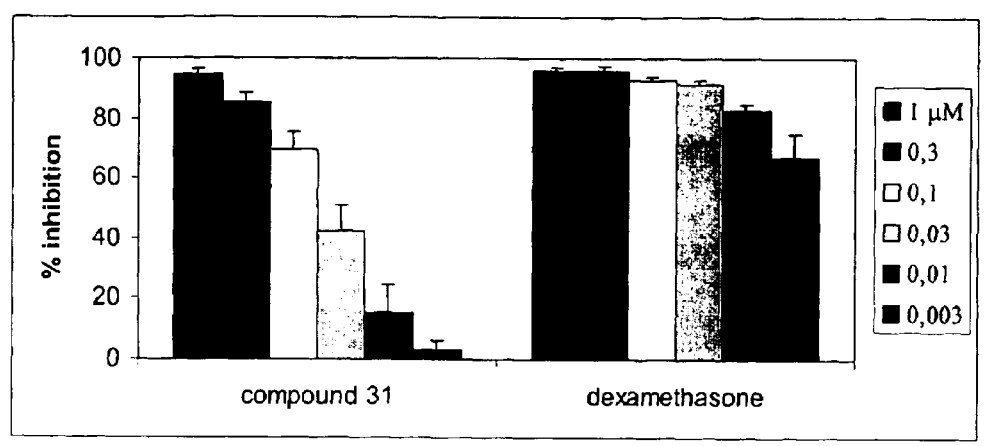

Figure 4: Reduction of eosinophil number in murine model of lung eosinophilia
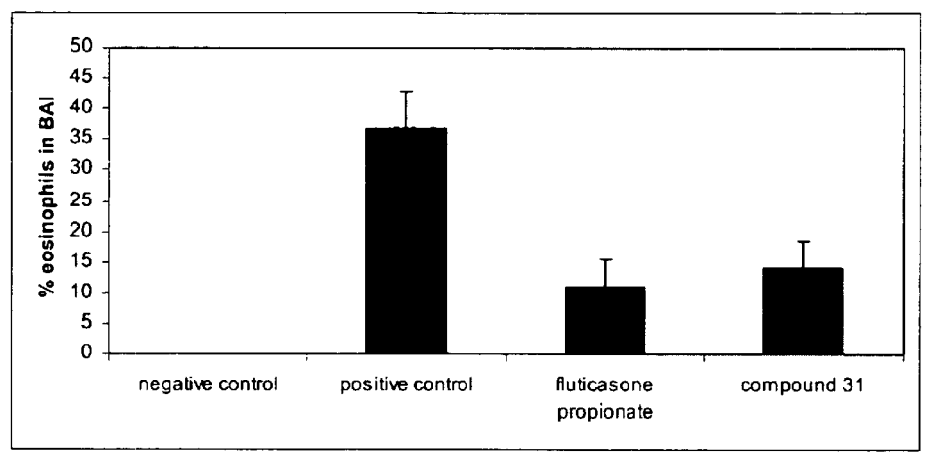

COMPOUNDS, COMPOSITIONS AND METHODS FOR TREATMENT OF INFLAMMATORY DISEASES AND CONDITIONS

PRIORITY CLAIM

This application claims priority to U.S. Provisional Application No. 60/394,670 filed Jul. 8, 2002, herein incorporated by reference in its entirety

BACKGROUND OF THE INVENTION

The present invention relates (a) to new compounds represented by the structure I:

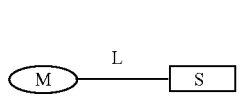

wherein M represents a macrolide subunit possessing the property of accumulation in inflammatory cells, S represents an anti-inflammatory steroid subunit, and L represents a linker molecule linking M and S, (b) to their pharmacologically acceptable salts, prodrugs and solvates, (c) to processes and intermediates for their preparation, and (d) to their use in the treatment of inflammatory diseases and conditions in humans and animals. Such compounds inhibit many cytokines and immune mediators involved in immune responses which cause inflammation, allergy, or alloimmunity, including without limitation IL-1, 2, 4, 5, 6, 10, 12, GMCSF, ICAM, and TNF-α. Importantly, anti-inflammatory steroids exert a direct anti-inflammatory effect through binding to the glucocorticoid receptor.

SUMMARY OF THE INVENTION

Anti-inflammatory medicaments could be classified into those of steroid and of nonsteroidal type. Steroid anti-inflammatory compounds are still the most effective ones in the treatment of inflammatory diseases and conditions such as: asthma, chronic obstructive pulmonary disease, inflammatory nasal diseases such as allergic rhinitis, nasal polyps, intestinal diseases such as Crohn's disease, colitis, ulcerative colitis, dermatological inflammations such as eczema, psoriasis, allergic dermatitis, neurodermatitis, pruritus, conjunctivitis, autoimmune diseases such as rheumatoid arthritis, and inhibition of transplantation immunity. Moreover, steroids are used as adjunct chemotherapeutic agents in treating various malignancies, including leukemias, lymphomas, myelomas, and other malignancies of the hematopoietic system. In addition to excellent potency and effectiveness, medicaments of this type also possess numerous unfavourable side-effects, e.g., on carbohydrate metabolism, calcium resorption, secretion of endogenous corticosteroids as well as on the physiological functions of the pituitary gland, adrenal cortex and thymus. Recently developed steroids are highly effective against inflammatory conditions and processes since they inhibit many inflammation mediators, whereas their systemic side-effects are diminished. Patent applications WO 94/13690, WO 94/14834, WO 92/13873 and WO 92/13872 describe the so-called "soft" steroids or hydrolysable corticosteroids designed for topical application on the inflammation site, whereas their systemic side-effects are diminished due to instability of "soft" steroids in the serum, wherein the active steroid very rapidly hydrolyses into the inactive form. An ideal steroid, however, without unfavourable effects in a long-term and continuous treatment as required for the control of diseases such as asthma or Crohn's disease has yet to be found. Thus there is an acute need for steroids with an improved therapeutic profile, and/or fewer or milder side effects.

Macrolides such as macrolide antibiotics accumulate preferentially within different cells of subjects administered such molecules, especially within phagocyte cells such as mononuclear peripheral blood cells, peritoneal and alveolar macrophages as well as in the liquid surrounding the bronchoalveolar epithelium (Glaude R. P. et al., *Antimicrob. Agents Chemother.*, 33 1989, 277–282; Olsen K. M. et al., *Antimicrob. Agents Chemother.*, 40 1996, 2582–2585). Moreover, relatively weak inflammatory effects of some macrolides have been described. For example, the anti-inflammatory effect of erythromycin derivatives (*J. Antimicrob. Chemother.*, 41 1998 37–46; WO 00/42055) and azithromycin derivatives has recently been described (EP 0283055). Anti-inflammatory effects of some macrolides are also known from in vitro and in vivo studies in experimental animal models such as zimosane-induced peritonitis in mice (*J. Antimicrob. Chemother.*, 30 1992 339–348) and endotoxin-induced neutrophil accumulation in rat trachea (J. Immunol. 159 1997 3395–4005). The modulating effect of macrolides upon cytokines such as interleukin 8 (IL-8) (*Am. J. Respir. Crit. Care Med.* 156 1997 266–271) or interleukin 5 (IL-5) (EP 0775489 and EP 0771564) is known as well.

Macrolides have been found useful in the treatment of asthma, either because of their antimicobial activity, or through a steroid-sparing effect. However, other properties such as eosinophil or neutrophil activation inhibition, have been suggested to explain the reduction in airway hyerresponsiveness. Respiratory and other inflammatory diseases (e.g. skin diseases or sinusitis) may also benefit from macrolide therapy (Labro M. T. *J. Antimicrob. Chemother.* 1998, 41,37; Cazzola m et al., *Mondaldi Arch Chest Dis* 200,55, 231; Avila P. C. et al., *Ann Allergy Asthma Immunol* 200, 84 565; Amayasu H. Et al., *Ann Allergy Asthma Immunol* 2000, 84, 594; and Shoji T. Et al., *Clin Exp Allergy* 1999,29, 950; encorporated by reference in their entirety). U.S. Provisional Application No. 60/394,671 (filed Jul. 8, 2002) and No. 60/395,190 (filed Jul. 8, 2002), herein incorporated by reference in their entirety, describe macrolide linker complexes that have accumulating properties.

BRIEF DESCRIPTION OF THE FIGURES

FIG. 1 represents efficacy of compound 38 and 40 in inducing hybridoma 13 apoptosis, as compared to standard dexamethasone.

FIGS. 2 and 3 represent inhibition of interleukin 4 and 5 respectively, by compound 31, as compared to standard dexamethasone.

FIG. 4 represents reduction in eosinophil percentage in BALF by compound 31, as compared with standard fluticasone propionate. Compound 31 was given i.n. in dose of 2 mg/kg, while fluticasone propionate was given 1 mg/kg.

DETAILED DESCRIPTION OF THE INVENTION

Compounds represented by Formula I differ from steroids that are either unconjugated or conjugated to other types of molecules in that they combine the anti-inflammatory and immuno suppressant properties of steroids with the accumulation property of macrolides which are known to accumulate in cells effecting the inflammatory immune response that needs to be subdued. Such action of the compounds of Formula I arises from the macrolide moiety M which has the pharmacokinetic property of accumulating in immune system cells, notably phagocytes. This enables the compounds of Formula I to act predominantly if not exclusively at the inflammation site, by "riding" the macrolide within the very inflammation cells recruited to the locus of inflammation, and by inhibiting the production of inflammation mediators. In such a manner, the unfavourable systemic side-effects of corticosteroids are avoided or reduced and the activity of the compounds of the invention focused to the afflicted organ or tissue. After topical or systemic application, the hybrid molecules of the invention rapidly accumulate in inflammation cells, wherein they act by inhibiting the production of cytokines and chemokines as well as of other inflammation mediators, thus suppressing or inhibiting the inflammation.

The compounds of Formula I, which are the object of the present invention, their pharmacologically acceptable salts, solvates and prodrugs, and pharmaceutical compositions comprising them, have hitherto not been described, except for certain specific constructs comprising the macrolide FK-506 and the steroid dexamethasone, or the macrolide cyclosporin and the steroid dexamethasone or the macrolide pateamine A and the steroid dexamethasone. See WO 97/41255; Romo, D., et al., *J. Am. Chem. Soc.,* 1998, 120:12237–12254; Griffith, E. C., et al. Methods in Enzymology, 2000, 328:89–110. However, these documents do not disclose use of any such compounds either as anti-inflammatory substances or as immunosuppressants of unwanted immune responses or as inhibitors of eosinophilic accumulation in inflammation tissues, nor do they describe compositions containing such compounds as therapeutics for administration to a mammal, including a human.

We have recently found that certain compounds within Formula I:

I

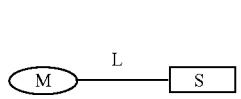

exert an improved therapeutic effect in the treatment of inflammation diseases, disorders and conditions. The symbol M in the above structure represents a macrolide subunit possessing the property of accumulation in inflammatory cells, S represents an anti-inflammatory steroid subunit and L represents a linker covalently linking M and S. Our co-pending commonly owned International Patent application PCT/HR02/00001 (incorporated herein by reference in its entirety, with a copy attached as Appendix A) describes compounds with the steroid subunit S linked via the chain L to position N/9a of 9-dihydro-9-deoxo-9a-aza-9a-homoerythromycin or to position C/3 of a des-cladinosyl azithromycin derivative or to position C/2' of the desozaminosyl group. However, hybrid compounds with the steroid subunit being linked with the position C/11 or N/9a with a modified or eliminated dimethylamino group on desozamine, which also possess the above mentioned therapeutic action, have not so far been described. Nor have hybrid compounds been described with the macrolide being linked to the steroid through position C/6 on the macrolide lactonic ring or through position C/4" of the cladinosyl group or through the amine group of position C/3' of the desozamine group or N/9a with linking to the steroid through 17α-OH group of the steroid subunit. Moreover, in the foregoing PCT/HR02/00001 other types of steroid-macrolide hybrid compounds are not specifically described. All such compounds are the subject of the present application.

The present invention is directed to
(a) new "hybrid" compounds represented by Formula I:

I

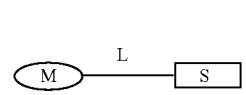

wherein M represents a macrolide subunit possessing the property of accumulation in inflammatory cells, S represents a steroid, as defined below, and L represents a linking group covalently linking M and S;

(b) compositions containing one or more of the foregoing compounds in an amount effective to combat inflammation and thereby to treat disorders and conditions involving inflammation in mammals, including humans; and (c) methods for using these compounds to treat such disorders and conditions.

The present compounds advantageously provide an improved therapeutic effect and/or an improved side effect profile.

Suitable macrolide subunits for the hybrid compounds of the present invention can be selected without limitation from multi-member lactonic ring molecules, wherein "member" refers to the carbon atoms or heteroatoms in the ring, and "multi" is a number greater than about 10, preferably from 10 to about 50, more preferably 12-, 14-, 15-, 16-, 17- and 18-member lactonic ring macrolides. 14- and 15-member ring macrolide subunits are particularly preferred, with azithromycin and its derivatives and erythromycin and its derivatives being most preferred.

More specific nonlimiting examples of molecules from which the macrolide subunit can be selected are the following:

(i) Macrolide antibiotics, including azalides, for example erythromycin, dirithromycin, azithromycin, 9-dihydro-9-deoxo-9a-aza-9a-homoerythromycin, HMR 3004, HMR 3647, HMR 3787, josamycin, erythromycylamine, ABT 773, flurithromycin, clarithromycin, tylosin, tilmicosin, oleandomycin, desmycosin, CP-163505, roxithromycin, miocamycin and rokitamycin and derivatives thereof, such as ketolides (e.g., 3-ketone), lactams (e.g., 8a- or 9a-lactams) and derivatives lacking one or more sugar moieties.

(ii) Macrolide immunosuppressants, such as FK 506, cyclosporin, amphotericin and rapamycin;

(iii) Macrolide antifungals with host cell inhibitory properties, such as bafilomycins, concanamycin, nystatin, natamycin, candicidin, filipin, etruscomycin, trichomycin.

Methodologies for the synthesis of the above macrolides not commercially available and synthetic manipulation of macrolides in general are known to those of ordinary skill in the art, or may be found in: Denis A. et al. Bioorg. & Med. Chem. Lett 1999, 9, 3075–3080; Agouridas C. et al. J. Med. Chem. 1998, 41, 4080–4100; and EP-00680967 (1998); Sun Or Y. et al. J. Med. Chem. 2000, 43, 1045–1049; U.S. Pat. No. 5,747,467 (1998); McFarland J. W. et al. J. Med. Chem. 1997, 40, 1041–1045; Denis A. at al. Bioorg.& Med. Chem. Lett. 1998, 8, 2427–2432; WO-09951616 (1999); Lartey et al. J Med Chem. 1995, 38, 1793–1798; EP 0984019; WO 98/56801, herein incorporated by reference in their entirety.

Additional suitable macrolides are known, some being disclosed in Bryskier, A. J., et al. *Macrolides, Chemistry, Pharmacology and Clinical Use*; Bryskier, Arnette Blackwell: Paris, 1993; pp 485–491, incorporated by reference in its entirety; in Ma, Z. et al. *Current Medicinal Chemistry—Anti-Infective Agents* 2002, 1, 15–34, also incorporated by reference in its entirety; in Romo, D. et al. *J. Am. Chem. Soc.* 1998, 120; 12237–12254; also incorporated by reference in its entirety. See, in particular the structures and derivatives for 14- and 16-member ring macrolides at pp 487–491 of Bryskier et al. and the various ketolide derivatives and syntheses in Ma et al. notably in all the structure tables and all the reaction schemes. All these macrolides after being conjugated to steroids are with the scope of the present invention. The foregoing specifically named macrolides as well as the ones referenced above are either commercially available or their structures and methods for their syntheses are known.

The structure and synthesis of the foregoing specifically enumerated compounds and several derivatives thereof is either known or well within the skill of the art.

In one subset of compounds according to the invention, if one constituent of the present compounds is FK-506 or cyclosporine, the other cannot be dexamethasone. In a further subset of the present compounds, FK-506, cyclosporine and pateamine A are excluded from the macrolide subunits altogether. However these provisos do not extend necessarily to novel methods for using the compounds defined above (including those which have FK-506, cyclosporin or pateamine A as a constituent), or to pharmaceutical compositions and dosage forms containing effective amounts of the present compounds for administration to mammalian animals or humans, particularly against inflammation.

It is important that the macrolide subunit derive from a macrolide having the property of accumulating within immune system cells recruited to the site of inflammation, especially phagocytic cells. Additional examples of macrolides accumulating within specific classes of cells may be found in: Pascual A. et al. *Clin. Microbiol. Infect.* 2001, 7, 65–69. (Uptake and intracellular activity of ketolide HMR 3647 in human phagocytic and non-phagocytic cells). Hand W. L. et al. *Int. J. Antimicrob. Agents*, 2001, 18, 419–425. (Characteristics and mechanisms of azithromycin accumulation and efflux in human polymorphonuclear leukocytes); Amsden G. W. *Int. J. Antimicrob. Agents*, 2001, 18, 11–15. (Advanced-generation macrolides: tissue-directed antibiotics); Johnson J. D. et al. *J. Lab. Clin. Med.* 1980, 95, 429–439.(Antibiotic uptake by alveolar macrophages); Wildfeuer A. et al. *Antimicrob. Agents Chemother.* 1996, 40, 75–79. (Uptake of azithromycin by various cells and its intracellular activity under in vivo conditions);. Scorneaux B. et al. *Poult. Sci.* 1998, 77, 1510–1521. (Intracellular accumulation, subcellular distribution, and efflux of tilmicosin in chicken phagocytes); Mtairag E. M. et al. *J. Antimicrob. Chemother.* 1994, 33, 523–536. (Investigation of dirithromycin and erythromycylamine uptake by human neutrophils in vitro); Anderson R. et al. *J. Antimicrob. Chemother.* 1988, 22, 923–933. (An in-vitro evaluation of the cellular uptake and intraphagocytic bioactivity of clarithromycin (A-56268, TE-031), a new macrolide antimicrobial agent); Tasaka Y. et al. *Jpn. J. Antibiot.* 1988, 41, 836–840. (Rokitamycin uptake by alveolar macrophages); Harf R. et al. *J. Antimicrob. Chemother.* 1988, 22, 135–140. (Spiramycin uptake by alveolar macrophages) herein incorporated by reference in their entirety. Most of the lactonic compounds defined above are known to have this property, but if not, it can be easily tested by a person of ordinary skill in the field of the invention, using one of the well-known assays for this purpose. For example, the procedure detailed by Olsen, K. M. et al. *Antimicrob. Agents & Chemother.* 1996, 40, 2582–2585, which is hereby incorporated by reference. Briefly, the cells to be tested, e.g., polymorphonuclear leukocytes can be obtained from venous blood of healthy volunteers by Ficoll-Hypaque centrifugation followed by 2% dextran sedimentation. Erythrocytes are removed by osmotic lysis, and PMN are evaluated by Trypan blue exclusion. Alternatively, other cell fractions can be separated and similarly tested.

Tritiated macrolide compounds (e.g., 10 µM) are incubated with $2.5 \times 10^6$ cells for 120 minutes (37° C., 5% $CO_2$, 90% relative humidity) and the cells are subsequently removed from compound-containing supernatant by centrifugation e.g., through a silicon oil-paraffin layer (86 vol. %: 14 vol. %). The amount of compound is determined, e.g., by scintillation counting, and a score significantly elevated above background indicates accumulation of the macrolide in the cells being tested. Alternatively, the compound is not radiolabelled but the amount of compound can be determined by HPLC.

Other assay methods that can be used are disclosed in Bryskier, A. J. et al. *Macrolides, Chemistry, Pharmacology and Clinical Use*; Arnette Blackwell: Paris, 1993; pp 375–386, incorporated by reference. See, in particular phagocytic uptake determination at pp 380–381 and the particular descriptions as to uptake and localization of macrolides at pp 381, 383 and 385 and the tables at 382.

In some preferred embodiments, this invention relates to compounds, their salts and solvates represented by Formula I, wherein M specifically represents a 14- or 15-member lactonic ring macrolide subunit more preferably represented by Formula II:

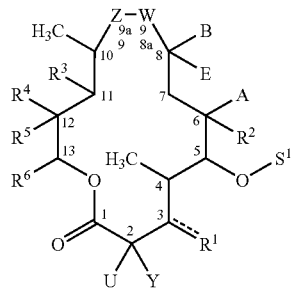

wherein
(i) Z and W independently are

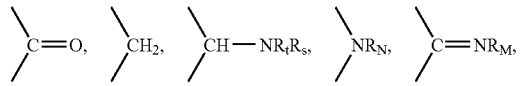

or a bond, wherein
$R_t$ and $R_s$ independently are H or alkyl (preferably methyl or H);
$R_M$ is OH, $OR^p$, alkoxy or substituted alkoxy (in either Syn or Anti configurations or mixtures thereof)
$R_N$ is H, $R^p$, alkyl, alkenyl, alkynyl, alkoxy, alkoxyalkyl, or —C(=X)—$NR_tR_s$; and
X is O or S;
provided that Z and W cannot both simultaneously be

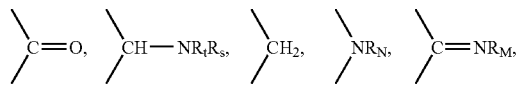

or a bond,
(ii) U and Y are independently H, halogen, alkyl, or hydroxyalkyl (preferably H, methyl, or hydroxymethyl);

(iii) $R^1$ is hydroxy, $OR^p$, —O—$S^2$, or =O;

(iv) $S^1$ is a sugar moiety at position C/5 (e.g., a desozamine group) of the formula:

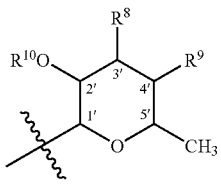

wherein
$R^8$ and $R^9$ are both hydrogen or together form a bond, or $R^9$ is hydrogen and $R^8$ is —N(CH$_3$)$R^y$, wherein
$R^y$ is $R^p$, $R^z$ or —C(O)$R^z$, wherein $R^z$ is hydrogen or cycloalkyl (preferably cyclohexyl) or alkyl (preferably a $C_1$–$C_7$ alkyl) or alkenyl (preferably $C_2$–$C_7$-alkenyl) or alkynyl (preferably $C_2$–$C_7$-alkynyl) aryl or heteroaryl or alkyl substituted with $C_2$–$C_7$ alkyl, $C_2$–$C_7$ alkenyl, $C_2$–$C_7$ alkynyl, aryl or heteroaryl ($R^y$ is preferably hydrogen, methyl, ethyl, n-propyl, i-propyl, n-butyl, —C(O)CH$_3$, —CH$_2$-phenyl, or cyclohexyl);
$R^{10}$ is hydrogen or $R^p$;

(v) $S^2$ sugar moiety (e.g., is a cladinosyl group) of the formula

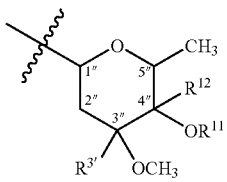

wherein $R^{3'}$ is H or methyl and $R^{11}$ is hydrogen or RP or O—$R^{11}$ is a group that with $R^{12}$ and with C/4" carbon atom forms a >C=O or epoxy group; $R^{12}$ is hydrogen or a group that with O—$R^{11}$ and with C/4" carbon atom forms a >C=O or epoxy group;

(vi) $R^2$ is H, hydroxy, $OR^p$ group, alkoxy (preferably $C_1$–$C_4$ alkoxy, most preferably methoxy) or substituted alkoxy;

(vii) A is H or methyl;

(viii) B is methyl or epoxy;

(ix) E is H or halogen (preferably fluorine);

(x) $R^3$ is hydroxy, $OR^p$ group or alkoxy (preferably $C_1$–$C_4$ alkoxy, most preferably methoxy), substituted alkoxy or $R^3$ is a group that can combine with $R^5$ to form a "bridge" (e.g., a cyclic carbonate or carbamate) or if W or Z is

$R^3$ is a group that can combine with W or Z to form a "bridge" (e.g., a cyclic carbamate);

(xi) $R^4$ is $C_1$–$C_4$ alkyl (preferably methyl);

(xii) $R^5$ is H, hydroxy, $OR^p$ group, $C_1$–$C_4$ alkoxy, substituted alkoxy or a group that may combine with $R^3$ to form a bridge (e.g., a cyclic carbonate or carbamate);

(xiii) $R^6$ is H or $C_1$–$C_4$ alkyl (preferably methyl or ethyl); wherein the subunit M has a linkage site through which it is linked to the subunit S via the linking group L, the linkage site being at one or more of the following:
  a. any reactive hydroxy, N, or epoxy group located on $S^1$, $S^2$, or an aglycono oxygen if $S^1$ or $S^2$ is cleaved off;
  b. a reactive >N—$R_N$ or —NR$_r$R$_s$ or =O group located on Z or W;
  c. a reactive hydroxy group located at any one of $R^1$, $R^2$, $R^3$, and $R^5$;
  d. any other group that can be first derivatized to a hydroxy or —NR$_r$R$_s$ group and then linked to K (e.g., OH→=O→epoxy→

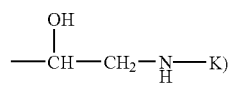

wherein K is the part of the linking molecule L;

One or more $R^p$ groups may be independently present in the macrolide subunit of Formula II, wherein $R^p$ represents a protective group which may be selected from alkyl (preferably methyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl). The amino protecting groups may be removed by conventional techniques. Thus, for example acyl groups like alkanoyl, alkoxycarbonyl or aroyl may be removed by solvolysis, e.g. by hydrolysis under acidic or basic conditions. Arylmethoxycarbonyl group (benzyloxycarbonyl) may be cleaved by hydrogenolysis in the presence of a catalyst such as palladium-on-charcoal.

L represents the structure VA or VB:

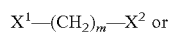  VA

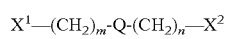  VB wherein $X^1$ is selected from: —CH$_2$, —CH$_2$—NH—, —C(O)—, —OC(O)—, =N—O—, —OC(O)NH— or —OC(O)NH—;

$X^2$ is selected from: —NH—, —CH$_2$—; —NHC(O)—, —C(=O) or —OC(O)—;

Q is —NH— or —CH$_2$—;

wherein each —CH$_2$— or —NH— group are optionally substituted by $C_1$–$C_7$-alkyl, $C_2$–$C_7$-alkenyl, $C_2$–$C_7$-alkynyl, C(O)$R^x$, C(O)O$R^x$, C(O)NH$R^x$ wherein $R^x$ may be $C_1$–$C_7$-alkyl, aryl or heteroaryl; the symbols m and n are independently a whole number from 0 to 8 with the proviso that if Q=NH; n cannot be zero.

This definition of the linking group is preferred not only for hybrids of steroids and macrolides of Formula II but for any conjugate within Formula I. Other linking groups can be used as long as they provide the necessary spacer and can serve to link one subunit of the Formula I with the other, as is well-known in the art. See, e.g., U.S. Pat. No. 6,297,260, which is incorporated by reference in its entirety, especially its claim 1 and the specific list of steroids.

S is a steroid subunit, preferably of Formula X:

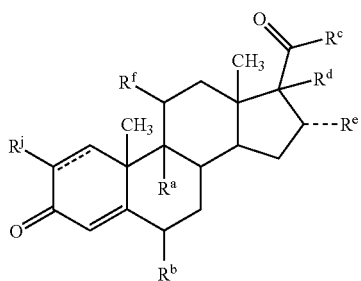

wherein $R^a$ and $R^b$ are, independently of each other, hydrogen or halogen;

$R^c$ is hydroxy, alkoxy (preferably methoxy), substituted alkoxy, alkyl, thiocarbamoyl, carbamoyl or a valence-bond;

$R^d$ and $R^e$ are, independently of each other, hydrogen, OH, $CH_3$ or $C_1$–$C_4$ alkoxy (preferably methoxy or n-propoxy) or each are a group that forms a 1,3-dioxolane ring with the other (optionally alkyl or alkenyl mono-or di-substituted) (preferably a 2,2-dimethyl or 2-monopropyl or trans-propenyl ring) or a valence bond;

$R^f$ is hydrogen, hydroxy, chloro, or =O forming a keto group with the carbon atom it is attached to;

$R^j$ is hydrogen or chloro and their pharmacologically acceptable salts and solvates.

Alternatively with the present invention are steroid subunits disclosed in WO 94/14834, wherein instead of the group >CH—C(O)—$R^c$ they have the group >CH—S(O)$_n$—$R^c$ wherein n is an integer of 0 to 2. See WO 94/14834 incorporated in its entirety by reference, especially pp 2–3.

More generally, steroids useful as a source of steroid subunits include, but are not limited to, corticosteroids (such as glucocorticoids and mineralocorticoids) and androgens. Non-limiting examples of corticosteroids include cortisol, cortisone, clobetasol, hydrocortisone, fludrocortisone, fludroxycortide, flumetasone, flunisolide, fluocinolone, fluocinonide, fluocortolone, fluorometholone, prednisone, prednisolone, 6-alpha-methylprednisolone, triamcinolone, alclometasone, beclometasone, betamethasone, budesonide, dexamethasone, amcinonide, cortivazol, desonide, desoximethasone diflucortolone, difluprednate, fluclorolone and dichlorisone, fluperinidene, fluticasone, halcinonide, meprednisone, methylprednisolone, paramethasone, prednazoline, prednylidene, tixocortol, triamcinolone, and acid derivatives thereof, e.g., acetate, propionate, dipropionate, valerate, phosphate, isonicotinate, metasulfobenzoate, tebutate, and hemisuccinate).

The symbols M, L and S represent three different subunits of the compounds represented by the structure I. The symbol M represents the macrolide subunit and the symbol S the steroid subunit which is linked via the linker molecule L with a linkage site of the subunit M. As discussed above, when M is an azithromycin lactone ring then the linkage is preferably effected through position C/3 of the aglycone moiety or at position C/6, C/11 or at position N/9a of the compound of Formula II, or through position C/4" of the $S^2$ group or through the amine at 3' or 2' of the $S^1$ group.

Bold-faced bonds in the formulas presented herein denote bonds raised above the paper plane (β-position). Dash-drawn bonds denote bonds situated below the paper plane (α-position). Parallel full and broken lines denote bonds that can be either single or double. A single broken line denotes a bond either above or below the paper plane.

Unless stated otherwise, the following terms have the meanings ascribed to them below.

"Halogen" means a halogen atom which may preferably be: fluorine, chlorine or bromine (the most preferably fluorine or chlorine).

"Alkyl" means a linear or branched saturated monovalent hydrocarbon radical of one to ten carbon atoms, more preferably one to six carbon atoms The preferred straight-chain or branched-chain alkyls include methyl, ethyl, propyl, iso-propyl, butyl, sec-butyl and tert-butyl. Methyl is most preferred. Alkyl groups may be substituted with one up to five substituents including halogen (preferably fluorine or chlorine), hydroxy, alkoxy (preferably methoxy or ethoxy), acyl, acylamino cyano, amino, N-($C_1$–$C_4$)alkylamino (preferably N-methylamino or N-ethylamino), N,N-di($C_1$–$C_4$-alkyl)amino (preferably dimethylamino or diethylamino), aryl (preferably phenyl) or heteroaryl, thiocarbonylamino, acyloxy, amino, amidino, alkylamidino, thioamidino, aminoacyl, aminocarbonylamino, aminothiocarbonylamino, aminocarbonyloxy, aryl, heteroaryl, aryloxy, aryloxyaryl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, cycloalkoxy, heteroaryloxy, heterocyclyloxy, and oxycarbonylamino. Such substituted alkyl groups are within the present definition of "alkyl." The present definition of alkyl carries over to other groups having an alkyl moiety such as alkoxy.

"Alkenyl" means a linear or branched monovalent hydrocarbon radical of two to ten and preferably two to six carbon atoms which has at least one double carbon-carbon bond. Alkenyl groups may be substituted with the same groups as alkyl and such optionally substituted alkenyl groups are encompassed within the term "alkenyl". Ethenyl, propenyl, butenyl and cyclohexenyl are preferred.

"Alkynyl" means a linear or branched monovalent hydrocarbon radical, having a straight-chain or a branched-chain of two to ten, and preferably two to six carbon atoms and containing at least one and preferably no more than three triple carbon-carbon bonds. Alkynyl groups can be substituted with the same groups as alkyl, and the substituted groups are within the present definition of alkynyl. Ethynyl, propynyl and butynyl groups are preferred.

"Cycloalkyl" means a cyclic group having 3–8 carbon atoms having a single ring optionally fused to an aryl or heteroaryl group. The cycloalkyl groups can be substituted as specified for "aryl" below, and the substituted cycloalkyl groups are within the present definition of "cycloalkyl". Preferred cycloalkyls are cyclopentyl and cyclohexyl.

"Aryl" means an unsaturated aromatic carbocyclic group having 6–14 carbon atoms having a single ring such as phenyl or multiple fused rings such as naphthyl. Aryl may optionally be further fused to an aliphatic or aryl group or can be substituted with one or more substituents such as halogen (fluorine, chlorine and/or bromine), hydroxy, $C_1$–$C_7$ alkyl, $C_1$–$C_7$ alkoxy or aryloxy, $C_1$–$C_7$ alkylthio or arylthio, alkylsulfonyl, cyano or primary or nonprimary amino.

"Heteroaryl" means a monocyclic or a bicyclic aromatic hydrocarbon ring having from 2 to 10 carbon atoms and from 1 to 4 heteroatoms, such as O, S or N. The heteroaryl ring may optionally be fused to another heteroaryl, aryl or aliphatic cyclic group. Examples of this type are furan, thiophene, imidazole, indole, pyridine, oxazole, thiazole, pyrrole, pyrazole, tetrazole, pyrimidine, pyrazine and triazine, with furan, pyrrole, pyridine and indole being preferred. The term includes groups that are substituted with the same substituents as specified for aryl above.

"Heterocyclic" means a saturated or unsaturated group having a single or multiple rings and from 1 to 10 carbon atoms and from 1–4 heteroatoms selected from nitrogen, sulfur or oxygen, wherein in a fused ring system the other ring or rings can be aryl or heteroaryl. Heterocyclic groups can be substituted as specified for alkyl groups and the thus substituted heterocyclic groups are within the present definition.

When $R^c$ represents a valence-bond, the steroid subunit S is linked via $R^c$ with the chain L to the macrolide subunit M. The symbol K is sometimes used to refer to the part of the L group, linked to M, or to S at the context requires.

In the preparation of the compounds represented by the structure I, of the specified pharmacological activity, certain new compounds were prepared as intermediates in the preparation of pharmacologically active compounds. The present invention also relates to such intermediates.

The present invention also encompasses pharmaceutically acceptable salts of the present compounds. Pharmaceutically suitable salts of the compounds of the present invention include salts with inorganic acids (e.g. hydrochloric, hydrobromic, phosphoric, metaphosphoric, nitric or sulfuric acid) or organic acids (e.g. tartaric, acetic, mesylic, trifluoroacetic, citric, maleic, lactic, fumaric, benzoic, succinic, methanesulfonic, oxalic and p-toluenesulfonic acids).

A further aspect of the present invention are the solvates (preferably hydrates) formed by the compounds represented by the structure I or their salts.

The present invention also encompasses pharmaceutically acceptable salts of the present compounds. Pharmaceutically suitable salts of the compounds of the present invention include salts with inorganic acids (hydrochloric, hydrobromic, phosphoric, metaphosphoric, nitric or sulfuric acid) or organic acids (tartaric, acetic, methane-sulfonic, trifluoroacetic, citric, maleic, lactic, fumaric, benzoic, succinic, methanesulfonic, oxalic and p-toluenesulfonic acids).

The present invention also encompasses prodrugs of Formula I compounds, i.e., compounds which release an active parent drug according to Formula (I) in vivo when administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or carboxy group of a Formula I compound is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of Formula I.

The compounds of Formula I have one or more chirality centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". The present invention encompasses all individual isomers of compounds of Formula I. The description or naming of a particular compound in the specification and claims is intended to include both individual enantiomers and mixtures, racemic or otherwise, thereof. Methods for the determination of stereochemistry and the separation of stereoisomers are well-known in the art.

The present invention also encompasses stereoisomers of the syn-anti type, encountered when an oxime or similar group is present. The group of highest Cahn Ingold Prelog priority attached to one of the terminal doubly bonded atoms of the oxime, is compared with hydroxyl group of the oxime. The stereoisomer is designated as Z (zusammen=together) or Syn if the oxime hydroxyl lies on the same side of a reference plane passing through the C═N double bond as the group of highest priority; the other stereoisomer is designated as E (entgegen=opposite) or Anti.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The benefit to a subject to be treated is either statically significant or at least perceptible to the patient or to the physician A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The four classic symptoms of acute inflammation are redness, elevated temperature. Swelling, and pain in the affected area, and loss of function of the affected organ.

Symptoms and signs of inflammation associated with specific conditions include:

rheumatoid arthritis—pain, swelling, warmth and tenderness of the involved joints; generalized and morning stiffness;

insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease;

autoimmune thyroiditis—weakness, constipation, shortness of breath, puffiness of the face, hands and feet, peripheral edema, bradycardia;

multiple sclerosis—spasticity, blurry vision, vertigo, limb weakness, paresthesias;

uveoretinitis—decreased night vision, loss of peripheral vision;

lupus erythematosus-joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma—Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis—fever, pain, swelling, tenderness;

other inflammatory brain disorders, such as meningitis, Alzheimer's disease, AIDS dementia encephalitis—photophobia, cognitive dysfunction, memory loss;

other inflammatory eye inflammations, such as retinitis—decreased visual acuity;

inflammatory skin disorders, such as, eczema, other dermatites (e.g., atopic, contact), psoriasis, burns induced by UV radiation (sun rays and similar UV sources)—erythema, pain, scaling, swelling, tenderness;

inflammatory bowel disease, such as Crohn's disease, ulcerative colitis—pain, diarrhea, constipation, rectal bleeding, fever, arthritis;

asthma—shortness of breath, wheezing;

other allergy disorders, such as allergic rhinitis—sneezing, itching, runny nose conditions associated with acute trauma such as cerebral injury following stroke—sensory loss, motor loss, cognitive loss;

heart tissue injury due to myocardial ischemia—pain, shortness of breath;

lung injury such as that which occurs in adult respiratory distress syndrome—shortness of breath, hyperventilation, decreased oxygenation, pulmonary infiltrates;

inflammation accompanying infection, such as sepsis, septic shock, toxic shock syndrome—fever, respiratory failure, tachycardia, hypotension, leukocytosis;

other inflammatory conditions associated with particular organs or tissues, such as
  nephritis (e.g., glomerulonephritis)-oliguria, abnormal urinalysis;
  inflamed appendix—fever, pain, tenderness, leukocytosis;
  gout—pain, tenderness, swelling and erythema of the involved joint, elevated serum and/or urinary uric acid;
  inflamed gall bladder—abdominal pain and tenderness, fever, nausea, leukocytosis;
  chronic obstructive pulmonary disease—shortness of breath, wheezing;
  congestive heart failure—shortness of breath, rales, peripheral edema;

Type II diabetes—end organ complications including cardiovascular, ocular, renal, and peripheral vascular disease lung fibrosis—hyperventilation, shortness of breath, decreased oxygenation;

vascular disease, such as atherosclerosis and restenosis—pain, loss of sensation, diminished pulses, loss of function and alloimmunity leading to transplant rejection—pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

The present invention also relates to possible tautomeric forms which can be formed by individual compounds of Formula I.

Further preferred are compounds of Formula I wherein M represents a group of Formula II wherein Z is >N—$R_N$ wherein $R_N$ is hydrogen or a methyl; W is >$CH_2$; B is methyl; E is hydrogen; $R^2$ is hydroxy; A is methyl; $R^8$ at the C/3' position in $S^1$ is selected from: hydrogen, amino, N-methylamino, N,N-dimethylamino, N-methyl-N-($C_2$–$C_4$)-alkylamino, N-methyl-N-methylcarbonylamino, N-methyl-N-benzylamino or N-methyl-N-cyclohexylamino; U=H, Y=$CH_3$, $R^1$ is O—$S^2$ group wherein $S^2$ is a cladinosyl group wherein the 3" position is both methyl and methoxy substituted, $R^6$ is ethyl, $R^5$ is methyl; $R^{11}$ and $R^{12}$ are hydrogen and $R^{13}$ is methyl; $R^4$ is OH or forms a cyclic carbonate bridge with $R^3$, $R^3$ is OH or forms a cyclic carbonate bridge with $R^4$, and the 3' position of the desozamine group is H or —N($CH_3$)$R^y$ as defined above. The linkage is through the N of Z, or through the O of $R^3$. In the latter case, Z is NH.

Also preferred are compounds of Formula I wherein M represents a group of Formula II wherein: Z is >NH or >$NCH_3$ or >NC(O)NH$R^x$ wherein $R^x$ is iso-propyl; W is >C=O or >$CH_2$ (provided that when Z is >$NCH_3$ W cannot be >C=O); $R^2$ is hydroxy or methoxy; A is methyl; E is hydrogen; B is methyl; $R^3$ is hydroxy; $R^5$ is methyl; $R^4$ is hydroxy or methoxy; $R^6$ is ethyl; $R^1$ is a O—$S^2$ group wherein $S^2$ is a cladinosyl group wherein $R^{13}$ is methyl; $R^{11}$ is hydrogen, or O—$R^{11}$ is a group that forms with $R^{12}$ and with C/4" carbon atom a >C=O or epoxy group, $R^{12}$ is hydrogen or a group that forms with O—$R^{11}$ and with a C/4" carbon atom a >C=O or epoxy group; C/3' position of the $S^1$ group is hydrogen, amino or N-($C_1$–$C_6$)-alkylamino or N,N-($C_1$–$C_6$)-dialkylamino. The linkage is through the amino of $R^8$ at the C/3' position or through the oxygen of $R^2$ at C/6 position or through the carbon of $R^{12}$ or the oxygen of $R^{11}$ both at C/4" position.

Methods of Preparation A

A further aspect of the present invention relates to a method for the preparation of specific compounds within Formula I comprising:

a) for the compounds of Formula I, wherein L has $X^1$ being —$CH_2$—, $X^2$ being —NH—, and Q is absent (Formula VA), a reaction of carboxylic acid of the steroid subunit of Formula Xa:

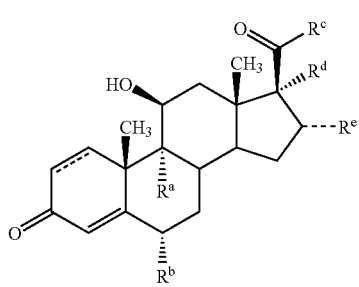

Xa wherein —C(O)R$^c$ is an activated carboxylic acid and R$^a$, R$^b$, R$^d$, and R$^e$ are defined as in Formula X, with a free amino group of the macrolide subunit of Formula VIa:

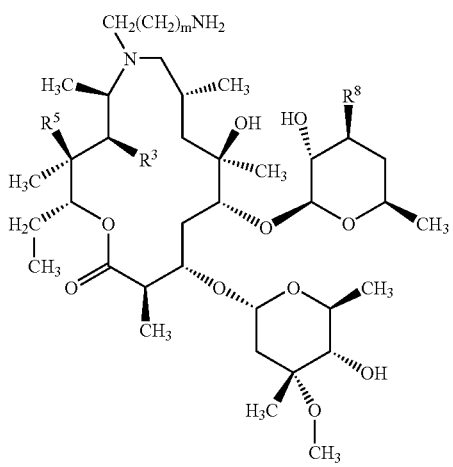

VIa wherein R$^3$, R$^5$, and R$^8$ are defined in connection with Formula II above;

b) for the compounds of Formula I, wherein X$^1$ in L is —C(O)NH— and X$^2$ is —NH— (also Formula VA), the reaction of the carboxylic acid of the steroid subunit of the structure X, wherein —C(O)R$^c$ is an activated carboxylic acid, with a free amino group of the macrolide subunit of the structure VIb:

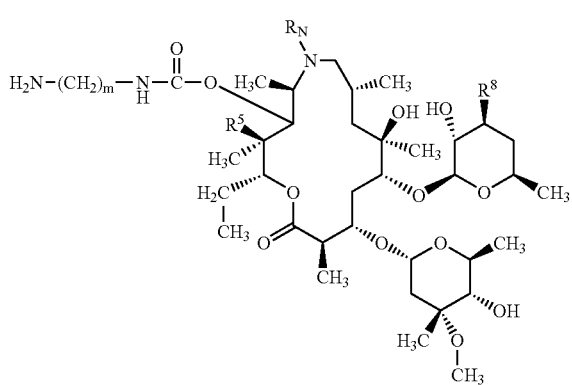

VIb wherein R$_N$, R$^5$, and R$^8$ are as defined in Formula II and m is as defined in Formula VA.

c) for the compounds of Formula I, wherein R$^8$ is H, —NH—CH$_3$, or —N(CH$_3$)R$^y$ by removal or change of the —N(CH$_3$)$_2$ group on the desozamino sugar of a compound of Formula I having a macrolide subunit of Formula VIc:

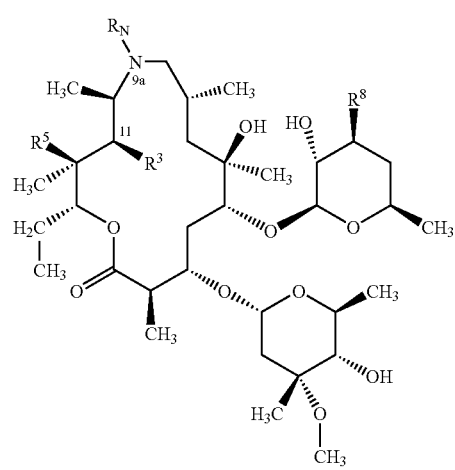

VIc wherein R$_N$, R$^3$, and R$^8$ are as defined in Formula II.

Methods of Preparation:

a) A compound within Formula I is prepared by a reaction of a carboxylic acid of the steroid subunit of the structure X and the amino group of the macrolide subunit of the structure VIa according to the process as described in International Application No PCT/HR02/00001, whereby the amide linkage is effected, using the usual acid derivatives having an activating effect on carboxylic acid, such as anhydrous halogenides with mixed anhydrides especially carbodiimides or benzotriazole (e.g. hydroxybenzotriazole). The reaction proceeds in the presence of a base (preferably an organic), e.g. triethylamine, at room temperature under an inert atmosphere, e.g., argon blanket over the period from several hours to several days. (D. Romo et al., *J. Am. Chem. Soc.*, 1998, 120, 12237).

Steroid subunits of the structure X are either commercially available products or have been obtained by known methods (Suzuki, T. et al., *Chem. Soc., Perkin Trans.* 1 1998, 3831–3836.), (McLean, H. M. et al., *J. Pharm. Sci.* 1994, 83, 476–480.), (Little, R. J. et al., *Pharm. Res.* 1999, 16, 961–967.), (Kertesz D. J. et al., *J. Org. Chem.* 1986, 51, 2315–2328.), (Bodor, N. S., U.S. Pat. No. 4,710,495 1987), (Phillipps, G. et al., *J. Med. Chem.* 1994, 37, 3717–3729) all incorporated in their entirety by reference.

Starting macrolide subunits of the structure VIa may be obtained by the action of corresponding cyanoalkenyls (preferably acrylonitriles) on the corresponding macrolide subunits and then by hydrogenation of the formed nitrile, according to the procedures of Bright, U.S. Pat. No. 4,474,768, Oct. 2, 1984; and Bright, G. M. et al., 1998, *J. Antibiot.* 41:1029–1047.

b) Preparation of a compound of Formula I is carried out by a reaction of the carboxylic acid of the steroid subunit represented by the structure X and the amino group of the macrolide subunit of the structure VIb, whereby the amine bond is prepared, and the process proceeds in the manner and under conditions as described in the method a) above.

Starting macrolide subunits of the structure VIb may be obtained by the action of the corresponding diaminoalkane (preferably diaminobutane) on the macrolide subunit VII:

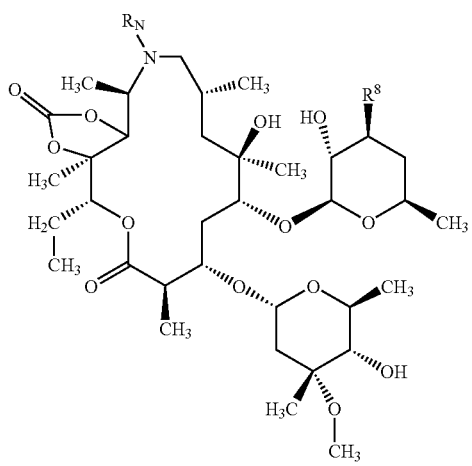

which can be obtained in by the action of ethylcarbonate on the macrolide subunit, as reported in the literature (EP 0984019 A1, which is hereby incorporated by reference).

c) A compound within Formula I is prepared by modification or elimination of the —N(CH$_3$)$_2$ group R$^8$ of the desozamine sugar of compounds having a macrolide subunit represented by Formula VIc. Modification can be effected by demethylation of one of the two methyl groups, e.g., by UV radiation. By alkylation or acylation of the obtained compound of Formula I, wherein R$^8$ is a NH(CH$_3$) group, a new class of compounds of Formula I is formed, wherein R$^8$ is —N(CH$_3$)R$^z$. It is possible to eliminate the —N(CH$_3$)$_2$ group by oxidizing it and by forming of a corresponding N-oxide, which on heating yields the compounds of Formula I, wherein R$^8$ is hydrogen.

Compounds of Formula I may generally be obtained so that: first the N(CH$_3$)$_2$ group of the macrolide subunit is modified, and then the modified macrolide subunit is linked by a chain to the steroid subunit; or, first the steroid and the macrolide subunit possessing the N(CH$_3$)$_2$ group are linked by a linking group through another position of the macrolide molecule and then the chemical change on the present N(CH$_3$)$_2$ group is performed. The linkage group L may be, for example, attached to the macrolide subunit of Formula VIc at position 9a or 11.

To prevent undesirable side-reactions, it is frequently necessary to protect certain groups such as e.g. hydroxy or amino groups. For this purpose, a large number of protective groups can be employed [Green T W, Wuts P G H, Protective Groups in Organic Synthesis, John Wiley and Sons, 1999] and their selection, use and elimination present the usual methods in chemical synthesis, as is well within the skill for the art.

A still further aspect of the present invention relates to methods for making the compounds represented by Formula I comprising:

d) for the compounds of Formula I, wherein X$^1$ is —CH$_2$— and Q are —NH-(L is VB);

a reaction of (i) the carboxylic acid of the steroid subunit of the structure IVa:

IVa

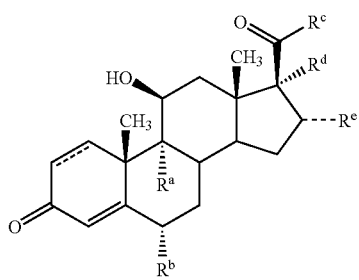

wherein —C(O)R$^c$ is an activated carboxylic acid, and of (ii) a free amino group of the macrolide subunit of the structure Va:

Va

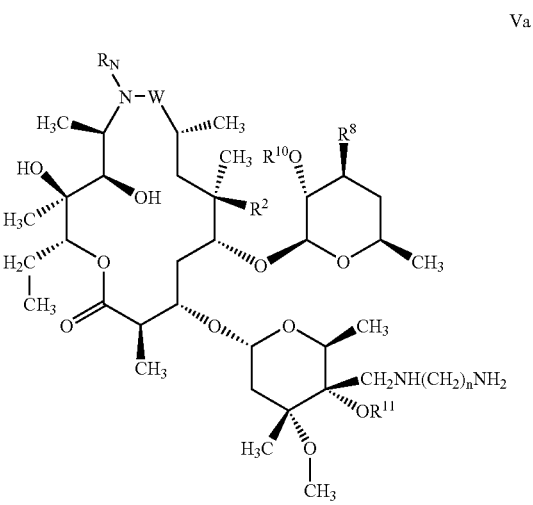

wherein W is >C=O or —CH$_2$—; R$_N$, R$^2$, R$^{10}$, R$^{11}$, and R$^8$ are as defined in Formula II and n is as defined in Formula VA.

e) for the compounds of the structure I, wherein Q and X$^1$ are —CH$_2$— (L is VB), a reaction of carboxylic acid of the steroid subunit of the structure IVa, wherein —C(O)R$^c$ has the meaning of activated carboxylic acid and of free amino group of the macrolide subunit of the structure Vb:

Vb

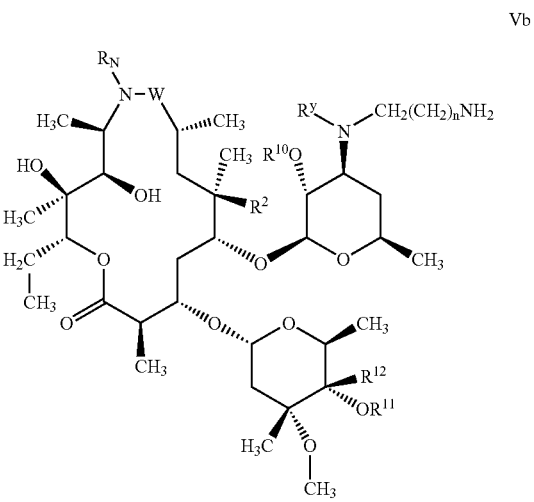

wherein W is >C=O or —CH$_2$—; R$_N$, R$^2$, R$^{10}$, R$^{11}$, R$^{12}$, and R$^y$ are as defined in Formula II and n is as defined in Formula VA.

f) for the compounds of Formula I, wherein X$^1$ is —C(O)— and Q is —NH—, (L is VB), by reaction of the free amino group of the steroid subunit of the structure IVc:

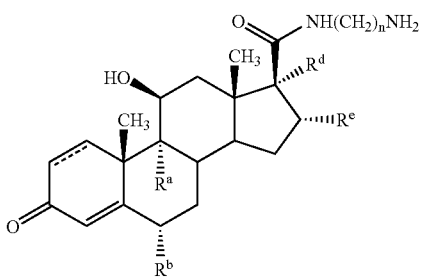

wherein $R^a$, $R^b$, $R^d$, and $R^e$ are as defined in Formula X, and of a —C═C— bond of the macrolide subunit of the structure Vc or Vd:

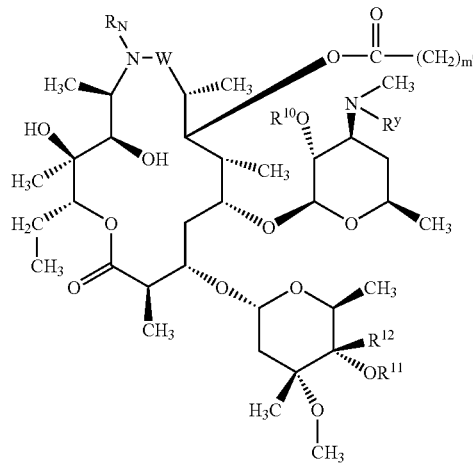

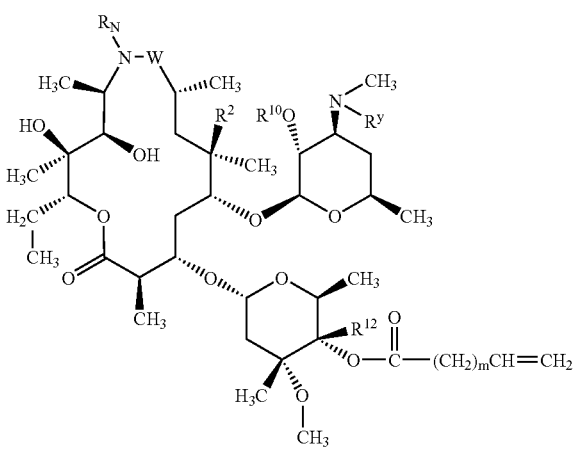

wherein W is >C═O or —CH$_2$—; $R_N$, $R^2$, $R^{10}$, $R^{11}$, $R^{12}$, and $R^y$ are as defined in Formula I and n is as defined in Formula VA.

Methods of Preparation:

d) The compound of Formula I is prepared by a reaction of the carboxylic acid of the steroid subunit of Formula IVa and the amino group of the macrolide subunit of the structure Va, whereby an amide bond is prepared; it is carried out using the usual acid derivatives having an activating effect on carboxylic acid, such as halogenides, mixed anhydrides especially carbodiimides or benzotriazole. The reaction proceeds in the presence of a base (mainly organic) e.g. triethylamine at room temperature under an inert atmosphere, such as nitrogen or argon over a period of several hours to several days (Romo D et al., *J. Am. Chem. Soc.* 1998, 120:12237).

The steroid subunits of the structure IVa are either commercially available products or have been obtained by the described methods (Suzuki T et al., *Chem. Soc., Perkin Trans.* 1 1998, 3831–3836; McLean H M et al., *J. Pharm. Sci.* 1994, 83:476–480; Little R J et al., *Pharm. Res.* 1999, 16:961–967; Kertesz D J et al., *J. Org. Chem.* 1986, 51:2315–2328 and U.S. Pat. No. 471,049).

The starting macrolide subunits of the structure Va may be obtained by the action of the corresponding alkylenediamines on the macrolide subunits of the structure VI:

wherein $R^{11}$ and $R^{12}$ together with the adjacent C atom from the cladinosyl ring form a three-membered oxyrane ring. Such compounds were prepared by the procedures described for the preparation of analogue compounds in Patent Application WO 98/56801. Thus, for example, by oxidation of the free hydroxyl group $OR^{11}$, where $R^{11}$ is H, of the macrolide subunit of the structure VI, a corresponding ketone is obtained, where $R^{11}$ and $R^{12}$ form a >C═O group with the C/4" carbon atom which, by reduction with a metal hydride (preferably NaH) under trimethylsulphoxonium-iodide yields the above mentioned oxyrane ring.

e) The preparation of a compound within Formula I is carried out by a reaction of the carboxylic acid of the steroid subunit of Formula IVa and a free amino group of the macrolide subunit of Formula Vb, whereby an amide bond is prepared, and the process proceeds in the manner and under conditions as described in the method d) above. The starting macrolide subunits of the structure Vb may be obtained by the action of a corresponding cyanoalkylhalogenide or cyanoalkenyl (preferably acrolonitrile) on the macrolide subunits of the structure VI, wherein $R^y$ is H, and which may be obtained by demethylation of the macrolide subunit of the structure VI wherein $R^y$ is a CH$_3$ group under UV radiation (Bright M et al., *J. Antibiot.* 1988, 41:1029).

f) A compound witin Formula I may be prepared by reacting of an amino group of the steroid subunit of Formula IVb and the —C═C— group of the macrolide subunit of the structure Vc or Vd, whereby an amino bond is prepared. Steroid subunits of the structure IVb are either known compounds or may be obtained from the steroid subunit IVa, wherein $R^c$ is an OH group, by the action of alkylenediamine. The starting macrolide subunits of the structure Vc and Vd may be obtained by the action of a corresponding halogenalkanoylchloride (preferably 3-chlorpropionylchloride) on the free OH group of the macrolide subunit of Formula VI.

g) for the compounds of Formula I, wherein $X^1$ is —C(O)— and Q is —NH—, (L is VB), by reaction of a —C=C— bond of the steroid subunit of the structure IVd:

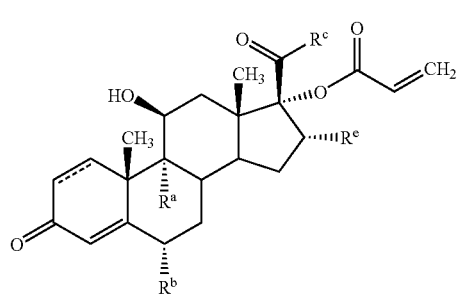

IVd wherein $R^a$, $R^b$, $R^c$, and $R^e$ are as defined in Formula X, and the free amino group of a macrolide subunit of the structure Va, VIa, VIb or Vb that are described before.

Methods of Preparation:

g) The compound of Formula I is prepared by a reaction of the steroid subunit of Formula IVd and the amino group of the macrolide subunit of the structure Va, VIa, VIb or Vb whereby an amide bond is prepared. The starting steroid subunits of the structure IVd may be obtained by the action of a corresponding halogenalkanoylchloride (preferably 3-chlorpropionylchloride) on the steroid subunit of Formula IVa wherein $R^d$ is an OH group (Phillipps, G. et al., J. Med. Chem. 1994, 37, 3717–3729).

Compounds of Formula I may generally be obtained in the following way: one end of the linker chain L is first linked to the macrolide subunit M, and then the other end of the chain is joined to the steroid subunit; or, one end of the chain L is first linked to the steroid subunit S and then the other end of the chain to the macrolide subunit M, or finally, one part of the chain is linked to the macrolide subunit M, whereas the other part of the chain is linked to the steroid subunit S, with the ends of the chain parts being then chemically linked to form the chain L.

More general schemes for making the compounds of the invention are apparent to a person of skill in the field of the invention in light of the foregoing. Compounds within Formula I can be prepared by the following processes.

a) Compounds of Formula I, where $X^2$ is —NH—, can be formed by reacting (i) a steroid anti-inflammatory subunit represented by Formula V:

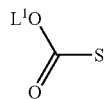

wherein $L_1$ represents a leaving group (such as hydroxy), and (ii) a free amino group of a macrolide subunit represented by Formula VId:

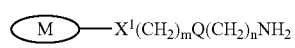

VId

The reaction is generally performed with acid derivatives which have the ability to activate the carboxylic acid group of steroidal anti-inflammatory subunit, such as halogenides, mixed anhydrides and especially carbodiimides (such as -(3-dimethylaminopropyl)-3-ethyl-carbodiimide (EDC)) and benzotriazoles. The reaction proceeds in the presence of a base, such as an organic base (e.g., triethylamine), at room temperature under an inert atmosphere such as nitrogen or argon. The reaction may require several hours to several days to come to completion.

For example, when L is —K—NH— (wherein K is the portion of the L molecule attached to the macrolide) the compound of Formula I can be formed by derivatizing an NH group on the macrolide ring to an —N—K—(NH$_2$)— group and reacting the derivatized macrolide with a steroid anti-inflammatory subunit represented by Formula V:

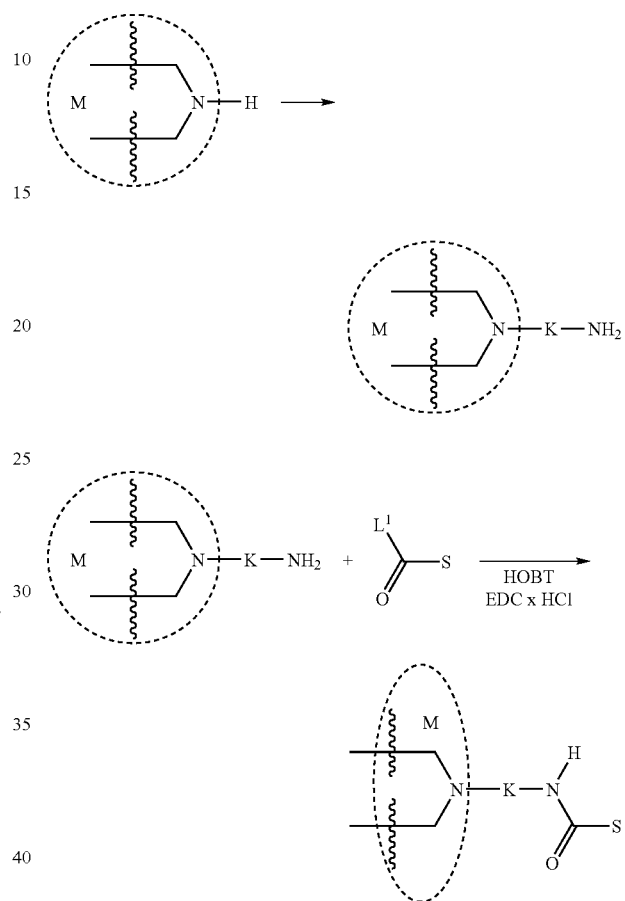

This process may also be performed when the NH group in the macrolide is attached at the 3' position of a sugar ring $S^1$ (i.e., a desozamine sugar) of the macrolide:

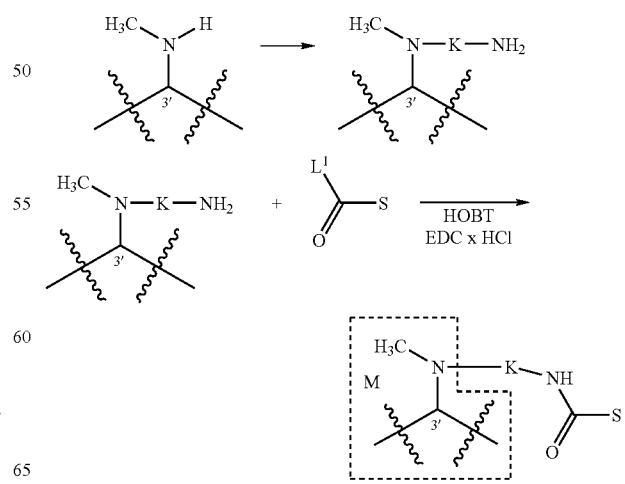

or the 4 position of the sugar ring $S^2$:

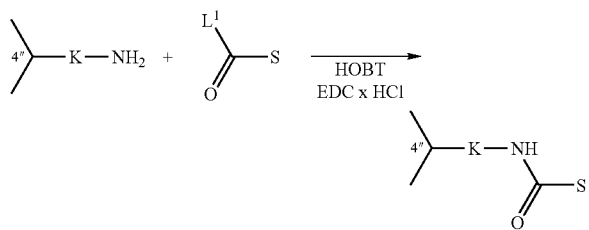

b) Compounds represented by Formula I, where $X^2$ is —OC(O)—, can be formed by reacting a compound of Formula V and the free hydroxyl group of a macrolide subunit represented by Formula VIe:

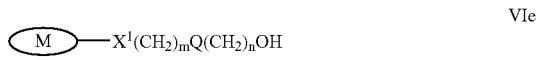

VIe

The reaction is generally performed with acid derivatives which have the ability to activate the carboxylic acid group such as halogenides, mixed anhydrides and especially carbodiimides and benzotriazoles. The reaction is typically performed at room temperature under an inert atmosphere such as nitrogen or argon. The reaction may require several hours to several days to come to completion.

The starting macrolide subunits of the structure VIb are known compounds or may be obtained according to the procedures described for analogous compounds, such as those described in Costa A M et al., *Tetrahedron Letters* 2000, 41:3371–3375, which is hereby incorporated by reference in its entirety. See, also Bright U.S. Pat. No. 4,474,768 and Bright, G. M., et al, *J. Antibiot.*, 1988, 41:1029–1047, both incorporated in their entirety by reference.

For example, when linkage L is —K—O—, the compound of Formula I can be formed by (1) derivatizing an NH group on a macrolide to an N—K—OH group and (2) reacting the derivatized macrolide with the free carboxylic acid group on a steroid S:

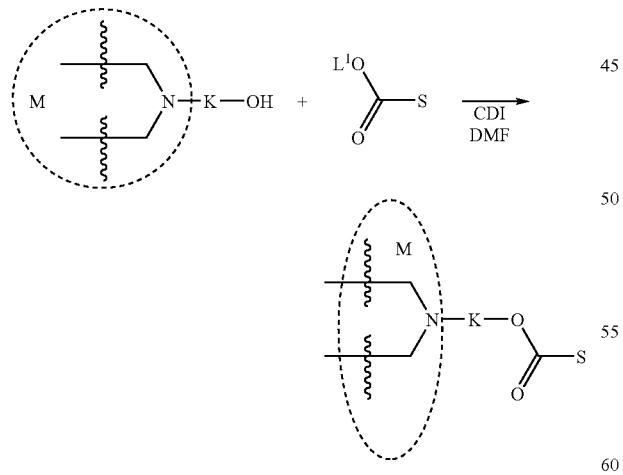

The linkage group —K—OH can be attached to the secondary nitrogen atom of the macrolide subunit as follows. The macrolide subunit is reacted with an alkenoyl derivative, such as $CH_2=CH(CH_2)_m$, C(O)O-Alkyl (e.g., methylacrylate). The ester group (i.e., —C(O)O-Alkyl) is then reduced, such as with a metal hydride (e.g., $LiAlH_4$) in an anhydrous organic solvent, to yield the macrolide subunit having the linkage group —K—OH (i.e., M-K—OH). The reduction is typically performed at a low temperature and preferably at 0° C. or lower.

This process can also be performed when the NH group is attached at the 3' position of a sugar ring in the macrolide (such as a sugar at the 3 position of the macrolide).

c) Compounds represented by Formula I, wherein $X^1$ is —OC(O)—, Q is —NH— and $X^2$ is —NH— can be prepared by reacting a macrolide subunit represented by the formula

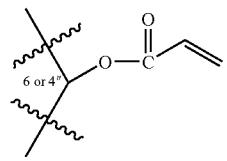

For example this process can be performed when OH group is atached at the C/6 or C/4" position of the macrolide subunit represeted by Formula:.

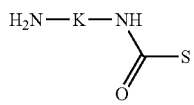

in a solvent, such as acetonitrile, to yield

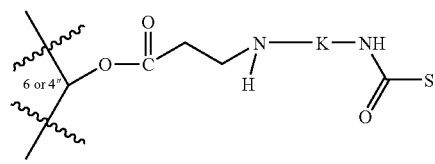

The derivatized steroid (i.e., S—C(O)—NH—K—$NH_2$) may be formed by reacting an appropriate amine (having the linkage group —K—$NH_2$) with a carboxylic acid group or an ester group of a steroid according to Formula V.

d) Compounds represented by Formula I, where $X^2$ is —NH—, can be prepared by reacting a macrolide subunit and a derivatized steroid subunit having a free amino group as shown below.

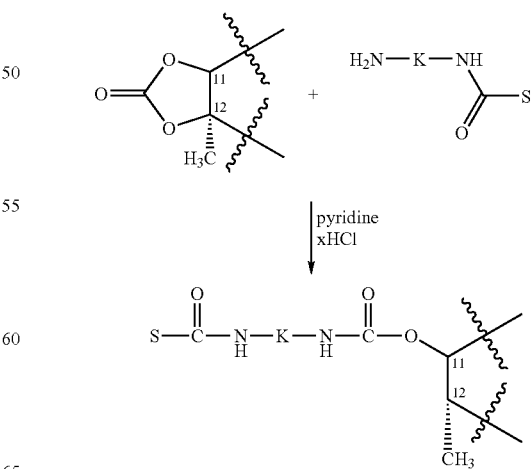

e) Compounds represented by Formula I, where $X^2$ is —NH—, can be prepared by reacting a macrolide subunit and a steroid subunit having a free carboxylic acid group as shown below.

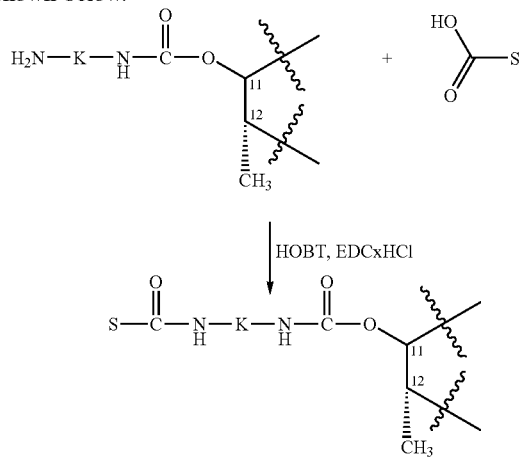

↓ HOBT, EDCxHCl

The reactant macrolide subunit can be formed by oxidizing the corresponding macrolide having a hydroxy substituent at the 4" position on cladinose sugar to obtain a =O substituent at the 4" position, converting the

at the 4" position to an epoxy group

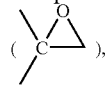

and cleaving the epoxy group with an appropriate reactant(s) to yield the reactant macrolide subunit (M-O—C(O)—NH—K—NH$_2$).

f) Compounds of Formula I can be prepared by reacting a macrolide subunit having a leaving group $L^2$ (such as Br), and a steroid as shown below.

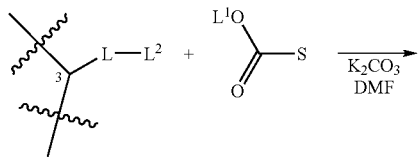

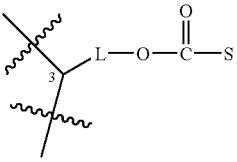

The starting macrolide subunit can be prepared by cleaving the sugar group attached at the 3-position of the macrolide ring and then reacting the macrolide with a reagent of Formula $L^2$-L-$L^1$, where $L^2$ is a leaving group.

g) Compounds of Formula I can be prepared by reacting a macrolide subunit having a leaving group $L^2$ (such as Br), and a steroid as shown below.

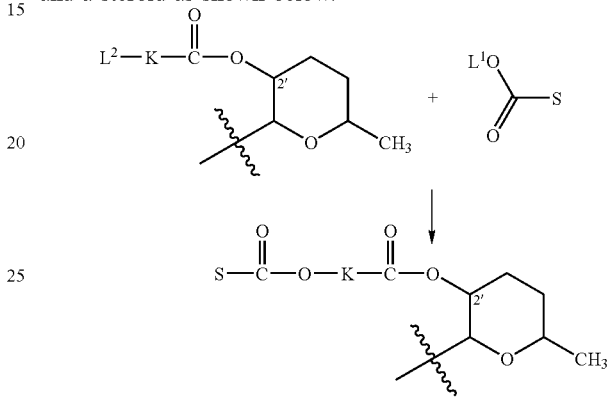

The salts of the compounds represented by Formula I may be prepared by applying generally known procedures such as, e.g., a reaction of the compounds of the structure I with a corresponding base or acid in a suitable solvent or mixture of solvents e.g. ethers (diethyl ether) or alcohols (ethanol, propanol or iso-propanol).

The 16-membered ring macrolides are traditionally divided into sub-families based upon the substitution patterns of their aglycones. The principal prototypes of this family can be represented by leucomycin, spiramycin and tylosin.

Tylosin is a representative of 16-membered macrolides, which possesses a highly substituted aglycone with two double bonds (tylonolide) and a third saccharide substituent (β-D-mycinose) in addition to the disaccharide attached to the 5-hydroxyl group. Hydrolysis of mycarose from disaccharide yielded desmycarosyl-tylosin (desmycosin).

Potential sites of modification in desmycosin:

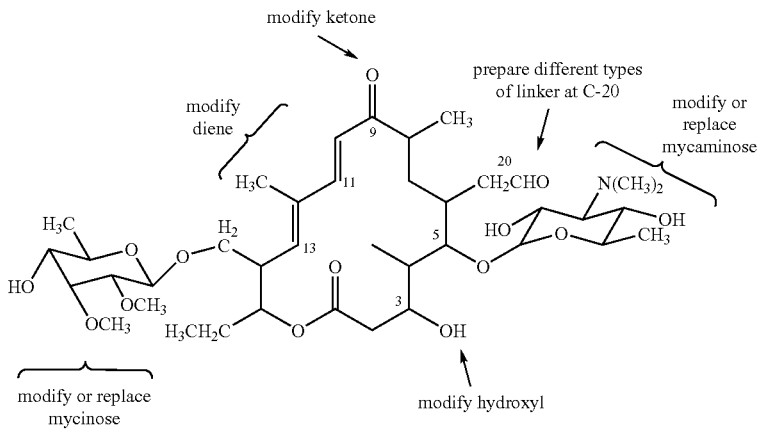

For example, 16-membered ring macrolide hybrid could be prepared by reductive amination of the C-20 aldehyde group.

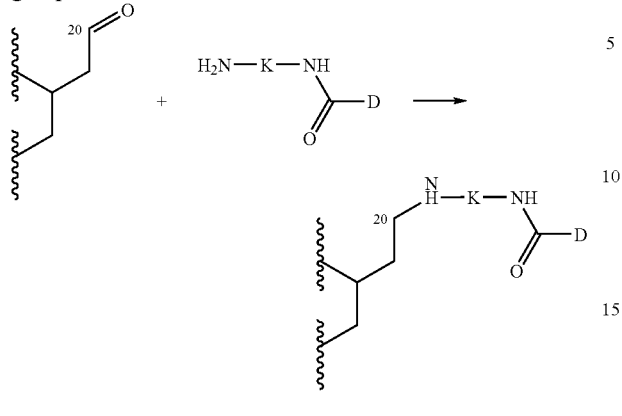

This reaction could be used also for 17-membered azalides like 8a-aza-homodesmycosins and its derivatives (such as di- and tetrahydro derivatives).

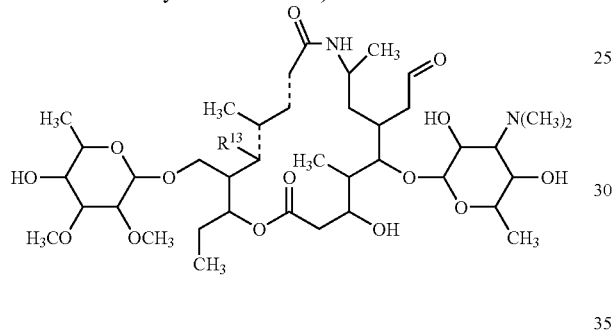

- - - represents a single or double bond $R^{13}$ is hydrogen or hydroxy

Alternatively, 16-membered ring macrolide derivatisation can proceed by transforming double bonds (e.g., by epoxidation), and cleaving the epoxy group with an appropriate reactant (such as a diamine) to yield the reactant macrolide subunit (M—O—C(O)—NH—K—$NH_2$).

Also a ketone in position 9 may be modified by hydroxylamine hydrochloride to yield oxime and then reduced to amine.

If the steroid is an —S(O)$_n$—$R_C$ at position 17, the same linkage schemes can be used.

The steroid subunit may be linked to the macrolide through the 21 hydroxy group in steroids that have such a group. Begining with a 21-hydroxy steroid cyclic ketal is reacted with an appropriate carboxylic acid halide or an anhydride, preferably in a solvent such as methylene chloride in the presence of a tertiary amine base or pyridine at a reduced temperature (-50 C-300 C). The intermediate so produced is reacted with $H_2$N-L-M to form compounds of Formula I

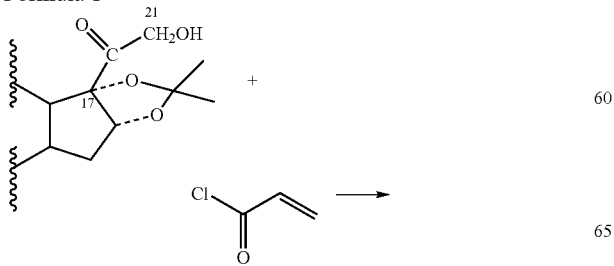

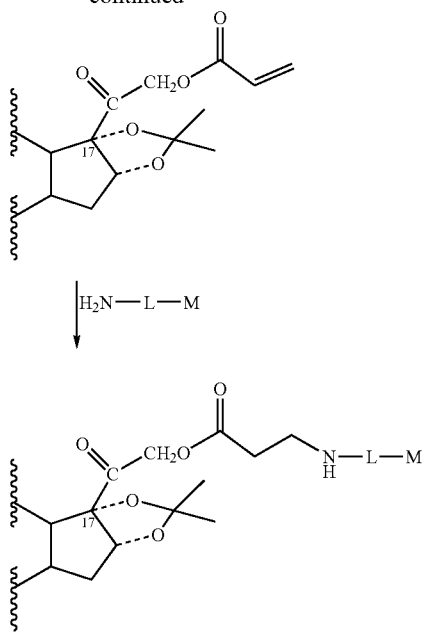

The steroid subunit may also be linked to the macrolide through the 17 position on the steroid subunit. One method for preparing such a compound is as follows:

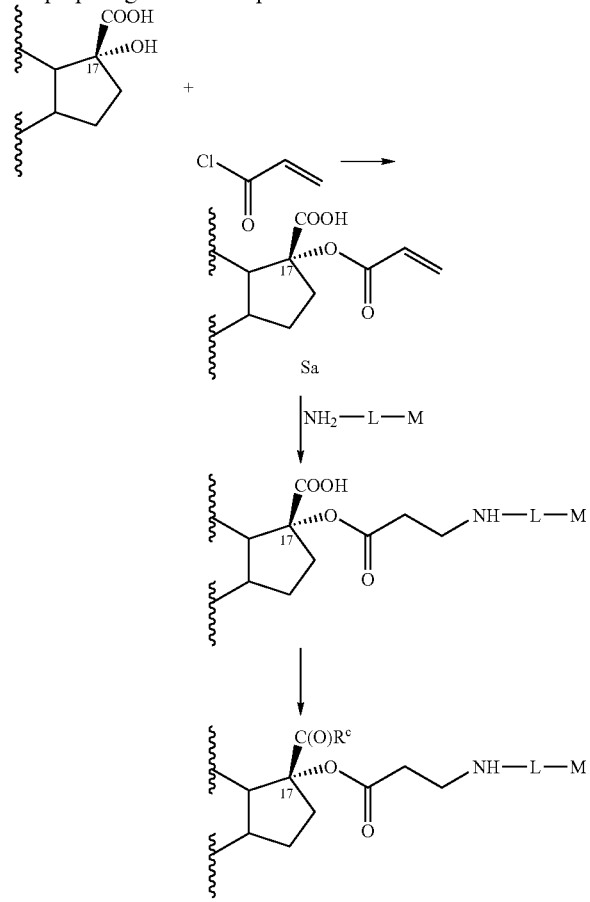

For example, when L is —K—NH— (wherein K is the portion of the L molecule attached to the macrolide) the compound of Formula I can be formed by derivatizing an NH group on the macrolide ring to an —N—K—($NH_2$)— group and reacting the derivatized macrolide with a steroid anti-inflammatory subunit represented by Formula Sa:

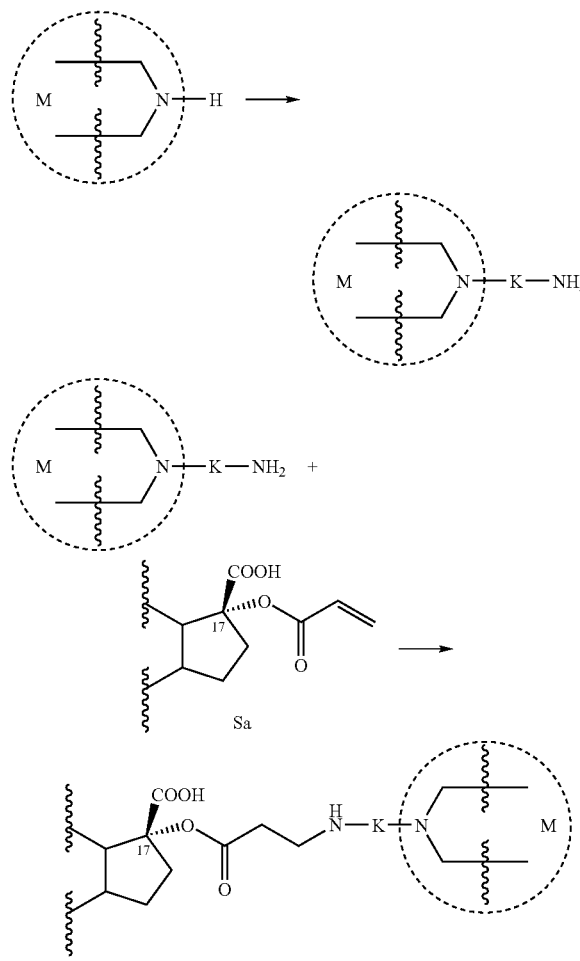

This process may also be performed when the NH group in the macrolide is attached at the 3' position of a sugar ring $S^1$ (i.e., a desozamine sugar) of the macrolide:

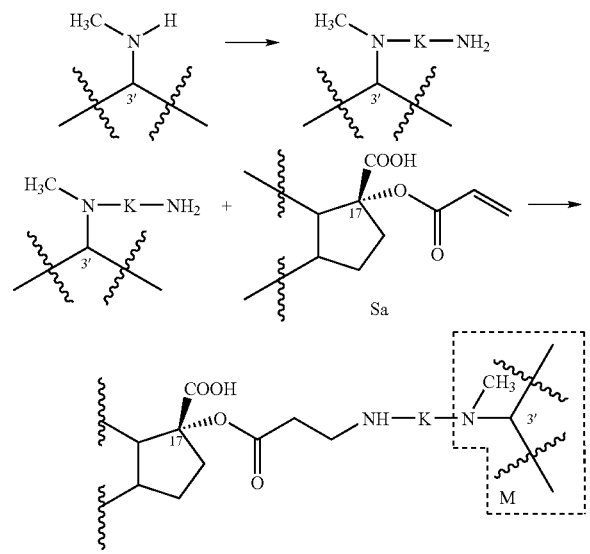

or the 4" position of the sugar ring $S^2$:

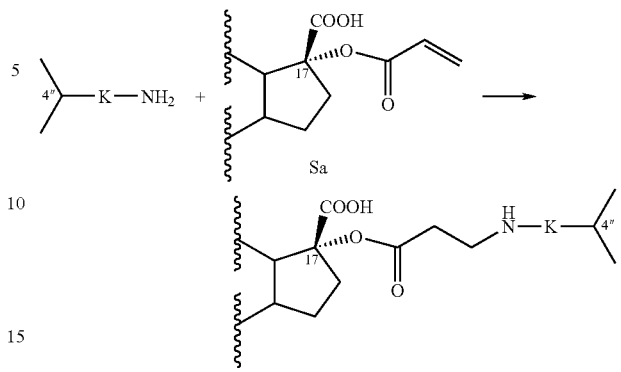

Compounds represented by Formula I, where $X^2$ is —NH—, can be prepared by reacting a macrolide subunit and a steroid subunit having a —C=C— bond as shown below.

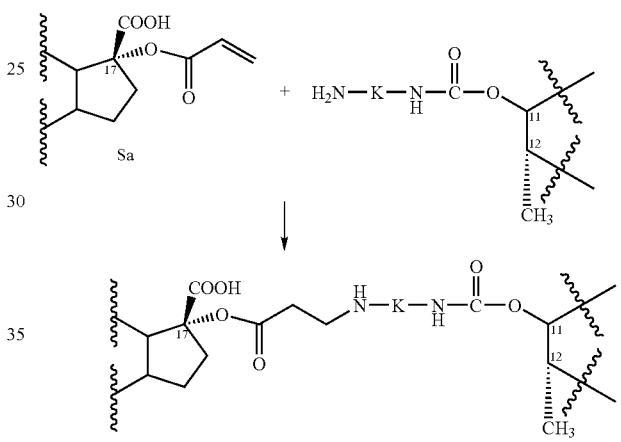

The carboxylic acid group at the 17 position of the starting steroid subunit may be modified prior to the reaction with $NH_2$-L-M.

The carboxylic acid group at the 17 position of the starting steroid subunit can also be protected prior to the reaction with $NH_2$-L-M and deprotected after the reaction with $NH_2$-L-M or the esterification step.

A further aspect of the present invention relates to the methods for using the compounds of Formula I as anti-inflammatory, anti-anaphylactic and immunomodulating agents which can be administered in different ways, depending on the inflammation site. Further, the present invention relates to pharmaceutical compositions containing an effective dose of compounds of the present invention as well as pharmaceutically acceptable excipients, such as carriers or diluents.

The preparation of the pharmaceutical compositions of the invention can include mixing, granulating, tabletting and dissolving the ingredients. Chemical carriers can be in solid or liquid form. Solid carriers can be lactose, sucrose, talc, gelatine, agar, pectin, magnesium stearate, fatty acids without limitation. Liquid carriers can be syrups, oils such as olive, sunflower seed or soybean oils, water, or physiologic saline without limitation. Similarly, carriers may also contain a component for a sustained release of the active component such as glyceryl monostearate or glyceryl distearate. Several forms of pharmaceutical compositions can be prepared. If a solid carrier is used, these forms can include tablets, caplets, solid gelatinous capsules, powders or granules without limitation that can be administered orally. The amount of the solid carrier can vary but mainly it is in the range from 25 mg to 1 g. If a liquid carrier is used, the formulation can be in the form of a syrup, emulsion, soft gelatinous capsules, or sterile injectable liquids, or nonaqueous liquid suspensions topically or systemically, e.g., orally, parenterally, percutaneously, mucosally, e.g., buccally, intranasally, intrarectally and intravaginally. "Parenterally" means by intravenous, intramuscular or subcutaneous route. The corresponding preparations of the compounds of the present invention can be used in the prophylaxis as well as in the therapeutic treatment (prevention, delay, inhibition or relief) of several disorders (diseases and other pathological inflammatory conditions) caused by or associated with an abnormal or undesirable (excessive, nonregulated, or dysregulated) inflammatory immune response involving the production of inflammatory cytokines or other inflammation mediators, including without limitation TNF-$\alpha$ and IL-1$\beta$. These disorders include autoimmune diseases such as rheumatoid arthritis, insulin-dependent diabetes mellitus, autoimmune thyroiditis, multiple sclerosis, uveoretinitis, lupus erythematosus, scleroderma; other arthritic conditions having an inflammatory component such as rheumatoid spondylitis, osteoarthritis, septic arthritis and polyarthritis; other inflammatory brain disorders, such as meningitis, Alzheimer's disease, AIDS dementia encephalitis, other inflammatory eye inflammations, such as retinitis; inflammatory skin disorders, such as, eczema, other dermatites (e.g., atopic, contact), psoriasis, burns induced by UV radiation (sun rays and similar UV sources); inflammatory bowel disease, such as Crohn s disease, ulcerative colitis; asthma; other allergy disorders, such as allergic rhinitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, chronic obstructive pulmonary disease, congestive heart failure, Type II diabetes, lung fibrosis, vascular disease, such as atherosclerosis and restenosis; and alloimmunity leading to transplant rejection. The compounds can also be administered by inhalation when application within the respiratory tract is intended. A further object of the present invention relates to the preparation of various pharmaceutical forms of the compounds to achieve the optimal bioavailability of the active compound of Formula I.

For percutaneous or mucosal external administration, the compound of Formula I can be prepared in a form of an ointment or cream, gel or lotion. Ointments, creams and gels can be formulated using a water or oil base with addition of an appropriate emulsifier or gelling agent Formulation of the present compounds is especially significant for respiratory inhalation, wherein the compound of Formula I is to be delivered in the form of an aerosol under pressure. It is preferred to micronize the compound of Formula I after it has been homogenised, e.g., in lactose, glucose, higher fatty acids, sodium salt of dioctylsulfosuccinic acid or, most preferably, in carboxymethyl cellulose, in order to achieve a microparticle size of 5 $\mu$m or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., Thorax, 1985, 40:61–676 Berenberg, M., J. Asthma USA, 1985, 22:87–92. A Bird nebulizer can also be used. See also U.S. Pat. Nos. 6,402,733; 6,273,086; and 6,228,346.

The compound of the structure I for inhalation is preferably formatted in the form of a dry powder with micronized particles, as described herein.

The compound can also be incorporated into a formulation for treating inflammation localized in an organ or tissue, e.g., Crohn's disease, where it can be administered orally or rectally. Formulations for oral administration can incorporate excipients enabling bioavailability of the compound at the site of inflammation. This can be achieved by different combinations of enteric and delayed release formulations. The compound of Formula I can also be used in the treatment of Crohn's disease and intestinal inflammation disease if the compound is applied in the form of a clyster, for which a suitable formulation can be used, as is well known in the field.

A further aspect of the present invention relates to the use of compounds of Formula I in the treatment of inflammatory diseases, disorders and conditions characterized by or associated with an undesirable inflammatory immune response, especially of all diseases and conditions induced by or associated with an excessive secretion of TNF-$\alpha$ and IL-1.

A therapeutically effective amount of the compound of the present invention can be determined by methods known in the art. Since the compound of the present invention is more efficiently delivered to the desired site than the corresponding anti-inflammatory steroid drug alone, a lesser amount of the compound on a molar basis than of the steroid anti-inflammatory drug can be administered while still achieving the same therapeutic effect. Furthermore, since administration of the compound results in fewer side effects than with the corresponding steroid anti-inflammatory drug, the steroid amount can be increased. Thus, the table below serves only as a guide. A threshold therapeutically effective amount of the compound, a pharmaceutically salt thereof, a solvate thereof, or a prodrug thereof is generally equal to or less than a therapeutically effective amount of the nonsteroidal anti-inflammatory drug on a molar basis. Broad and preferred effective amounts of the compound, a pharmaceutically salt thereof, a solvate thereof, or a prodrug thereof are shown in the table below.

| | Amount of Compound, Pharmaceutically Acceptable Salt Thereof, Solvate Thereof, or Prodrug Thereof | |
| --- | --- | --- |
| | mg/kg body weight/day of the steroid (had it been administered alone) | $\mu$mol/kg body weight/day of the hybrid or the steroid |
| Broad | from about 0.001 to about 1000 | from about 0.004 to about 4000 |
| Preferred | from about 0.01 to about 100 | from about 0.04 to about 400 |
| More Preferred | from about 1 to about 100 | from about 4 to about 400 |
| Most Preferred | from about 3 to about 30 | from about 12 to about 120 |

For example, if the preferred amount range for prednisone is 1–50 mg/day, this corresponds to a range of 2.79 $\mu$mol to 139.5 $\mu$mol per day. The starting amount range for a hybrid steroid-macrolide conjugate according to the invention will be also 2.79 $\mu$mol to 139.5 $\mu$mol of conjugate per day. This dosage can be fine-tuned in light of the present specification using the ordinary skill in the act.

The efficacy of the present compounds can be assessed by any method for assessing inflammation or anti-inflammatory effect. There are many known methods for this purpose including without limitation use of contrast ultrasound in conjunction with injection of microbubbles, measurement of inflammatory cytokines (such as TNF-α, IL-1, IFN-γ) measurement of activated immune system cells (activated T cells, cytotoxic T cells specifically recognizing the inflamed or transplanted tissue) as well as by observation (reduction of oedema reduction of erythema, reduction of pruritus or burning sensation, reduction of body temperature, improvement in function of the afflicted organ) as well as any of the methods provided below as well as any of the methods provided below.

The therapeutic effect of compounds of the present invention was determined in in vitro and in vivo experiments such as the following.

The beneficial antiinflammatory effect of the compounds of the present invention was determined in the following in vitro and in vivo experiments:

Assay of Binding to Human Glucocorticoid Receptor

The gene for the alpha isoform of human glucocorticoid receptor (EMBL Acc. No. M10901) was cloned by reverse polymerase chain reaction. The total RNA was isolated from human peripheral blood lymphocytes according to the instructions of the manufacturer (Qiagen), transcripted into cDNA with AMV reverse transcriptase (Roche) and the gene was multiplied by specific primers 1) 5'ATATGGATCCCTGATGGACTCCAAA-GAATCATTAACTCC3' and 2) 5'ATATCTCGAGGGCAGTCACTTTTGAT-GAAACAGAAG3'. The reaction product obtained was cloned into the XhoI/BamHI site of Bluescript KS plasmid (Stratagene), subjected to sequencing by the dideoxy fluorescent method with M13 and M13rev primers (Microsynth) and then it was cloned into the XhoI/BamHI site of pcDNA3.1 hygro(+)plasmid (Invitrogen Life Technologies). $1 \times 10^5$ COS-1 cells were seeded onto a 12-well plate (Falcon) in DMEM medium (Invitrogen Life Technologies) with 10% FBS (Biowhitaker) and cultivated to a 70% confluence at 37° C. in an atmosphere with 5% $CO_2$. The medium was removed and 1 μg of DNA, 7 μl of PLUS reagent and 2 μl of Lipofectamine (Life Technologies) in 500 μl DMEM were added per well. The cells were incubated at 37° C. in an atmosphere with 5% $CO_2$ and after 5 hours the same volume of 20% FBS/DMEM was added. After 24 hours, the medium was completely changed. 48 hours after transfection, the test compounds in different concentrations and 24 nM [$^3$H]dexamethasone (Pharmacia) in DMEM medium were added. The cells were incubated for 90 minutes at 37° C. in an atmosphere with 5% $CO_2$, washed three times with PBS buffer (Sigma) cooled to 4° C. (pH= 7.4) and then lysed in Tris buffer (pH=8.0) (Sigma) with 0.2% SDS (Sigma). After the addition of UltimaGold XR (Packard) scintillation liquid, the residual radioactivity was read in a Tricarb (Packard) β-scintillation counter.

Assay of Inhibition of Mouse T-cell Hybridoma 13 Proliferation as a Result of Apoptosis Induction In a 96-well plate, triplicates of test steroid dilution in RPMI medium (Instituted of Immunology, Zagreb) with 10% FBS were performed. To the solutions of compounds, 20000 cells per well were added and incubated overnight at 37° C. in an atmosphere with 5% $CO_2$, then 1 μCi of [$^3$H]thymidine (Pharmacia) was added and the mixture was incubated for additional 3 hours. The cells were harvested by applying a vacuum over GF/C filter (Packard). Onto each well, 30 μl of Microscynt 0 scintillation liquid (Packard) was added and the incorporated radioactivity was measured on a β-scintillation counter (Packard). The specificity of apoptosis induction by glucocorticoids was proven by antagonising the proliferation inhibition with mifepristone (Sigma).

Balb/c mice are sacrificed by thiopental injection (Pliva Inc.). Spleens are gently sliced and minced on cell strainer. Mononuclear cells are separated by centrifugation using Histopaque 1083 (Sigma diagnostics, Cat No 1083-1) on 400 g. Cells are washed with RPMI medium (Institute of immunology, Zagreb, Croatia), and adjusted to $4 \times 10^6$ cells/ml in RPMI medium supplemented with 10% FBS (Invitrogen). Compounds are diluted to appropriate concentrations ranging from $10^{-5}$M to $10^{-10}$M in RPMI with 10% FBS, and each dilution (100 ul) is set in triplicate in 96 well plate. Positive and negative control contained 100 ul of RPMI with 10% FBS. 50 ul of murine splenocytes are added on each well, and 50 ul of concanavalin A (Sigma, cat No C5275), 20 ug/ml in RPMI with 10% FBS in all wells except in negative control where 50 ul of RPMI with 10% FBS is added.

Plates are placed in incubator (37° C., 90% relative humidity, 5% $CO_2$) for 72 hours, and frozen at −70° C. until determination of interleukins.

Interleukins are determined by using sandwich ELISA, using capture and detection antibodies (R&D), according to manufacturer's recommendations.

Model of Lung Eosinophilia in Mice

Male Balb/C mice with a body weight of 20–25 g were randomly divided into groups, and sensitized by an i.p. injection of ovalbumin (OVA, Sigma) on day zero and day fourteen. On the twentieth day, the mice were subjected to a challenge test by i.n. (intranasal) application of OVA (positive control or test groups) or PBS (negative control). 48 hours after i.n. application of OVA, the animals were anaesthetized and the lungs were rinsed with 1 mL of PBS. The cells were separated on Cytospin 3 cytocentrifuge (Shandon). The cells were stained in Diff-Quick (Dade) and the percentage of eosinophils was determined by differential counting of at least 100 cells.

Fluticasone and beclomethasone were used as standard anti-inflammatory substances.

The compounds were administered daily i.n. or i.p. in different doses 2 days before the provocative test and up to the completion of the test. Compounds were administered as suspension either in carboxymethyl cellulose or in lactose solution.

Model of Corticosterone Suppression and Thymus Size Reduction in Rats

Male Wistar rats with a body weight between 200 and 250 g were randomly divided. Tested compounds and standard glucocorticoids were applied by s.c. route once a day for three days. On day three, rats were subjected to cold stress (4° C., for one hour), anesthesized with Thiopenetal (Pliva Inc.) and blood was taken on heparin. The complete thymus was removed from each animal, and weighed immediately. Plasma was stored at −70° C. until assayed. Corticosterone was extracted with chloroform (5 mL) from 1 mL plasma, or from corticosterone standard dilutions in PBS, intereferent compounds were washed with 0.1 M NaOH, and sulfuric acid:$H_2O$:$C_2H_5OH$=8:2:1 was added. Fluorescence was measured 60 minutes later, excitation/emission wavelength was 470/530.

Compounds were considered active if they demonstrated a statistically significant (by Student's t-test, $p<0.05$) result in at least two of the foregoing tests. The molar amounts of compound used were below the threshold amount of macrolide (above 30 μm) for exerting a mild anti-inflammatory effect as reported in the literature.

Uptake/Release Assay on RAW 264.7, Caco-2 and RBL-2H3 Cell Line

Cells were seeded in 6 well plate and reached full confluency with $5 \times 10^5$ cell per plate. Radiolabelled compounds (app. 50 mCi/mmol each) were loaded on cells in 10 μM concentration. Cells were incubated for 2 hours and washed with cold PBS. Cellular concentration was determined immediately by scintillation counting, or were left for another hour with fresh, compound free medium to determine compound release.

SYNTHETIC METHODS AND EXAMPLES

Preparation of Intermediates

Method A a) The intermediate P1 (1.684 g; 2.435 mmole) was dissolved in 50 mL of acrylonitrile and the solution was refluxed at 100° C. for 9 hours. Then it was evaporated under reduced pressure and 1.54 g of the raw product A1 was obtained.

In accordance with the same procedure and starting from the macrolide P2 (Table 1), nitrile A2 is obtained. The characteristics of nitrile A1 and A2 are given in Table 1.

b) Amine A3 is obtained starting from the macrolide A1 (Table 1) by hydrogenation with $H_2$ with $PtO_2$.

The macrolide A1 (1.54 g; 2 mmole) was dissolved in 50 mL of absolute ethanol and hydrated in a reactor with the catalyst $PtO_2$ (263 mg) under pressure of 40 atm for 24 hours. The reaction mixture was filtered and the solvent was evaporated under reduced pressure. 1.34 g of the mixture was obtained, the mixture was purified on a silica gel column, eluent $CHCl_3$:MeOH:$NH_4OH$=6:1:0.1; 508 mg of amine A3 was obtained.

In accordance with the same procedure, starting from nitrile A2, amine A4 is obtained.

The characteristics of the macrolides A3 and A4 are given in Table 1.

Method B a) The compound P3 (1.95 g; 2.52 mmole) was dissolved in 90 mL of methanol. 1.71 g (12.61 mmole) of $NaOAc \times 3H_2O$ and 0.68 g (2.64 mmole) of $I_2$ were added. The reaction mixture was illuminated with a 500W halogen lamp for 2 h. Subsequently, 2–3 drops of 0.1 M $Na_2S_2O_3$ were added. The solvent was evaporated under reduced pressure and the residue was dissolved in ethyl-acetate and washed with water and with saturated $NaHCO_3$ solution. The organic layer was dried over anhydrous $Na_2SO_4$ and evaporated in a rotary evaporator. 3.2 g of the macrolide B1 was isolated.

b) The compound B1, 1.98 g (2.52 mmole), was dissolved in 90 mL of methanol. Subsequently, 3.67 mL (21.09 mmole) of disopropylethylamine and 4.95 mL of ethyliodide were added to the solution. The reaction mixture was stirred at 50° C. overnight. The solvent was then evaporated under reduced pressure and the residue dissolved in ethylacetate and washed with saturated $NaHCO_3$ solution and water. The organic layer was dried over anhydrous $Na_2SO_4$ and evaporated. The mixture was purified on a silica gel column in the solvent system $CHCl_3$:MeOH:$NH_4OH$=6:1:0.1. 559 mg of the compound B2 was isolated.

c) In 5 mL of 1,4-diaminobutane, 650 mg (0.82 mmole) of compound B2 was dissolved. Then, 95 mg (0.82 mmole) of pyridine hydrochloride was added to the solution. The reaction mixture was stirred at room temperature for 3 days. The product was extracted by dichloromethane and washed with water and the organic layer was subsequently dried over $Na_2SO_4$ and the solvent evaporated under reduced pressure. After purification of the mixture on a silica gel column in the solvent system $CHCl_3$:MeOH:$NH_4OH$=6:1:0.1, 300 mg of the amine B3 was obtained.

According to the same procedure, starting from the macrolide P3 and diaminobutane, the macrolide B4 is obtained.

The characteristics of the compounds B1 to B4 are given in Table 1.

Method C a) A suspension of steroid S1 (110 mg; 0.29 mmole) in dry $CH_2Cl_2$ (5 mL) cooled to 0° C. under argon, was added to 0.380 mL (2.73 mmole) of triethylamine; 80 mg (0.59 mmole) of 1-hydroxybenzotriazole; 230 mg (0.29 mmole) of the amine A4 and 235 mg (1.23 mmole) of 1-(3-dimethylaminopropyl)-3-ethyl-carbodiimide hydrochloride. The reaction mixture was stirred at room temperature in a flow of argon for 24 hours and then evaporated to a smaller volume and purified on a silica gel column (eluent: $CHCl_3$:$CH_3OH$:$NH_4OH$=6:1:0.1). 224 mg of the compound C1 was obtained.

According to a similar procedure, from the macrolide A4 and the steroid S2, the compound C2 is obtained, from the compound B4 and the steroid S2 the compound C3, and from the macrolide A4 and the steroid S4 the compound C4.

The characteristics of compounds C1 to C4 are given in Table 1.

TABLE 1

| Com. | M | $R^1$ | $R^2$ | $R^3$ | $R^4$ | S | Molecular formula | $MH^+$ |
|---|---|---|---|---|---|---|---|---|
| P1 | M1 | H | H | H | H | — | $C_{35}H_{65}NO_{12}$ | 692.9 |
| P2 | M2 | H | H | H | $N(CH_3)_2$ | — | $C_{37}H_{70}N_2O_{12}$ | 735.4 |
| P3 | M3 | $CH_3$ | | III | $N(CH_3)_2$ | — | $C_{39}H_{70}N_2O_{13}$ | 775.5 |
| A1 | M1 | $(CH_2)CH CN$ | H | H | H | — | $C_{38}H_{68}N_2O_{12}$ | 745.8 |
| A2 | M2 | $(CH_2)CH CN$ | H | H | $N(CH_3)_2$ | — | $C_{40}H_{73}O_{12}N_3$ | 789.0 |
| A3 | M1 | L1 | H | H | H | — | $C_{38}H_{72}N_2O_{12}$ | 749.6 |
| A4 | M2 | L1 | H | H | $N(CH_3)_2$ | — | $C_{40}H_{77}O_{12}N_3$ | 793.0 |
| B1 | M3 | $CH_3$ | | III | $NHCH_3$ | — | $C_{39}H_{69}N_2O_{13}$ | 761.5 |
| B2 | M3 | $CH_3$ | | III | $N(CH_3)C_2H_5$ | — | $C_{40}H_{72}N_2O_{13}$ | 789.5 |
| B3 | M3 | $CH_3$ | L2 | H | $N(CH_3)C_2H_5$ | — | $C_{44}H_{94}N_4O_{13}$ | 877.6 |
| B4 | M3 | $CH_3$ | L2 | H | $N(CH_3)_2$ | — | $C_{43}H_{92}N_4O_{13}$ | 863.8 |
| C1 | M2 | L1 | H | H | $N(CH_3)_2$ | S1 | $C_{61}H_{102}FN_3O_{16}$ | 1152.6 |

TABLE 1-continued

| Com. | M | $R^1$ | $R^2$ | $R^3$ | $R^4$ | S | Molecular formula | $MH^+$ |
|---|---|---|---|---|---|---|---|---|
| C2 | M2 | L1 | H | H | $N(CH_3)_2$ | S2 | $C_{61}H_{101}F_2N_3O_{16}$ | 1170.6 |
| C3 | M3 | $CH_3$ | L2 | H | $N(CH_3)_2$ | S2 | $C_{64}H_{106}F_2N_4O_{17}$ | 1241.7 |
| C4 | M2 | L1 | H | H | $N(CH_3)_2$ | S4 | $C_{61}H_{102}FN_3O_{15}$ | 1136.7 |

L1 = —$(CH_2)_3$—$NH_2$
L2 = —C(O)NH—$(CH_2)_4$—$NH_2$

M1–M3 corresponds to the macrolide subunit of the formula immediately preceeding the foregoing table wherein the variables R1–R4 are as specified in Table 1.

TABLE 2

| S | $R^a$ | $R^b$ | $R^d$ | Molecular formula | $MH^+$ | $MH^-$ |
|---|---|---|---|---|---|---|
| S1 | F | H | OH | $C_{21}H_{27}FO_5$ | 378.9 | — |
| S2 | F | F | OH | $C_{21}H_{26}O_5F_2$ | 397.4 | 395.3 |
| S3 | Cl | F | OH | $C_{21}H_{26}O_5ClF$ | — | 411.3 |
| S4 | F | H | H | $C_{21}H_{27}FO_4$ | — | 361.2 |

Example 1

Compound 1: I; M=M1, L=L1, S=S1; ($R^2=R^3=R^4=H$, $X^1$=—$CH_2$—; m=2, $X^2$=—NH—, $R^a$=F, $R^b$=H, $R^d$=OH)

In 5 mL of dry dichlormethane, 76 mg of the steroid S1 (0.2 mmole) was dissolved in an inert atmosphere. Subsequently, 0.25 mL of triethylamine, 53 mg of hydroxybenzotriazole, 150 mg of the macrolide A3 (0.2 mmole) and 157 mg of 1-(3-dimethylaminopropyl)-3-ethylcarbodiimide hydrochloride was added to the solution. The reaction mixture was stirred at room temperature overnight. The solvent was evaporated under reduced pressure. The mixture obtained was purified on a silica gel column, eluent $CHCl_3$:MeOH:$NH_4$OH=6:1:0.1. 167 mg of the compound 1 was obtained; MS (m/z): 1109.7 [MH]$^+$. IR(cm$^{-1}$)/KBr: 3425, 2974, 2939, 2875, 1721, 1665, 1627, 1525, 1459, 1379, 1296, 1262, 1168, 1125, 1064, 1035, 1013, 959, 927, 894, 804.

Example 2

Compound 2: I, M=M1, L=L1, S=S2; ($R^2=R^3=R^4=H$, $X^1$=—$CH_2$—, m=2, $X^2$=—NH—, $R^a=R^b$=F, $R^d$=OH)

In 5 mL of dry dichlormethane, 80 mg of the steroid S2 (0.2 mmole) was dissolved in an inert atmosphere. Subsequently, 0.25 mL of triethylamine, 53 mg of hydroxybenzotriazole, 150 mg of the macrolide A3 (0.2 mmole) and 157 mg of 1-(3-dimethylaminopropyl)-3-ethylcarbodiimide hydrochloride was added to the solution. The reaction mixture was stirred at room temperature overnight. The solvent was evaporated under reduced pressure and the mixture obtained was purified on a silica gel column, eluent $CHCl_3$:MeOH:$NH_4$OH=6:1:0.1. 129 mg of the compound 2 was obtained; MS (m/z): 1127.7 [MH]$^+$. IR(cm$^{-1}$)/KBr: 3424, 2972, 2939, 2876, 1719, 1670, 1631, 1560, 1523, 1458, 1379, 1317, 1264, 1167, 1127, 1064, 1033, 997, 960, 900, 820, 735, 709.

Example 3

Compound 3: I; M=M1, L=L1, S=S3; ($R^2=R^3=R^4=H$, $X^1$=—$CH_2$—, m=2, $X^2$=—NH—, $R^a$=Cl, $R^b$=F, $R^d$=OH)

80 mg of the steroid S3 (0.19 mmole) was dissolved in 5 mL of dry dichlormethane in an inert atmosphere. 0.25 mL of triethylamine, was added to the solution, which became clear. Subsequently, 53.5 mg of hydroxybenzotriazole, 145 mg of the macrolide A3 (0.19 mmole) and 157 mg of 1-(3-dimethylaminopropyl)-3-ethylcarbodiimide hydrochloride were added. The reaction mixture was stirred at room temperature overnight. The solvent was evaporated under reduced pressure and the obtained mixture was purified on a silica gel column, eluent $CHCl_3$:MeOH:$NH_4$OH= 6:1:0.1. 200 mg of the compound 3 was obtained; MS (m/z): 1143.6 [MH]$^+$. IR(cm$^{-1}$)/KBr: 3423, 2971, 2937, 2876, 1719, 1668, 1630, 1561, 1523, 1459, 1379, 1319, 1262, 1168, 1125, 1064, 998, 959, 901, 819, 756.

Example 4

Compound 4: I; M=M3, L=L2, S=S1; (R1=$CH_3$, $R^3$=H, $R^4$=N($CH_3$)$CH_2CH_3$, $X^1$=—C(O)NH—, m=4, $X^2$=— NH—, $R^a$=F, $R^b$=H, $R^d$=OH).

In 15 mL of dichloromethane, 126 mg (0.33 mmole) of the compound S1 was dissolved. To the reaction mixture were added, 0.363 mL of triethylamine, 90 mg of hydroxybenzotriazole, 292 mg (0.33 mmole) of the compound B3 and 229 mg of 1-(3-dimethylaminopropyl)-3-ethylcarbodiimide hydrochloride. The reaction mixture was stirred at room temperature in an inert atmosphere for 24 h. The solvent was then evaporated, and the compound was purified on a silica gel column in the solvent system $CHCl_3$:MeOH:$NH_4$OH=6:1:0.1. 58 mg of the compound 4 was isolated: MS (m/z): 1237.8 [MH]$^+$. IR(cm$^{-1}$)/KBr:3437, 2973, 2938, 1723, 1658, 1545, 1526, 1462, 1379, 1271, 1172, 1111, 1053, 996, 895, 807.

Example 5

Compound 5: I; M=M2, L=L1, S=S1; ($R^2=R^3$=H, $R^4$=NH$CH_3$, $X^1$=—$CH_2$—, m=2, $X^2$=—NH—, $R^a$=F, $R^b$=H, $R^d$=OH)

Procedure 1:

In 3 mL of methanol, 100 mg of the compound C1 (0.086 mmole) was dissolved. To the solution, 59 mg of sodiumacetate trihydrate and 23 mg of iodine was added. The reaction mixture was illuminated with a 500W halogen lamp for 2 hours. Subsequently, a couple of drops of 1M sodiumthiosulphate were added. The solvent was evaporated under reduced pressure. The obtained mixture was purified on a silica gel column with, eluent $CHCl_3:MeOH:NH_4OH=$ 6:1:0.1. 21 mg of the compound 5 was obtained; MS (m/z): 1138,5 $[MH]^+$. $IR(cm^{-1})/KBr$: 3423, 2972, 2938, 2875, 1719, 1664, 1625, 1560, 1541, 1523, 1459, 1379, 1243, 1169, 1125, 1072, 1012, 959, 894, 807, 755.

Procedure 2:

The compound C1 (500 mg; 0.43 mmole) was dissolved in 30 mL of acetonitrile. Subsequently, 146 mg of N-iodine succinimide (0.65 mmole) at 0° C. and in a flow of argon was added to the solution. The reaction mixture was heated to room temperature and stirred for 5 hours. Subsequently, the mixture was diluted with 100 mL of dichlormethane and extracted with 100 mL of 1:1 5% $NaHSO_3:Na_2CO_3$ and saturated NaCl solution. The organic layer was dried over anhydrous sodium-sulphate. The solvent was evaporated in a rotary evaporator. The obtained mixture was purified on a silica gel column, eluent $CHCl_3:MeOH:NH_4OH=6:1:0.1$. 155 mg of the compound 5 was obtained; MS (m/z): 1139.3 $[MH]^+$.

Example 6

Compound 6: I; M=M2, L=L1, S=S2; ($R^2=R^3=H$, $R^4=NHCH_3$, $X^1=$—$CH_2$—, m=2, $X^2=$—NH—, $R^a=R^b=F$, $R^d=OH$)

The compound C2 (250 mg; 0.21 mmole) was dissolved in 10 mL of methanol. To the solution was added, 145 mg of sodiumacetate trihydrate (1 mmole) and 57.4 mg of iodine (0.22 mmole). The reaction mixture was illuminated with a 500W halogen lamp for 2 hours. Several drops of 1M sodium-thiosulphate were added in order to destroy the surplus iodine. The solvent was evaporated under reduced pressure. The obtained mixture was purified on a silica gel column, eluent $CHCl_3:MeOH:NH_4OH=6:1:0.1$. 83 mg of the compound 6 was obtained; MS (m/z): 1156.7 $[MH]^+$. $IR(cm^{-1})/KBr$: 3432, 2972, 2938, 2876, 1774, 1719, 1670, 1655, 1578, 1560, 1523, 1459, 1378, 1317, 1263, 1168, 1127, 1070, 1034, 998, 959, 899, 820, 755, 710, 669.

Example 7

Compound 7: I; M=M3, L=L2, S=S2; ($R^1=CH_3$, $R^3=H$, $R^4=NHCH_3$, $X^1=$—C(O)NH—, m=4, $X^2=$—NH—, $R^a=R^b=F$, $R^d=OH$)

The compound C3 (74 mg; 0.06 mmole) was dissolved in 10 mL of methanol. 38 mg (0.28 mmole) of $NaOACx3H_2O$ and 15 mg (0.06 mmole) of $I_2$ were added. The reaction mixture was illuminated with a 500W halogen lamp for 2 h. Then, 2–3 drops of 0.1 M $Na_2S_2O_3$ were added. The solvent was then evaporated under reduced pressure and the residue was dissolved in ethyl-acetate and washed with water and saturated $NaHCO_3$ solution. The organic layer was dried over anhydrous $Na_2SO_4$ and evaporated. The product was purified on a silica gel column in the solvent system $CHCl_3:MeOH:NH_4OH=6:1:0.1$. The quantity of 60 mg of the compound 7 was isolated; MS (m/z): 1226.5 $[MH]^+$. $IR(cm^{-1})/KBr$: 3424, 2972, 2939, 2876, 1719, 1670, 1631, 1560, 1523, 1459, 1379, 1314, 1259, 1167, 1127, 1068, 1002, 947, 899, 821, 710.

Example 8

Compound 8: I, M=M2, L=L1, S=S1; ($R^2=R^3=H$, $R^4=N(CH_3)CH_2CH_3$, $X^1=$—$CH_2$—, m=2, $X^2=$—NH—, $R^a=F$, $R^b=H$, $R^d=OH$)

The compound 5 (100 mg; 0.09 mmole) was dissolved in 3 mL of methanol. To the solution, 127 μl of N,N-diisopropylethylamine and 45 μl of ethyliodide was added. The reaction mixture was stirred at a temperature of 50° C. for 20 hours. Subsequently, the mixture was diluted with 30 mL of ethyl-acetate and washed with 30 mL of saturated aqueous sodium-hydrogencarbonate solution and 30 mL of water. The organic layer was dried over anhydrous sodium-sulphate. The solvent was evaporated by reduced pressure. The obtained mixture was purified on a silica gel column, eluent $CHCl_3:MeOH:NH_4OH=6:1:0.1$. 45 mg of the compound 8 was obtained; MS (m/z): 1166.5 $[MH]^+$. $IR(cm^{-1})/KBr$: 3411, 3238, 2969, 2936, 2873, 1723, 1664, 1625, 1565, 1528, 1462, 1379, 1327, 1259, 1169, 1063, 1012, 959, 929, 894, 820, 749, 663, 617.

Example 9

Compound 9: I; M=M2, L=L1, S=S1; ($R^2=R^3=H$, $R^4=N(CH_3)CH_2CH_2CH_3$, $X^1=$—$CH_2$—, m=2, $X^2=$—NH—, $R^a=F$, $R^b=H$, $R^d=OH$)

The compound 5 (90 mg; 0.08 mmole) was dissolved in 2 mL of methanol. To the solution, 115 μl of N,N-diisopropylethylamine (0.67 mmole) and 45.7 μl of propylbromide (0.50 mmole) was added. The reaction mixture was stirred at a temperature of 50° C. for 20 hours. Subsequently, the mixture was diluted with 20 mL of ethyl-acetate and washed with 20 mL of saturated aqueous sodium-hydrogencarbonate solution and 20 mL of water. The organic layer was dried over anhydrous sodium-sulphate. The solvent was evaporated under reduced pressure. The obtained mixture was purified on a silica gel column, eluent $CHCl_3:MeOH:NH_4OH=6:1:0.1$. The quantity of 20 mg of the compound 9 was obtained; MS (m/z): 1180.6 $[MH]^+$. $IR(cm^{-1})/KBr$: 3432, 2964, 2927, 2881, 1736, 1666, 1639, 1627, 1562, 1545, 1525, 1460, 1379, 1262, 1168, 1099, 1054, 1017, 893, 802, 701.

Example 10

Compound 10: I; M=M2, L=L1, S=S1; ($R^2=R^3=H$, $R^4=N(CH_3)CH_2CH_2CH_2CH_3$, $X^1=$—$CH_2$—, m=2, $X^2=$—NH—, $R^a=F$, $R^b=H$, $R^d=OH$)

In 3 mL of methanol, 100 mg of the compound 5 (0.09 mmole) was dissolved. To the solution, 128 μl of N,N-diisopropylethylamine (0.75 mmole) and 63.5 μl of butyliodide (0.56 mmole) was added. The reaction mixture was stirred at a temperature of 50° C. for 20 hours. It was then diluted with 25 mL of ethyl-acetate and washed with 25 mL of saturated aqueous sodium-hydrogencarbonate solution and 25 mL of water. The organic layer was dried over anhydrous sodium-sulphate. The solvent was evaporated by reduced pressure. The obtained mixture was purified on a silica gel column, eluent $CHCl_3:MeOH:NH_4OH=6:1:0.1$. 50 mg of compound 10 was obtained; MS (m/z): 1195.1 $[MH]^+$. $IR(cm^{-1})/KBr$: 3423, 2937, 2874, 1774, 1735, 1719, 1664, 1638, 1578, 1560, 1523, 1491, 1459, 1378, 1263, 1244, 1169, 1106, 1055, 1013, 959, 894, 805, 754.

Example 11

Compound 11: I; M=M2, L=L1, S=S1; ($R^2=R^3=H$, $R^4=N(CH_3)CH(CH_3)_2$, $X^1=$—$CH_2$—, m=2, $X^2=$—NH—, $R^a=F$, $R^b=H$, $R^d=OH$)

The compound 5 (81 mg; 0.07 mmole) was dissolved in 3 mL of methanol. To the solution, 26 μl of acetone, 6.8 mg of sodium-cyanoborhydride and a drop of acetic acid was added. The reaction mixture was stirred at room temperature for 2 days. After two days, an additional 26 μl of acetone was added. The reaction mixture was stirred for further 3 days. The reaction mixture was extracted with 20 mL of ethylacetate and 20 mL of 50% aqueous sodium-hydrogencarbonate solution. The organic layer was washed with water and with saturated aqueous NaCl solution and dried over anhydrous sodium-sulphate. The solvent was evaporated in a rotary evaporator. The obtained mixture was purified on a silica gel column, eluent $CHCl_3$:MeOH:$NH_4OH$=6:1:0.1. 11 mg of the compound 11 was obtained; MS (m/z): 1180.9 $[MH]^+$.

Example 12

Compound 12: I; M=M2, L=L1, S=S1; ($R^2$=$R^3$=H, $R^4$=cyclohexyl, $X^1$=—$CH_2$—, m=2, $X^2$=—NH—, $R^a$=F, $R^b$=H, $R^d$=OH)

The compound 5 (83 mg; 0.07 mmole) was dissolved in 2 μL of methanol. To the solution, 38 μl of cyclohexanone (0.36 mmole), 7 mg of sodium-cyanoborhydride (0.11 mmole) and a drop of acetic acid was added. The reaction mixture was stirred at room temperature for 2 days. The reaction mixture was extracted with 40 mL of ethyl-acetate and 40 mL of 50% aqueous sodium-hydrogencarbonate solution. The organic layer was washed with water and saturated aqueous NaCl solution and dried over anhydrous sodium-sulphate. The solvent was evaporated under reduced pressure. The obtained mixture was purified on a silica gel column, eluent $CHCl_3$:MeOH:$NH_4OH$=6:1:0.1. 11 mg of the compound 12 was obtained; MS (m/z): 1220.6 $[MH]^+$.

Example 13

Compound 13: I; M=M2, L=L1, S=S2; ($R^2$=$R^3$=H, $R^4$=benzyl, $X^1$=—$CH_2$—, m=2, $X^2$=—NH—, $R^a$=$R^b$=F, $R^d$=OH)

The compound 6 (85 mg; 0.07 mmole) was dissolved in 2 mL of methanol. To the solution, 107 μl of N,N-diisopropylethylamine (0.62 mmole) and 55.5 μl of benzyl-bromide (0.47 mmole) was added. The reaction mixture was stirred at a temperature of 50° C. for 20 hours and diluted with 20 mL of ethyl-acetate and washed with 20 mL of saturated aqueous sodium-hydrogencarbonate solution and 20 mL of water. The organic layer was dried over anhydrous sodium-sulphate. The solvent was evaporated under reduced pressure. The obtained mixture was purified on a silica gel column, eluent $CHCl_3$:MeOH:$NH_4OH$=6:1:0.1. 18 mg of compound 13 was obtained; MS (m/z): 1246.6 $[MH]^+$. IR($cm^{-1}$)/KBr: 3433, 2963, 2934, 2875, 1729, 1668, 1640, 1564, 1528, 1496, 1456, 1378, 1318, 1261, 1167, 1126, 1108, 1053, 1034, 999, 960, 901, 802, 750, 700.

Example 14

Compound 14: I; M=M2, L=L1, S=S1; ($R^2$=$R^3$=H, $R^4$=N(CH3)COCH3, $X^1$=—$CH_2$—, m=2, $X^2$=—NH—, $R^a$=F, $R^b$=H, $R^d$=OH)

In 5 mL of methanol, 87 mg of the compound 5 was dissolved and cooled to 2° C. At this temperature, 20 μl of acetanhydride was added drop wise to the reaction mixture. After stirring for three hours at this temperature, the solvent was evaporated and a white, oily product was obtained which was subsequently purified on a silica gel column, eluent $CHCl_3$:MeOH:$NH_4OH$=6:1:0.1. 69 mg of compound 14 was obtained; MS (m/z): 1180.5 $[MH]^+$. IR($cm^{-1}$)/KBr: 3422, 2970, 2938, 2875, 1794, 1774, 1710, 1686, 1664, 1625, 1560, 1523, 1458, 1364, 1223, 1168, 1124, 1061, 1012, 959, 895, 669.

Example 15

Compound 15: I; M=M3, L=L2, S=S2; ($R^1$=$CH_3$, $R^3$=H, $R^4$=N($CH_3$)$CH_2CH_3$, $X^1$=—C(O)NH—, m=4, $X^2$=—NH—, $R^a$=$R^b$=F, $R^d$=OH)

The compound 7 (60 mg; 0.05 mmole) was dissolved in 3 mL of methanol. Subsequently, 0.100 mL (0.57 mmole) of diisopropylethylamine and 0.233 mL of ethyl-iodide was added to the solution. The reaction mixture was stirred at 50° C. overnight. The solvent was then evaporated under reduced pressure and the residue was dissolved in ethyl-acetate and washed with saturated $NaHCO_3$ solution and water. The organic layer was dried over anhydrous $Na_2SO_4$ and evaporated. The mixture was purified on a silica gel column in the solvent system $CHCl_3$:MeOH:$NH_4OH$=6:1:0.1. 15 mg of compound 15 was isolated; MS (m/z): 1255.8 $[MH]^+$.

Example 16

Compound 16: I; M=M2, L=L1, S=S4; ($R^2$=$R^3$=H, $R^4$=$NHCH_3$, $X^1$=—$CH_2$—, m=2, $X^2$=—NH—, $R^a$=F, $R^b$=H, $R^d$=H)

The compound C4 (590 mg; 0.519 mmole) was dissolved in 50 mL of acetonitrile. At a temperature of 0° C. and in a flow of argon, 175 mg of N-iodosuccinimide (0.78 mmole) was added to the solution. The reaction mixture was heated to room temperature and stirred for 5 hours. Subsequently, the mixture was diluted with 100 mL of dichlormethane and extracted with 100 mL of 1:1 5% $NaHSO_3$:$Na_2CO_3$ and saturated NaCl solution. The organic layer was dried over anhydrous sodium-sulphate. The solvent was evaporated under reduced pressure. The obtained mixture was purified on a silica gel column, eluent $CHCl_3$:MeOH:$NH_4OH$=6:1:0.1. 100 mg of compound 16 was obtained; MS (m/z): 1123.2 $[MH]^+$. IR($cm^{-1}$)/KBr: 3448, 2969, 2939, 2876, 1719, 1664, 1638, 1629, 1560, 1542, 1509, 1500, 1459, 1379, 1294, 1247, 1168, 1124, 1065, 1011, 959, 891, 829, 808, 755, 670.

Example 17

Compound 17: I; M=M2, L=L1, S=S4; ($R^2$=$R^3$=H, $R^4$=N($CH_3$)$CH_2CH_3$, $X^1$=—$CH_2$—, m=2, $X^2$=—NH—, $R^a$=F, $R^b$=H, $R^d$=H)

The compound 16 (70 mg; 0.06 mmole) was dissolved in 2 mL of methanol. To the solution was added, 90.8 μl of N,N-diisopropylethylamine (0.53 mmole) and 119.4 μl of ethyl iodide (0.39 mmole). The reaction mixture was stirred in a magnetic mixer at a temperature 50° C. for 20 hours. Subsequently, the mixture was diluted with 30 mL of ethyl-acetate and washed with 30 mL of saturated aqueous sodium-hydrogen carbonate solution and 30 mL of water. The organic layer was dried over anhydrous sodium-sulphate. The solvent was evaporated under reduced pressure. The obtained mixture was purified on a silica gel column, eluent $CHCl_3$:MeOH:$NH_4OH$=6:1:0.1. 32 mg of compound 17 was obtained; MS (m/z): 1150.8 $[MH]^+$. IR($cm^{-1}$)/KBr: 3434, 2969, 2939, 2870, 1719, 1664, 1630, 1561, 1535, 1458, 1383, 1327, 1293, 1236, 1168, 1109, 1058, 1012, 959, 890, 812, 731, 704.

Example 18

Compound 18: I; M=M2, L=L1, S=S4; ($R^2$=$R^3$=H, $R^4$=N($CH_3$)$COCH_3$, $X^1$=—$CH_2$—, m=2, $X^2$=—NH—, $R^a$=F, $R^b$=H, $R^d$=H)

The compound 16 (120 mg) was dissolved in 5 mL of methanol and cooled to 2° C. At this temperature, into the reaction mixture, 28 μl of acetanhydride (0.2 mmole) was added dropwise. After stirring for three hours at this temperature, the solvent was evaporated and the residue was recrystallized (chloroform/hexane). 148 mg of compound 18 was obtained; MS (m/z): 1180.5 [MH]$^+$. IR(cm$^{-1}$)/KBr: 3423, 2979, 2938, 2870, 1735, 1719, 1664, 1625, 1560, 1542, 1509, 1459, 1381, 1293, 1248, 1168, 1122, 1060, 1012, 891, 830, 647.

Example 19

Compound 19: I; M=M2, L=L1, S=S2; (R$^2$=R$^3$=H, R$^4$=N(CH$_3$)CH$_2$CH$_3$, X$^1$=—CH$_2$—, m=2, X$^2$=—NH—, R$^a$=R$^b$=F, R$^d$=OH)

The compound 6 (68 mg; 0.06 mmole) was dissolved in 2 mL of methanol. To the solution was added, 85 µl of N,N-diisopropylethylamine (0.5 mmole) and 112 µl of ethyliodide (0.4 mmole). The reaction mixture was stirred at a temperature of 50° C. for 20 hours. It was then diluted with 20 mL of ethyl-acetate and washed with 20 mL of saturated aqueous sodium-hydrogencarbonate solution and 20 mL of water. The organic layer was dried over anhydrous sodium-sulphate. The solvent was evaporated under reduced pressure. The obtained mixture was purified on a silica gel column, eluent CHCl$_3$:MeOH:NH$_4$OH=6:1:0.1. 38 mg of compound 19 was obtained; MS (m/z): 1185.7 [MH]$^+$. IR(cm$^{-1}$)/KBr: 3425, 2964, 2870, 1721, 1671, 1638, 1562, 1544, 1525, 1460, 1379, 1262, 1168, 1092, 1055, 1032, 958, 899, 864, 803, 707.

Example 20

Compound 20: I; M=M2, L=L1, S=S1; (R$^2$ and R$^3$=III, R$^4$=N(CH$_3$)$_2$, X$^1$=—CH$_2$—, m=2, X$^2$=—NH—, R$^a$=F, R$^b$=H, R$^d$=OH)

Compound C1 (300 mg; 0.26 mmole) was mixed with 139 mg of ethylencarbonate (1.58 mmole) and 42.7 mg of potassium-carbonate (0.31 mmole). To the reaction mixture, 5 mL of ethyl-acetate was added. The solution was heated to 75° C. under stirring for 2 days. Crude potassium-carbonate was filtered, the filtrate was diluted with ethyl-acetate and extracted with water. The organic layer was dried over anhydrous sodium sulphate. The solvent was evaporated under reduced pressure. The obtained mixture was purified on a silica gel column (solvent system: CHCl$_3$:MeOH:NH$_4$OH=6:1:0.1) and 72 mg of compound 20 was obtained; MS (m/z): 1178.3 [MH]$^+$. IR(cm$^{-1}$)/KBr: 3423, 2973, 2939, 2874, 1806, 1736, 1685, 1665, 1625, 1560, 1523, 1458, 1380, 1240, 1168, 1110, 1075, 1052, 1014, 893, 834, 755, 687.

Example 21

Compound 21: I; M=M2, L=L1, S=S1; (R$^2$ and R$^3$=III, R$^4$=N(CH$_3$)CH$_2$CH$_3$, X$^1$=—CH$_2$—, m=2, X$^2$=—NH—, R$^a$=F, R$^b$=H, R$^{d=OH}$)

Compound 8 (65 mg; 0.06 mmole) was mixed with 30 mg of ethylencarbonate (0.34 mmole) and 9.2 mg of potassium-carbonate (0.06 mmole). To the reaction mixture, 3 mL of ethyl-acetate was added. The solution was heated to 75° C. under stirring for 3 days. Crude potassium-carbonate was filtered, the filtrate was diluted with ethyl-acetate and extracted with water. The organic layer was dried over anhydrous sodium sulphate. The solvent was evaporated under reduced pressure. The obtained mixture was purified on a silica gel column, eluent CHCl$_3$:MeOH:NH$_4$OH= 6:1:0.1. 10 mg of compound 21 was obtained; MS (m/z): 1192.9 [MH]$^+$.

Example 22

Compound 22: I; M=M3, L=L2, S=S4; (R$^1$=CH$_3$, R$^3$=H, R$^4$=N(CH$_3$)CH$_2$CH$_3$, X$^1$=—C(O)NH—, m=4, X$^2$=—NH—, R$^a$=F, R$^b$=H, R$^d$=H)

In 10 mL of dichloromethane, 0.07 g (0.21 mmole) of the compound S4 was dissolved. Subsequently, 0.226 mL (1.62 mmole) of triethylamine, 56 mg (0.42 mmole) of hydroxybenzotriazole, 182 mg (0.21 mmole) of the compound B3 and 143 mg (0.83 mmole) of 1-(3-dimethylaminopropyl)-3-ethylcarbodiimide hydrochloride was added to the reaction mixture. The reaction mixture was stirred at room temperature in an inert atmosphere for 24 h. The solvent was then evaporated and the compound purified on a silica gel column in the solvent system CHCl$_3$:MeOH:NH$_4$OH=6:1:0.1. 52 mg of compound 22 was isolated; MS (m/z): 1221.8 [MH]$^+$. IR(cm$^{-1}$)/KBr: 3450, 2971, 2938, 2875, 1775, 1721, 1705, 1628, 1562, 1544, 1526, 1460, 1378, 1294, 1254, 1167, 1110, 1054, 1013, 889, 815, 755.

Preparation Processes with Examples

Preparation of Intermediates

Method AA

The compound P1A (2 g; 2.46 mmole) was dissolved in 100 mL of methanol. To the solution, 2.2 g of sodium acetate trihydrate and 900 mg of iodine was added. The reaction mixture was illuminated with a 500 W halogen lamp for 2 hours. Then, a couple of drops of 1M sodium thiosulphate were added. The solvent was evaporated under reduced pressure. The obtained mixture was purified on a silica gel column (eluent: CHCl$_3$:CH$_3$OH:NH$_4$OH=6:1:0.1). The quantity of 870 mg of the compound A1A was obtained.

According to the above procedure, starting from the macrolide P2A (Table 3), the compound A2A is obtained.

The characteristics of the compounds A1 and A2 are given in Table 3.

Method BB

The compound A1 (4.9 g; 6.68 mmole) was dissolved in 100 mL of methanol. To the solution, 36 mL of N,N-diisopropylethylamine and 13 mL of ethyl iodide were added. The reaction mixture was stirred at the temperature of 50° C. for 20 hours. The reaction mixture was then diluted with ethyl acetate and washed with saturated aqueous solution of sodium-hydrogen carbonate and water. The organic exctract was dried over anhydrous sodium sulphate. The solvent was evaporated under reduced pressure. The obtained mixture was purified on a silica gel column (eluent: CHCl$_3$:MeOH:NH$_4$OH=6:1:0.1). The quantity of 1.63 g of the compound B1A was obtained.

According to the above procedure, starting from the compound A2A, the compound B2A is obtained.

The compound A1A (770 mg; 1.048 mmole) was dissolved in 30 mL of acrylonitrile and the reaction mixture was refluxed for 10 hours. Subsequently, acrylonitrile was evaporated under reduced pressure. 827 mg of compound B3A was obtained.

In accordance with the above procedure and starting from the compound A2, the compound B4A is obtained.

The characteristics of compounds B1A to B4A are given in Table 1.

Method CC

In a 100 mL flask, the macrolide P1A (6.4 g; 8.6 mmole) was dissolved in 50 mL of ethyl acetate. Acetanhydride (1.22 mL; 13.0 mmole) was then added to the reaction mixture. The reaction mixture was stirred at room temperature for 18 h. The reaction mixture was diluted with 50 mL of water and stirred for additional 30 minutes. The pH of the aqueous layer was adjusted to 2.5. Organic and aqueous layers were separated and then the pH of the aqueous phase was adjusted to 9.5 and the aqueous layer was then extracted with ethyl acetate. The extracts were dried over anhydrous $Na_2SO_4$. The solvent was evaporated under reduced pressure and 3.33 g of compound C1A was obtained.

According to the above procedure and starting individually from compounds P2A, P3A, B1A or B2A, the compounds C2A, C3A, C4A or C5A are obtained.

The characteristics of the compounds C1A to C5A are given in Table 1.

Method DD

The compound C1A (6.8 g; 8.6 mmole) was dissolved in 70 mL of dichloromethane. Added to the mixture was 6.8 mL of DMSO and 1-(3-dimethyl aminopropyl)-3-ethyl-carbodiimide hydrochloride (5 g; 29 mmole) in an inert atmosphere. Pyridine trifluoroacetate, dissolved in 3 mL of dichloromethane, was then gradually added drop wise. The reaction mixture was stirred for 2 h at room temperature and subsequently water was added into the reaction mixture. The layers were separated, and the pH of the aqueous layer was adjusted to 4.0. After extraction with ethyl acetate, the pH was adjusted to 6.5. Extraction was repeated, and the pH of the aqueous layer was adjusted to 9.5. After extraction with ethyl acetate, the organic layer was dried over anhydrous $Na_2SO_4$. The solvent was evaporated and 2 g of compound D1A was isolated.

According to the above procedure and starting individually from the compounds C2A, C3A, C4A or C5A, the compounds D2A, D3A, D4A, or D5A are obtained.

The characteristics of the compounds D1A to D5A are given in Table 1.

Method EE

The solution of the compound D1A (1.5 g; 1.9 mmole) in 82 mL of methanol was stirred at room temperature for 20 h. The solvent was then evaporated under reduced pressure and 1.2 g of the compound E1A was obtained.

According to the above procedure and starting individually from the compounds D2A, D3A, D4A or D5A, the compounds E2A, E3A, E4A or E5A are obtained.

The characteristics of the compounds E1A to E5A are given in Table 1.

Method FF

To the solution of NaH (30.9 mg) dissolved in 3.7 mL of DMF, 297 mg of trimethylsulphoxonium iodide (TMSI) was added. After 15 minutes, the solution of the compound E1A (700 mg; 0.94 mmole), dissolved in 2.3 mL of DMSO, was slowly added drop wise. The mixture was stirred at room temperature for 15 min, and then at 55° C. for 45 min. Stirring was then continued at room temperature overnight The reaction mixture was poured into the mixture of water and ethyl acetate. The organic layer was separated, washed with water and saturated solution of NaCl, dried over $Na_2SO_4$, and the solvent was then evaporated under reduced pressure. The quantity of 0.53 g of the compound F1A was obtained.

According to the above procedure, starting individually from the compounds E2A, E3A, E4A or E5A, the compounds F2A, F3A, F4A or F5A are obtained.

The characteristics of the compounds F1A to F5A are given in Table 3.

TABLE 3

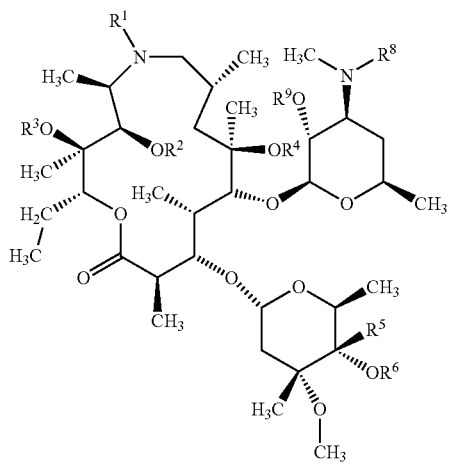

| Com. | $R^1$ | $R^2$ | $R^3$ | $R^4$ | $R^5$ | $R^6$ | $R^8$ | $R^9$ | Molecular formula | $MH^+$ |
|---|---|---|---|---|---|---|---|---|---|---|
| P1A | $CH_3$ | H | H | H | H | H | $CH_3$ | H | $C_{39}H_{72}N_2O_{12}$ | 749.5 |
| P2A | H | C=O | | $CH_3$ | H | H | $CH_3$ | H | $C_{38}H_{70}N_2O_{13}$ | 763.5 |
| P3A | $IPA^a$ | H | H | H | H | H | $CH_3$ | H | $C_{41}H_{77}N_3O_{13}$ | 820.5 |
| A1A | $CH_3$ | H | H | H | H | H | H | H | $C_{37}H_{70}N_2O_{12}$ | 735.5 |
| A2A | H | C=O | | $CH_3$ | H | H | H | H | $C_{37}H_{69}N_2O_{13}$ | 749.4 |
| B1A | $CH_3$ | H | H | H | H | H | $C_2H_5$ | H | $C_{39}H_{74}N_2O_{12}$ | 763.6 |
| B2A | H | C=O | | $CH_3$ | H | H | $C_2H_5$ | H | $C_{39}H_{72}N_2O_{13}$ | 777.7 |
| B3A | $CH_3$ | H | H | H | H | H | $(CH_2)_2$—CN | H | $C_{40}H_{73}N_3O_{12}$ | 788.5 |
| B4A | H | C=O | | $CH_3$ | H | H | $(CH_2)_2$—CN | H | $C_{40}H_{71}N_3O_{13}$ | 822.8 |
| C1A | $CH_3$ | H | H | H | H | H | $CH_3$ | Ac | $C_{40}H_{74}N_2O_{13}$ | 792.1 |

TABLE 3-continued

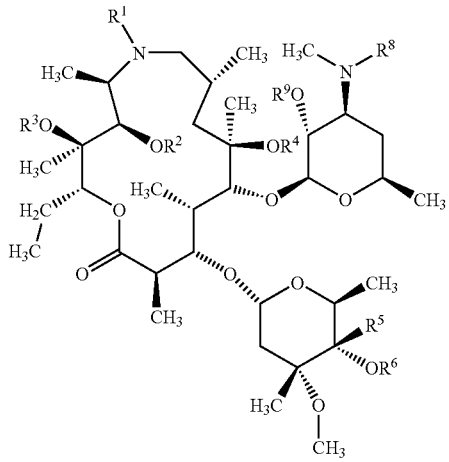

| Com. | $R^1$ | $R^2$ | $R^3$ | $R^4$ | $R^5$ | $R^6$ | $R^8$ | $R^9$ | Molecular formula | $MH^+$ |
|---|---|---|---|---|---|---|---|---|---|---|
| C2A | H | C=O | | $CH_3$ | H | H | $CH_3$ | Ac | $C_{40}H_{72}N_2O_{14}$ | 805.5 |
| C3A | IPA | H | H | H | H | H | $CH_3$ | Ac | $C_{43}H_{79}N_3O_{14}$ | 862.6 |
| C4A | $CH_3$ | H | H | H | H | H | $C_2H_5$ | Ac | $C_{41}H_{76}N_2O_{13}$ | 805.6 |
| C5A | H | C=O | | $CH_3$ | H | H | $C_2H_5$ | Ac | $C_{41}H_{74}N_2O_{14}$ | 819.6 |
| D1A | $CH_3$ | H | H | H | C=O | | $CH_3$ | Ac | $C_{40}H_{72}N_2O_{13}$ | 789.6 |
| D2A | H | C=O | | $CH_3$ | C=O | | $CH_3$ | Ac | $C_{40}H_{70}N_2O_{14}$ | 803.8 |
| D3A | IPA | H | H | H | C=O | | $CH_3$ | Ac | $C_{43}H_{77}N_3O_{14}$ | 860.8 |
| D4A | $CH_3$ | H | H | H | C=O | | $C_2H_5$ | Ac | $C_{41}H_{74}N_2O_{13}$ | 803.6 |
| D5A | H | C=O | | $CH_3$ | C=O | | $C_2H_5$ | Ac | $C_{41}H_{72}N_2O_{14}$ | 817.6 |
| E1A | $CH_3$ | H | H | H | C=O | | $CH_3$ | H | $C_{39}H_{70}N_2O_{12}$ | 747.6 |
| E2A | H | C=O | | $CH_3$ | C=O | | $CH_3$ | H | $C_{39}H_{69}N_2O_{13}$ | 761.5 |
| E3A | IPA | H | H | H | C=O | | $CH_3$ | H | $C_{41}H_{75}N_3O_{13}$ | 818.5 |
| E4A | $CH_3$ | H | H | H | C=O | | $C_2H_5$ | H | $C_{39}H_{72}N_2O_{12}$ | 761.6 |
| E5A | H | C=O | | $CH_3$ | C=O | | $C_2H_5$ | H | $C_{39}H_{70}N_2O_{13}$ | 775.5 |
| F1A | $CH_3$ | H | H | H | $EPO^b$ | | $CH_3$ | H | $C_{39}H_{72}N_2O_{12}$ | 761.8 |
| F2A | H | C=O | | $CH_3$ | EPO | | $CH_3$ | H | $C_{39}H_{70}N_2O_{13}$ | 775.5 |
| F3A | IPA | H | H | H | EPO | | $CH_3$ | H | $C_{42}H_{77}N_3O_{13}$ | 832.5 |
| F4A | $CH_3$ | H | H | H | EPO | | $C_2H_5$ | H | $C_{40}H_{74}N_2O_{12}$ | 775.6 |
| F5A | H | C=O | | $CH_3$ | EPO | | $C_2H_5$ | H | $C_{40}H_{72}N_2O_{13}$ | 789.5 |

[a]IPA = C(O)NHCH(CH$_3$)$_2$
[b]EPO = Oksiran-2-il

Method M a) By hydration of nitrile B3A (770 mg; 1 mmole) with PtO$_2$ as a catalyst (130 mg) in absolute ethanol under pressure of 40 atm for 2 days, 750 mg of the raw product was obtained following filtration and evaporation, it was purified on a silica gel column (eluent:chloroform:methanol:ammonia=6:1:0.1). The quantity of 350 mg of amine $M_L1$ was obtained.

According to the above procedure, starting from nitrile B4A, amine $M_L2$ is obtained.

b) The compound F1A (282 mg; 0.33 mmole) was dissolved in 3 mL of methanol. Added to the solution was ethylenediamine (0.235 mL; 3.33 mmole) and potassium iodide (581.4 mg; 3.28 mmole). The reaction mixture was stirred at the temperature of 50° C. overnight. Methanol was then evaporated under reduced pressure and the residue was dissolved in dichloromethane and washed with water and saturated NaCl solution. After extraction, the organic layer was dried over anhydrous Na$_2$SO$_4$ and the solvent was evaporated. The quantity of 240 mg of amine $M_L3$ was obtained.

According to the above procedure, starting individually from the compounds F2A, F3A, F4A or F5A, amines $M_L4$, $M_L5$, $M_L6$, or $M_L7$ are obtained.

According to the above procedure, adding different diamines to the compounds F2A and F5A, amines $M_L11$ and $M_L12$ are obtained.

According to the above procedure, by reaction of propylene diamine on the compound F4A, amine $M_L8$ is obtained.

c) The compound C1A (1.27 g; 1.6 mmole) was dissolved in 60 mL of toluene in a flow of argon. After 10 min, 0.672 mL of triethylamine and 0.155 mL of 3-chlorpropionylchloride were added. After 15 min, the aliquot of reagents was added again. The reaction mixture was stirred at room temperature for 3 h and water was then added to the reaction mixture. The organic layer was separated, washed with saturated NaHCO$_3$ solution and dried. After solvent evaporation, the product was purified on a silica gel column in the solvent system CHCl$_3$:MeOH:NH$_4$OH=6:1:0,1. The quantity of 0.946 g of the compound $M_L9$ was obtained.

Similar reaction conditions produce the compound $M_L10$.

The characteristics of the compounds $M_L1$ to $M_L10$ are given in Table 4.

TABLE 4

| Com. | M | $R^1$ | $R^2$ | $R^3$ | $R^4$ | $R^5$ | $R^6$ | $R^8$ | Molecular formula | $MH^+$ |
|---|---|---|---|---|---|---|---|---|---|---|
| $M_L1$ | M1 | $CH_3$ | H | H | H | H | H | L1 | $C_{40}H_{77}N_3O_{12}$ | 792.6 |
| $M_L2$ | M2 | H | C=O | $CH_3$ | H | H | H | L1 | $C_{40}H_{75}N_3O_{13}$ | 806.7 |
| $M_L3$ | M1 | $CH_3$ | H | H | H | L2 | H | $CH_3$ | $C_{41}H_{80}N_4O_{12}$ | 821.7 |
| $M_L4$ | M2 | H | C=O | $CH_3$ | H | L2 | H | $CH_3$ | $C_{41}H_{79}N_4O_{13}$ | 835.7 |
| $M_L5$ | M3 | IPA[a] | H | H | H | L2 | H | $CH_3$ | $C_{44}H_{85}N_5O_{13}$ | 892.7 |
| $M_L6$ | M4 | $CH_3$ | H | H | H | L2 | H | $C_2H_5$ | $C_{42}H_{82}N_4O_{12}$ | 835.6 |
| $M_L7$ | M5 | H | C=O | $CH_3$ | H | L2 | H | $C_2H_5$ | $C_{42}H_{80}N_4O_{13}$ | 849.9 |
| $M_L8$ | M4 | $CH_3$ | H | H | H | L3 | H | $C_2H_5$ | $C_{44}H_{86}N_4O_{12}$ | 863.8 |
| $M_L9$ | M1 | $CH_3$ | H | H | L4 | H | H | $CH_3$ | $C_{41}H_{74}N_2O_{13}$ | 803.6 |
| $M_L10$ | M1 | $CH_3$ | H | H | H | H | L4 | $CH_3$ | $C_{41}H_{74}N_2O_{13}$ | 803.9 |
| $M_L11$ | M5 | H | C=O | $CH_3$ | H | L5 | H | $C_2H_5$ | $C_{45}H_{86}N_4O_{13}$ | 891.6 |
| $M_L12$ | M5 | H | C=O | $CH_3$ | H | L6 | H | $C_2H_5$ | $C_{48}H_{92}N_4O_{13}$ | 933.6 |

[a]IPA = —C(O)—NH—CH(CH$_3$)$_2$
L1 = —CH$_2$(CH$_2$)$_2$—NH$_2$
L2 = —CH$_2$—NH—(CH$_2$)$_2$—NH$_2$
L3 = —CH$_2$—NH—(CH$_2$)$_4$—NH$_2$
L4 = —CO—(CH$_2$)$_2$—NH—(CH$_2$)$_2$—NH$_2$
L5 = —CH$_2$—NH—(CH$_2$)$_5$—NH$_2$
L6 = —CH$_2$—NH—(CH$_2$)$_8$—NH$_2$
L7 = —OC(O)(CH$_2$)$_2$NH(CH$_2$)$_3$
L8 = —OC(O)(CH$_2$)$_2$NH(CH$_2$)$_2$NHCH$_2$
L1–L8 corresponds to the link L.

Method S

To the solution of the compound S1 (1.18 g; 3.12 mmole) in 5 mL of DMF were added, N-hydroxysuccinimide (NHS) (723 mg; 6.24 mmol) and 1-(3-dimethylaminopropyl)-3-ethyl-carbodiimide hydrochloride (0.598 g; 3.12 mmole). The reaction mixture was stirred at room temperature overnight. Added to the solution were then NH$_2$CH$_2$CH$_2$NH-Boc (0.492 mL; 3.12 mmole) and triethylamine (0.426 mL; 3.062 mmole). The reaction mixture was stirred at room temperature for additional 24 h. The mixture was subsequently transferred to 20 mL of dichloromethane and washed with saturated solution of NaHCO$_3$ and water. After drying over anhydrous Na$_2$SO$_4$, the solvent was evaporated. The quantity of 2.2 g of oily product was obtained; it was dissolved in 30 mL of TFA:CH$_2$Cl$_2$ and stirred at room temperature for 1 h. The solvent was subsequently evaporated under reduced pressure. The quantity of 1.24 g of amide S3 was obtained.

Method Sa

A solution of steroid S1 (1.0 g. 2.64 mmol) and triethylamine (0.74 ml. 5.29 mmol) in CH$_2$Cl$_2$ (60 ml) at 0° C. was treated with acryloyl chloride (0.429 ml. 5.29 mmol). After 30 min the reaction mixture was diluted with CH$_2$Cl$_2$, washed with aqueous NaHCO$_3$ and then H$_2$O, dried and evaporated to give the solid intermediate. This was stirred in acetone (50 ml) with diethylamine (1.38 ml. 13.215 mmol) for 2 hours. Solution was concentrated, diluted with water and washed with EtOAc. The aqueous phase was acidified to pH 2 with 2 N HCl and filtered to provide a solid. 915 mg of compound S5 was obtained.

Method Sb 1.8-Diazabicyclo[5.4.0]undec-7-ene (DBU) (1 equiv, 0.23 mmol, 0.035 ml) was added to a 10% solution of acid S5 (0.23 mmol, 100 mg) in dimethylcarbonate and the resulting mixture was heated to reflux (90° C.). After completion, the reaction mixture was cooled to room temperature and diluted with EtOAc and water. The organic layer was dried over Na$_2$SO$_4$, evaporated and purified on a silica gel column in the solvent system CH$_2$Cl$_2$:MeOH:NH$_4$OH=90:8:1. 80 mg of the compound S6 was obtained.

Method Sc

A solution of compound S5 (184 mg, 0.24 mmol) and N,N-dimethylthiocarbamoyl chloride (60.5 mg, 0.49 mmol) in 2-butanone (8 ml) at room temperature was treated sequentially with triethylamine (0.075 ml, 0.54 mmol), sodium iodide (37 mg, 0.24 mmol), and water (0.018 ml) and stirred for 3 days. Reaction mixture was then treated sequentially with dimethyacetamide (0.88 ml) and water (5.54 ml); cooled to 0° C., stirred for 2 hours and extracted with EtOAc. Organic layer vas dried over Na$_2$SO$_4$ and evaporated under reduced pressure. Mixture was purified on a silica gel column in the solvent system CH$_2$Cl$_2$:MeOH:NH$_4$OH=90:8:1. 20 mg of the compound S7 was obtained.

Method Sd a) In a solution of compound S5 (250 mg, 0.58 mmol) in methanol (20 ml) 915 mg (1.16 mmol) of the macrolide A4 was added. Reaction mixture was stirred at 55° C. for 24 hours. After evaporation of the solvent, mixture was purified on a silica gel column in the solvent system CH$_2$Cl$_2$:MeOH:NH$_4$OH=30:50:2. 540 mg of the compound S8 was obtained. MS (m/z): 1224.32 [MH]$^+$. IR(cm$^{-1}$)/KBr: 3423, 2972, 2939, 2876, 1726, 1686, 1664, 1618, 1605, 1561, 1509, 1459, 1380, 1247, 1168, 1116, 1074, 1056, 1013, 894, 818, 802.

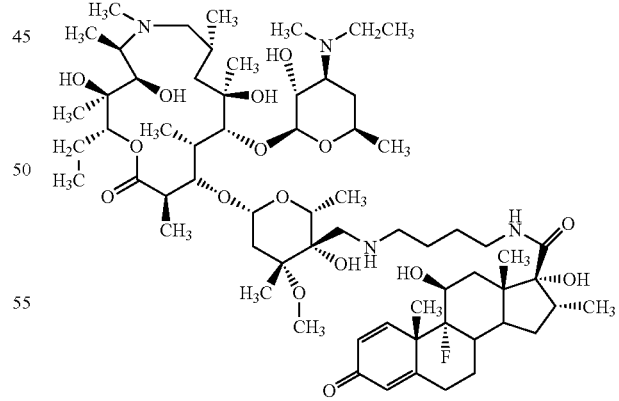

b) In a solution of compound S5 (250 mg, 0.58 mmol) in methanol (20 ml), 755 mg (1.16 mmol) of the macrolide M$_L$3 was added. Reaction mixture was stirred at 55° C. for 24 hours. After evaporation of the solvent, mixture was purified on a silica gel column in the solvent system CH$_2$Cl$_2$:MeOH:NH$_4$OH=30:50:2. 412 mg of the compound S9 was obtained. MS (m/z): 1253.58 [MH]$^+$

TABLE 5

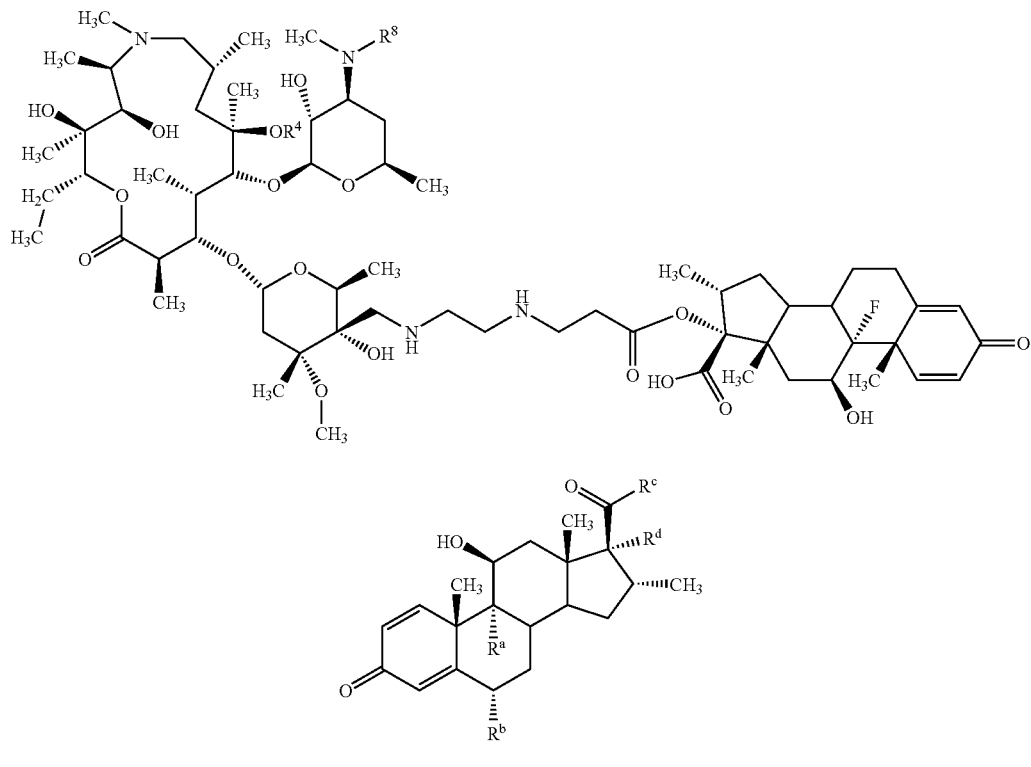

| S | $R^a$ | $R^b$ | $R^c$ | $R^d$ | Molecular formula | $MH^+$ |
|---|---|---|---|---|---|---|
| S1 | F | H | OH | OH | $C_{21}H_{27}FO_5$ | 378.9 |
| S2 | F | F | OH | OH | $C_{21}H_{26}F_2O_5$ | 397.4 |
| S3 | F | H | NH—$(CH_2)_2$—$NH_2$ | OH | $C_{23}H_{33}FN_2O_4$ | 421.3 |
| S4 | F | H | OH | H | $C_{21}H_{27}FO_4$ | 363.2 |
| S5 | F | H | OH | $OC(O)CH_2=CH_2$ | $C_{24}H_{29}FO_6$ | 433.2 |
| S6 | F | H | $CH_3$ | $OC(O)CH_2=CH_2$ | $C_{25}H_{31}FO_6$ | 446.9 |
| S7 | F | H | $SC(O)N(CH_3)_2$ | $OC(O)CH_2=CH_2$ | $C_{27}H_{34}FNO_6S$ | 520.2 |

Example 23

Compound 23: I; M=M1, L=L1, S=S1; ($R^1=R^7=CH_3$, $R^2=R^3=R^4=R^5=R^6=H$, $X^1=CH_2$, m=2, Q=NH, n=0, $X^2=NH$, $R^a=F$, $R^b=H$, $R^d=OH$)

The compound S1 (84 mg; 0.22 mmole) was dissolved in 5 mL of dry dichlormethane. To the solution, 0.29 mL of triethylamine and 61 mg of hydroxybenzotriazole were added and subsequently the macrolide $M_L1$ (175 mg; 0.22 mmole) and 1-(3-dimethylaminopropyl)-3-ethylcarbodiimide hydrochloride (179 mg) were added. The reaction mixture was stirred at room temperature overnight. The solvent was evaporated under reduced pressure and the obtained mixture was purified on a silica gel column, eluent $CHCl_3$:MeOH:$NH_4OH$=6:1:0.1. 16 mg of compound 23 was obtained; MS (m/z): 1152.5 $[MH]^+$.

Example 24

Compound 24: I; M=M2, L=L1, S=S1; ($R^1=R^5=R^6=H$, $R^2$ together with $R^3$=CO, $R^4=R^7=CH_3$, $X^1=CH_2$, m=2, Q=NH, n=0, $X^2=NH$, $R^a=F$, $R^b=H$, $R^d=OH$)

The compound S1 (117.5 mg; 0.31 mmole) was dissolved in 5 mL of dry DMF. To the solution, 58.6 μl of diisopropylethylamine and 42 mg of 1-hydroxybenzotriazole were added and then the macrolide $M_L2$ (250 mg; 0.31 mmole) and 1-(3-dimethylaminopropyl)-3-ethylcarbodiimide hydrochloride (60 mg) were added. The reaction mixture was stirred at the temperature of 100° C. for 5 hours. The mixture was exctracted twice with 40 mL of ethyl-acetate and 40 mL of water each time. The organic layers were washed twice with 30 mL of water each time and dried over anhydrous sodium-sulphate. The solvent was evaporated under reduced pressure and the obtained mixture was purified on a silica gel column, eluent $CHCl_3$:MeOH:$NH_4OH$=6:1:0.1, with 65 mg of compound 24 being obtained; MS (m/z): 1166.7 $[MH]^+$. IR($cm^{-1}$)/KBr: 3423, 2972, 2938, 2881, 1774, 1736, 1702, 1664, 1560, 1528, 1459, 1379, 1298, 1244, 1170, 1126, 1108, 1075, 1055, 1011, 959, 894.

Example 25

Compound 25: I; M=M1, L=L2, S=S2; ($R^1=R^7=R^8=CH_3$, $R^2=R^3=R^4=R^6=H$, $X^1=CH_2$, m=0, Q=NH, n=2, $X^2=NH$, $R^a=R^b=F$, $R^d=OH$)

The compound S2 (116 mg; 0.29 mmole) was dissolved in 10 mL of dichloromethane. Added were 0.320 mL of triethylamine and 78 mg of 1-hydroxybenzotriazole and then the compound $M_L3$ (240 mg; 0.29 mmole) and 1-(3-dimethylaminopropyl)-3-ethyl-carbodiimide hydrochloride (200 mg). The reaction mixture was stirred at room temperature in an inert atmosphere for 24 h. The solvent was then evaporated and the compound purified on a silica gel column in the solvent system $CHCl_3$:MeOH:$NH_4OH$=6:1:0.1. 214 mg of compound 25 was isolated; MS (m/z): 1200.0 [MH]$^+$. IR(cm$^{-1}$)/KBr: 3423, 2973, 2939, 2876, 1711, 1670, 1632, 1561, 1523, 1458, 1380, 1317, 1259, 1177, 1130, 1110, 1073, 1034, 995, 939, 898, 795, 757, 710, 642.

Example 26

Compound 26: I; M M1, L=L2, S=S1; ($R^1$=$R^7$=$R^8$=$CH_3$, $R^2$=$R^3$=$R^4$=$R^6$=H, $X^1$=$CH_2$, m=0, Q=NH, n=2, $X^2$=NH, $R^a$=F, $R^b$=H, $R^d$=OH)

To the suspension of the compound S1 (111 mg; 0.29 mmole) in dry $CH_2Cl_2$ (5 mL) cooled to 0° C. under argon were added, 0.380 mL of triethylamine and 80 mg of 1-hydroxybenzotriazole and then the compound $M_L3$ (240 mg; 0.29 mmole) and 1-(3-dimethylaminopropyl)-3-ethyl-carbodiimide hydrochloride (235 mg). The reaction mixture was stirred at room temperature in a flow of argon for 24 hours and then evaporated to a smaller volume under reduced pressure and purified on a silica gel column (eluent: $CHCl_3$:$CH_3OH$:$NH_4OH$=6:1:0,1). 88 mg of compound 26 was obtained; MS (m/z): 1182 [MH]$^+$. IR(cm$^{-1}$)/KBr: 3423, 2971, 2939, 2874, 1719, 1665, 1625, 1560, 1518, 1458, 1378, 1275, 1175, 1110, 1036, 1013, 996, 894, 796, 757, 670.

Example 27

Compound 27: I; M=M2, L=L2, S=S2; ($R^1$=$R^6$=H, $R^2$ together with $R^3$=CO, $R^4$=$R^7$=$R^8$=$CH_3$, $X^1$=$CH_2$, m=0, Q=NH, n=2, $X^2$=NH, $R^a$=$R^b$=F, $R^d$=OH)

The compound S2 (47 mg; 0.12 mmole) was dissolved in dry $CH_2Cl_2$ (5 mL) in an inert atmosphere and 0.128 mL of triethylamine and 31 mg of 1-hydroxybenzotriazole were added, subsequently, the compound $M_L4$ (141 mg; 0.12 mmole) and 1-(3-dimethylaminopropyl)-3-ethyl-carbodiimide hydrochloride (169 mg) were added. The reaction mixture was stirred at room temperature in a flow of argon for 24 hours and then evaporated to a smaller volume under reduced pressure and purified on a silica gel column (eluent: $CHCl_3$:$CH_3OH$:$NH_4OH$=6:1:0.1). 82 mg of compound 27 was obtained; MS (m/z): 1213 [MH]$^+$.

Example 28

Compound 28: I; M=M3, L=L2, S=S2; $R^1$=CONHCH($CH_3$)$_2$, $R^2$=$R^3$=$R^4$=$R^6$=H, $R^7$=$R^8$=$CH_3$, $X^1$=$CH_2$, m=0, Q=NH, n=2, $X^2$=NH, $R^a$=$^b$=F, $R^d$=OH)

The compound S2 (95 mg; 0.24 mmole) was dissolved in 10 mL of dichloromethane, 0.262 mL of triethylamine and 65 mg of 1-hydroxybenzotriazole were added and then the compound $M_L5$ (257 mg; 0.24 mmole) and 1-(3-dimethylaminopropyl)-3-ethyl-carbodiimide hydrochloride (165 mg) were added. The reaction mixture was stirred at room temperature in an inert atmosphere for 24 h. The solvent was then evaporated and the compound purified on a silica gel column in the solvent system $CHCl_3$:MeOH:$NH_4OH$=6:1:0.1. 144 mg of compound 28 was isolated; MS (m/z): 1270 [MH]$^+$. IR(cm$^{-1}$)/KBr: 3423, 2974, 2940, 2877, 1774, 1735, 1719, 1670, 1630, 1561, 1523, 1459, 1381, 1317, 1264, 1168, 1110, 1072, 1032, 994, 899, 820, 757, 709.

Example 29

Compound 29: I; M=M4, L=L2, S=S1; ($R^1$=$R^7$=$CH_3$, $R^2$=$R^3$=$R^4$=$R^6$=H, $R^8$=$CH_2CH_3$, $X^1$=$CH_2$, m=0, Q=NH, n=2, $X^2$=NH, $R^a$=F, $R^b$=H, $R^d$=OH)

The compound S1 (282 mg; 0.71 mmole) was dissolved in dry $CH_2Cl_2$ (15 mL) in an inert atmosphere, 0.776 mL of triethylamine and 192 mg of 1-hydroxybenzotriazole were added and then the compound $M_L6$ (593 mg; 2.85 mmole) and 1-(3-dimethylaminopropyl)-3-ethyl-carbodiimide hydrochloride (489 mg) were added. The reaction mixture was stirred in a flow of argon at room temperature for 24 hours and then evaporated to a smaller volume under reduced pressure and purified on a silica gel column (eluent: $CHCl_3$:$CH_3OH$:$NH_4OH$=6:1:0.1). 84 mg of compound 29 was obtained; MS (m/z): 1195.9 [MH]$^+$. IR(cm$^{-1}$)/KBr: 3424, 2972, 2939, 2874, 1725, 1665, 1625, 1560, 1522, 1459, 1379, 1259, 1176, 1109, 1054, 1036, 1012, 996, 894, 796, 757.

Example 30

Compound 30: I; M=M5, L=L2, S=S1; ($R^1$=$R^6$=H, $R^2$ together with $R^3$=CO, $R^4$=$R^7$=$CH_3$, $R^8$=$CH_2CH_3$, $X^1$=$CH_2$, m=0, Q=NH, n=2, $X^2$=NH, $R^a$=F, $R^b$=H, $R^d$=OH)

In 15 mL of dry dichloromethane, the compound S1 (89 mg; 0.23 mmole) was dissolved. Added were 0.257 mL of triethylamine and 64 mg of 1-hydroxybenzotriazole and then the compound $M_L7$ (200 mg; 0.23 mmole) and 1-(3-dimethylaminopropyl)-3-ethyl-carbodiimide hydrochloride (162 mg). The reaction mixture was stirred in an inert atmosphere at room temperature for 24 h. The solvent was then evaporated under reduced pressure and the compound purified in a silica gel column in the solvent system $CHCl_3$:MeOH:$NH_4OH$=6:1:0.1. 153 mg of compound 30 was obtained; MS (m/z): 1209.7 [MH]$^+$. IR(cm$^{-1}$)/KBr: 3423, 2974, 2939, 2881, 1774, 1708, 1664, 1560, 1523, 1459, 1379, 1299, 1275, 1221, 1175, 1109, 1053, 1010, 893, 813, 757.

Example 31

Compound 31: I; M=M5, L=L2, S=S4; ($R^1$=$R^6$=H, $R^2$ together with $R^3$=CO, $R^4$=$R^7$=$CH_3$, $R^8$=$CH_2CH_3$, $X^1$=$CH_2$, m=0, Q=NH, n=2, $X^2$=NH, $R^a$=F, $R^b$=H, $R^d$=H)

The compound S4 (85 mg; 0.24 mmole) was dissolved in 10 mL of dry dichloromethane. Added were 0.257 mL of triethylamine and 64 mg of 1-hydroxybenzotriazole and then the compound $M_L7$ (200 mg; 0.24 mmole) and 1-(3-dimethylaminopropyl)-3-ethyl-carbodiimide hydrochloride (162 mg). The reaction mixture was stirred in an inert atmosphere at room temperature for 24 h. The solvent was then evaporated under reduced pressure and the compound was purified on a silica gel column in the solvent system $CHCl_3$:MeOH:$NH_4OH$=6:1:0.1. 106 mg of compound 31 was obtained; MS (m/z): 1193.6 [MH]$^+$. IR(cm$^{-1}$)/KBr: 3448, 2973, 2940, 2876, 1708, 1664, 1560, 1528, 1459, 1379, 1297, 1272, 1225, 1176, 1110, 1053, 1010, 929, 889, 810, 756.

Example 32

Compound 32: I; M=M4, L=L3, S=S1; ($R^1$=$R^7$=$CH_3$, $R^2$=$R^3$=$R^4$=$R^6$=H, $R^8$=$CH_2CH_3$, $X^1$=$CH_2$, m=0, Q=NH, n=4, $X^2$=NH, $R^a$=F, $R^b$=H, $R^d$=OH)

The compound S1 (74 mg; 0.19 mmole) was dissolved in dry $CH_2Cl_2$ (10 mL) in an inert atmosphere and 0.176 mL of triethylamine and 53 mg of 1-hydroxybenzotriazole were added, followed by the addition of the compound $M_L8$ (169 mg; 0.19 mmole) and 1-(3-dimethylaminopropyl)-3-ethyl-carbodiimide hydrochloride (135 mg). The reaction mixture was stirred in a flow of argon at room temperature for 24 hours and then evaporated to a smaller volume under reduced pressure and purified on a silica gel column (eluent: $CHCl_3$:$CH_3OH$:$NH_4OH$=6:1:0.1). 67 mg of compound 32 was obtained; MS (m/z): 1223.6 [MH]$^+$. IR(cm$^{-1}$)/KBr: 3425, 2979, 2937, 2873, 2370, 1734, 1665, 1627, 1562, 1525, 1459, 1379, 1259, 1175, 1109, 1054, 1036, 1012, 995, 893, 796, 756.

Example 33

Compound 33: I; M=M1, L=L5, S=S1; ($R^1=R^7=R^8=CH_3$, $R^2=R^3=R^4=R^5$=H, $X^1$=CO, m=2, Q=NH, n=2, $X^2$=NH, $R^a$=F, $R^b$=H, $R^d$=OH)

The compound S3 (109 mg; 0.26 mmole) was dissolved in 20 mL of methanol and then the compound $M_L10$ (250 mg; 0.31 mmole) was added. The reaction mixture was stirred at 75° C. for 24 h. The solvent was then evaporated under reduced pressure and the compound was purified on a silica gel column in the solvent system $CHCl_3$:MeOH:$NH_4OH$=6:1:0.1. 40 mg of compound 33 was obtained; MS (m/z): 1223.9 $[MH]^+$. IR($cm^{-1}$)/KBr: 3424, 2972, 2939, 2873, 1734, 1665, 2639, 1562, 1525, 1459, 1379, 1260, 1173, 1108, 1074, 1036, 1015, 960, 894, 835, 797, 755, 642.

Example 34

Compound 34: I; M=M1, L=L5, S=S1; ($R^1=R^7=R^8=CH_3$, $R^2=R^3=R^5=R^6$=H, $X^1$=CO, m=2, Q=NH, n=2, $X^2$=NH, $R^a$=F, $R^b$=H, $R^d$=OH)

The compound $M_L9$ (267 mg; 0.32 mmole) was dissolved in 30 mL of methanol. To the solution, the compound S3 (399 mg; 0.95 mmole) was added. The reaction mixture was stirred at 75° C. overnight. The solvent was then evaporated and the obtained mixture was purified on a silica gel column in the solvent system $CHCl_3$:MeOH:$NH_4OH$=6:1:0.1. 30 mg of compound 34 was obtained; MS (m/z): 1223.7 $[MH]^+$. IR($cm^{-1}$)/KBr: 345, 2972, 2941, 2873, 1722, 1665, 1627, 1525, 1459, 1379, 1296, 1243, 1184, 1110, 1053, 1012, 894, 831, 756.

Example 35

Compound 35: I; M=M5, L=L6, S=S4; ($R^1=R^6$=H, $R^2$ together with $R^3$=CO, $R^4=R^7=CH_3$, $R^8=CH_2CH_3$, $X^1=CH_2$, m=0, Q=NH, n=5, $X^2$=NH, $R^a$=F, $R^b$=H, $R^d$=H)

The compound S4 (63 mg; 0.17 mmole) was dissolved in 10 mL of dry dichloromethane. Added were 0.188 mL of triethylamine and 47 mg of 1-hydroxybenzotriazole and then the compound $M_L11$ (154 mg; 0.17 mmole) and 1-(3-dimethylaminopropyl)-3-ethyl-carbodiimide hydrochloride (119 mg). The reaction mixture was stirred in an inert atmosphere at room temperature for 24 h. The solvent was then evaporated under reduced pressure and the compound was purified on a silica gel column in the solvent system $CHCl_3$:MeOH:$NH_4OH$=6:1:0.1. 250 mg of compound 35 was obtained; MS (m/z): 1236,5 $[MH]^+$. IR($cm^{-1}$)/KBr: 3448, 2972, 2938, 2870, 1736, 1708, 1664, 1560, 1535, 1459, 1379, 1329, 1297, 1272, 1229, 1176, 1110, 1053, 1010, 931, 889, 809.

Example 36

Compound 36: I; M=M5, L=L7, S=S4; ($R^1=R^6$=H, $R^2$ together with $R^3$=CO, $R^4=R^7=CH_3$, $R^8=CH_2CH_3$, $X^1=CH_2$, m=0, Q=NH, n=8, $X^2$=NH, $R^a$=F, $R^b$=H, $R^d$=H)

The compound S4 (73 mg; 0.20 mmole) was dissolved in 10 mL of dry dichloromethane. Added were 0.219 mL of triethylamine and 54 mg of 1-hydroxybenzotriazole and then the compound $M_L12$ (188 mg; 0.20 mmole) and 1-(3-dimethylaminopropyl)-3-ethyl-carbodiimide hydrochloride (139 mg). The reaction mixture was stirred in an inert atmosphere at room temperature for 24 h. The solvent was then evaporated under reduced pressure and the compound was purified on a silica gel column in the solvent system $CHCl_3$:MeOH:$NH_4OH$=6:1:0.1. 54 mg of compound 36 was obtained; MS (m/z): 1277.6 $[MH]^+$.

Example 37

Compound 37: I; M=M2, L=L6, S=S4; ($R^1=R^6$=H, $R^2$ together with $R^3$=CO, $R^4=R^7=CH_3$, $R^8=CH_2CH_3$, $X^1=CH_2$, m=0, Q=NH, n=2, $X^2$=NH, $R^a$=F, $R^b$=H, $R^d$=H)

The compound S4 (34 mg; 0.093 mmole) was dissolved in 10 mL of dry dichloromethane. Added were 0.100 mL of triethylamine and 25 mg of 1-hydroxybenzotriazole and then the compound $M_L4$ (29 mg; 0.093 mmole) and 1-(3-dimethylaminopropyl)-3-ethyl-carbodiimide hydrochloride (64 mg). The reaction mixture was stirred in an inert atmosphere at room temperature for 24 h. The solvent was then evaporated under reduced pressure and the compound was purified on a silica gel column in the solvent system $CHCl_3$:MeOH:$NH_4OH$=6:1:0.1. 10 mg of compound 37 was obtained; MS (m/z): 1179.7 $[MH]^+$.

Example 38

Compound 38: I; M=M1, L=L7, S=S6; ($R^2=R^3=R^4=R^5=R^6$=H, $R^8=CH_3$, X1=—$CH_2$—, m=2, n=2 Q=—NH—, $X^2$=OC(O), $R^a$=F, $R^b$=H, $R^c=OCH_3$)

a) 1,8-Diazabicyclo[5.4.0]undec-7-ene (DBU) (1 equiv, 0.082 mmol, 0.012 ml) was added to a 10% solution of acid S8 (100 mg, 0.082 mmol) in dimethylcarbonate (1 ml) and the resulting mixture was heated to reflux (90° C.). After completion, the reaction mixture was cooled to room temperature and diluted with EtOAc and water. The organic layer was dried over $Na_2SO_4$, evaporated and purified on a silica gel column in the solvent system $CH_2Cl_2$:MeOH:$NH_4OH$=90:8:1. 32 mg of the compound 38 was obtained. MS (m/z): 1238.55 $[MH]^+$. IR($cm^{-1}$)/KBr: 3449, 2972, 2939, 2877, 1736, 1666, 1625, 1561, 1542, 1509, 1459, 1377, 1291, 1266, 1241, 1176, 1115, 1052, 1014, 978, 957, 893, 833, 812, 755, 705, 639.

b) In a solution of compound S6 (17.3 mg, 0.039 mmol) in methanol (3 ml) 62 mg (0.094 mmol) of the macrolide A4 was added. Reaction mixture was stirred at 55° C. for 24 hours. After evaporation of the solvent, mixture was purified on a silica gel column in the solvent system $CH_2Cl_2$:MeOH:$NH_4OH$=90:8:1. 35 mg of the compound 38 was obtained. MS (m/z): 1238.55 $[MH]^+$

Example 39

Compound 39: I; M=M1, L=L8, S=S6; ($R^1=R^7=R^8=CH_3$, $R^2=R^3=R^4=R^6$=H, $X^1=CH_2NH$, m=2, Q=NH, n=2, $X^2$=OC(O), $R^a$=F, $R^b$=H, $R^c=OCH_3$)

In a solution of compound S6 (100 mg, 0.22 mmol) in methanol (10 ml), 212 mg (0.26 mmol) of the macrolide $M_L3$ was added. Reaction mixture was stirred at 55° C. for 24 hours. After evaporation of the solvent, mixture was purified on a silica gel column in the solvent system $CH_2Cl_2$:MeOH:$NH_4OH$=90:8:1. 20 mg of the compound 39 was obtained. MS (m/z): 1267.55 $[MH]^+$

Example 40

Compound 40: I; M=M1, L=L7, S=S7; ($R^2=R^3=R^4=R^5=R^6$=H, $R^8=CH_3$, X1=—$CH_2$—, m=2, n=2 Q=—NH—, $X^2$=OC(O), $R^a$=F, $R^b$=H, $R^c=SC(O)N(CH_3)_2$)

A solution of compound S8 (150 mg, 0.12 mmol) in 2-butanone (4 ml) at room temperature was treated sequentially with triethylamine (37.5 ml, 0.27 mmol), sodium iodide (18.4 m, 0.12 mmol), and water (0.015 ml) and stirred for 3 days. Reaction mixture was then treated sequentially with dimethyacetamide (0.44 ml) and water (2.77 ml); cooled to 0° C., stirred for 2 hours and extracted with EtOAc. Organic layer vas dried over $Na_2SO_4$ and evaporated under reduced pressure. Mixture was purified on a silica gel column in the solvent system $CH_2Cl_2$:MeOH:$NH_4OH$=90:8:1. 56.3 mg of the compound 40 was obtained. MS (m/z): 1311.49 $[MH]^+$

What is claimed is:

1. A compound of the formula:

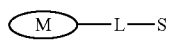

wherein M represents a group of Formula II:

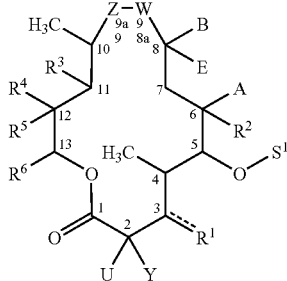

wherein
(i) Z and W independently are >C=O, >CH$_2$, >CH—NR$_t$R$_s$, >N—R$_N$ or >C=N—R$_M$, wherein R$_t$ and R$_s$ independently are hydrogen or alkyl;
R$_M$ is hydroxy, alkoxy, substituted alkoxy or OR$^p$;
R$_N$ is hydrogen, R$^p$, alkyl, alkenyl, alkynyl, alkoxy, alkoxyalkyl, or —C(X)—NR$_t$R$_s$; wherein X is =O or =S;
provided that Z and W cannot both simultaneously be, >C=O, >CH$_2$, >CH—NR$_t$R$_s$, >N—R$_N$, >C=N—R$_M$ or a bond;
(ii) U and Y independently are hydrogen, halogen, alkyl, or hydroxyalkyl;
(iii) R$^1$ is hydroxy, OR$^p$, —O—S$^2$ group or an =O;
(iv) S$^1$ is a sugar moiety of Formula III:

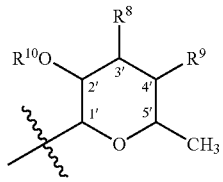

wherein
R$^8$ and R$^9$ are both hydrogen or together form a bond, or R$^9$ is hydrogen and R$^8$ is —N(CH$_3$)R$^y$, wherein
R$^y$ is R$^p$, R$^z$ or —C(O)R$^z$, wherein R$^z$ is hydrogen or alkyl or alkenyl or alkynyl or cycloalkyl or 1 or heteroaryl or alkyl substituted with C$_2$–C$_7$-alkyl, C$_2$–C$_7$-alkenyl, C$_2$–C7-alkynyl, aryl or heteroaryl;
R$^{10}$ is hydrogen or R$^p$;
S$^2$ sugar moiety of Formula IV:

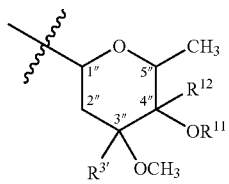

wherein
R$^{3'}$ is hydrogen or methyl;
R$^{11}$ is hydrogen, R$^p$, or O—R$^{11}$ is a group that with R$^{12}$ and with C/4" carbon atom forms a >C=O or epoxy group;
R$^{12}$ is hydrogen or a group that with O—R$^{11}$ group and with C/4" carbon atom forms a >C=O or epoxy group;
(vi) R$^2$ is hydrogen hydroxy, OR$^p$ or alkoxy;
(vii) A is hydrogen or methyl;
(viii) B is methyl or epoxy;
(ix) E hydrogen or halogen;
R$^3$ is hydroxy, OR$^p$, alkoxy or R$^3$ is a group that with R$^5$ and with C/11 and C/12 carbon atoms forms a cyclic carbonate or carbamate, or if W or Z is >N—R$_N$ R$^3$ is a group at with W or Z forms a cyclic carbamate;
(xi) R$^4$ is C$_1$–C$_4$ alkyl;
(xii) R$^5$ is hydrogen hydroxy, OR$^p$, C$_1$–C$_4$ alkoxy, or a group that with R$^3$ and with C/11 an C/12 carbon atoms forms a cyclic carbonate or carbamate;
(xiii) R$^6$ is hydrogen or C$_1$–C$_4$-alkyl; and R$^p$ iss hydroxyl or amino protective group;
wherein M has a linkage site through which it is linked to S via linking group L; provided that linkage site at one or more of the following:
a) any reactive hydroxy, nitrogen, or epoxy group located on S$^1$. S$^2$, or an aglycone oxygen if S$^1$ and/or S$^2$ is cleaved off;
b) a reactive >N—R$_N$ or —NR$_t$R$_s$ or oxo group located on Z or W;
c) a reactive hydroxy group located at any one of R$^1$, R$^2$, R$^3$, and R$^5$;
d) any other group that can be first derivatized to a hydroxy or —NR$_t$R$_s$ group and
S represents a group of Formula X:

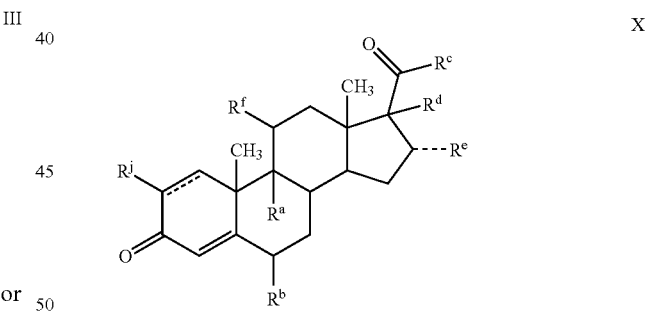

wherein
R$^a$ and R$^b$ independently represents, hydrogen or halogen;
R$^c$ is hydroxy, alkoxy, alkyl, thiocarbamoyl, carbamoyl or a valence-bond;
R$^d$ and R$^e$ independently represents: hydrogen, hydroxy, methyl or C$_1$–C$_4$-alkoxy or each are a group that forms a 1,3-dioxolane ring with the other or a valence bond;
R$^f$ is hydrogen, hydroxy, chloro, or forming a keto group with the carbon atom it is attached to;
R$^j$ is hydrogen or halogen;
or a pharmaceutically acceptable salt or solvate thereof;
wherein
L is a linker molecule to which each of M and S are covalently linked.

2. A compound of the Formula I:

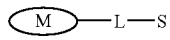   I wherein M represents a group of Formula II:

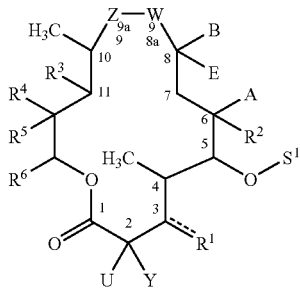   II wherein
(i) Z and W independent are >C=O, >CH$_2$, >CH—NR$_t$R$_s$, >N—R$_N$ or >C=N—R$_M$, wherein
R$_t$ and R$_s$ independently are hydrogen or alkyl;
R$_M$ is hydroxy, alkoxy, substituted alkoxy or OR$^P$;
R$_N$ is hydrogen, R$^P$, alkyl, alkenyl, alkynyl, alkoxy, alkoxyalkyl, or —C(X)—NR$_t$R$_s$; wherein X is =O or =S;
provided that Z and W cannot both simultaneously be, >C=O, >CH$_2$, >CH—NR$_t$R$_s$, >N—R$_N$, >C=N—R$_M$ or a bond;
(ii) U and Y independently are hydrogen, halogen, alkyl, or hydroxyalkyl;
(iii) R$^1$ is hydroxy, OR$^P$, —O—S$^2$ group or an =O;
(iv) S$^1$ is a sugar moiety of Formula III:

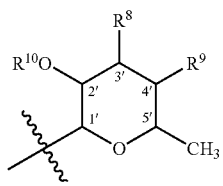   III wherein
R$^8$ and R$^9$ are both hydrogen or together form a bond, or R$^9$ is hydrogen and R$^8$ is —N(CH$_3$)R$^y$, wherein
R$^y$ is R$^P$, R$^z$ or —C(O)R$^z$, wherein R$^z$ is hydrogen or alkyl or alkenyl or cycloalkyl or aryl or heteroaryl or alkyl substituted with C$_2$–C$_7$-alkyl, C$_2$–C$_7$-alkenyl, C$_2$–C7-alkynyl, aryl or heteroaryl;
R$^{10}$ is hydrogen or R$^P$;
S$^2$ sugar moiety of Formula IV:

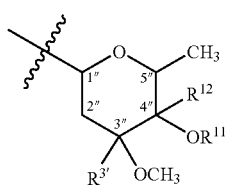   IV wherein
R$^{3'}$ is hydrogen or methyl;
R$^{11}$ is hydrogen, R$^P$, or O—R$^{11}$ is a group that with R$^{12}$ and with C/4" carbon atom forms a >C=O or epoxy group;
R$^{12}$ is hydrogen or a group that with O—R$^{11}$ group and with C/4" carbon atom forms a >C=O or epoxy group;
(vi) R$^2$ is hydrogen hydroxy, OR$^P$ or alkoxy;
(vii) A is hydrogen or methyl;
(viii) B is methyl or epoxy;
(ix) E hydrogen or halogen;
R$^3$ is hydroxy, OR$^P$, alkoxy or R$^3$ is a group that with R$^5$ and with C/11 and C/12 carbon atoms forms a cyclic carbonate or carbamate, or if W or Z is >N—R$_N$ R$^3$ is a group at with W or Z forms a cyclic carbamate;
(xi) R$^4$ is C$_1$–C$_4$ alkyl;
(xii) R$^5$ is hydrogen hydroxy, OR$^P$, C$_1$–C$_4$ alkoxy, or a group that with R$^3$ and with C/11 an C/12 carbon atoms forms a cyclic carbonate or carbamate;
(xiii) R$^6$ is hydrogen or C$_1$–C$_4$-alkyl; and R$^P$ is hydroxyl or amino protective group;

wherein M has a linkage site through which it is linked to S via linking group L; provided that linkage site is at one or more of the following:
a) any reactive hydroxy, nitrogen, or epoxy group located on S$^1$, S$^2$, or an aglycone oxygen if S$^1$ and/or S$^2$ is cleaved off;
b) a reactive >N—R$_N$ or —NR$_t$R$_s$ or oxo group located on Z or W;
c) a reactive hydroxy group located at any one of R$^1$, R$^2$, R$^3$, and R$^5$;
d) any other group that can be first derivatized to a hydroxy or —NR$_t$R$_s$ group and L represents a group of Formula VA or of Formula VB:

$$X^1—(CH_2)_m—X^2 \quad\quad VA$$

$$X^1—(CH_2)_m\text{-}Q\text{-}(CH_2)_n—X^2 \quad\quad VB$$

wherein
X$^1$ is selected from: —CH$_2$—, —CH$_2$NH—, —C(O)—, —OC(O)—, =N—O— or —OC(O)NH—;
—C(O)NH;
X$^2$ is —NH— or —NHC(O)— or —CH$_2$—;
Q is —NH— or —CH$_2$—, wherein
each —CH$_2$— or —NH— group may be optionally substituted by C$_1$–C$_7$-alkyl, C$_2$–C$_7$-alkenyl, C$_2$–C$_7$-alkynyl, C(O)R$^x$, C(O)OR$^x$, C(O)NHR$^x$, wherein R$^x$ is C$_1$–C$_7$-alkyl, aryl or heteroaryl;
the symbols m and n independently are a whole number from 0 to 8, with the proviso that if Q is NH, n cannot be 0;

S represents a group of Formula X:

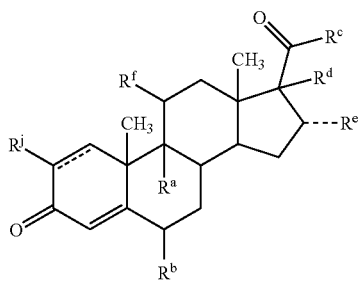

wherein $R^a$ and $R^b$ independently represents, hydrogen or halogen;

$R^c$ is hydroxy, alkoxy, alkyl, thiocarbamoyl, carbamoyl or a valence-bond;

$R^d$ and $R^e$ independently represents: hydrogen, hydroxy, methyl or alkoxy or each are a group that forms a 1,3-dioxolane ring with the other or a valence bond;

$R^f$ is hydrogen, hydroxy, chloro, or forming a keto group with the carbon atom it is attached to;

$R^j$ is hydrogen or halogen;

or a pharmaceutically acceptable salt or solvate thereof.

3. The compound according to claim 2 wherein

Z is $>NR_N$, wherein $R_N$ is hydrogen or a methyl group;

W is $>CH_2$;

B is methyl;

E is hydrogen;

$R^2$ is hydroxy;

A is methyl;

$S^1$ group represents a group of Formula III wherein $R^8$ is selected from: hydrogen, amino, N-metylamino, N,N-dimethylamino, N-methyl-N-$(C_2–C_4)$-alkylamino, N-methyl-N-methylcarbonylamino, N-methyl-N-benzylamino, N-methyl-N-cyclohexylamino;

$R^9$ and $R^{10}$ are hydrogen;

$R^1$ is O—$S^2$ wherein $S^2$ represents a group of Formula IV wherein $R^{11}$ and $R^{12}$ are hydrogen and $R^{13}$ is methyl;

U is hydrogen;

Y is methyl;

$R^4$ is methyl;

$R^6$ is ethyl;

$R^5$ is hydroxy or a group that with $R^3$ and with C/11 and C/12 carbon atoms forms a cyclic carbonate bridge;

$R^3$ is hydroxy or a group that with $R^5$ and with C/11 and C/12 carbon atoms forms a cyclic carbonate bridge;

provided that the linkage through the nitrogen of Z at N/9a position or through the oxygen of $R^3$ at C/11 position.

4. The compound according to claim 2 wherein

Z is selected from >N—H, >N—$CH_3$, >N—C(O)$NHR^x$, wherein $R^x$ is isopropyl;

W is $>C=O$ or $>CH_2$ provided that when Z is >N—$CH_3$ W cannot be $>C=O$;

B is methyl;

E is hydrogen;

A is methyl;

$R^2$ is hydroxy or methoxy;

$S^1$ group represents a group of Formula III wherein $R^8$ is selected from: amino, $C_1$–$C_6$-alkylamino, $C_1$–$C_6$-dialkylamino;

$R^9$ and $R^{10}$ are hydrogen;

$R^1$ is O—$S^2$ wherein $S^2$ represents a group of Formula IV wherein $R^{11}$ is hydrogen or O—$R^{11}$ is a group that with $R^{12}$ and with C/4" carbon atom forms a $>C=O$ or epoxy group; $R^{12}$ is hydrogen or a group that with O—$R^{11}$ group and with C/4" carbon atom forms a $>C=O$ or epoxy group; $R^{13}$ is methyl;

U is hydrogen;

Y is methyl;

$R^3$ is hydroxy;

$R^4$ methyl;

$R^5$ is hydroxy or methoxy;

$R^6$ ethyl;

provided that the linkage through the nitrogen of $R^8$ at C/3', through the oxygen of $R^2$ at C/6 or through the carbon of $R^{12}$ or through the oxygen of $R^{11}$ both at C/4".

5. The compound according to claim 2 wherein $R^a$ and $R^b$ independently presents, hydrogen or halogen;

$R^d$ is hydrogen or hydroxy;

$R^e$ is methyl;

$R^f$ is hydroxy;

Rj is hydrogen provided that the linkage is through the valence bond $R^C$.

6. A compound of the formula

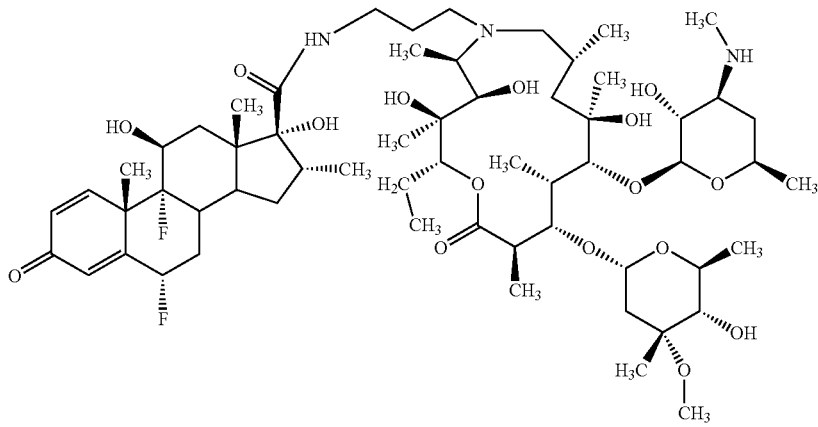

or a pharmaceutically acceptable salt or solvate thereof.

7. A compound of the formula
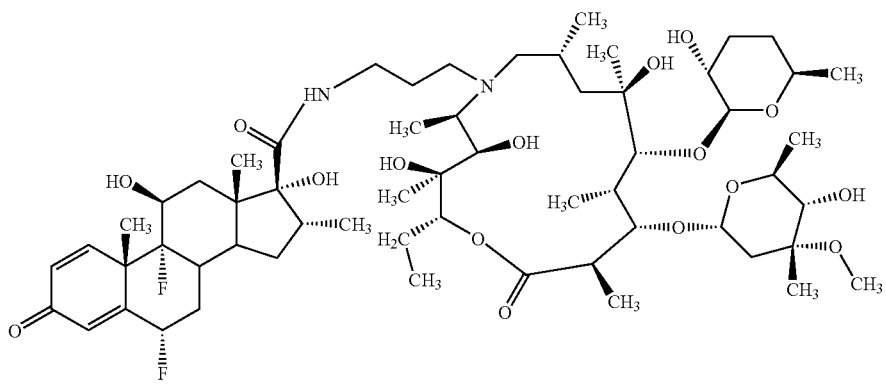
or a pharmaceutically acceptable salt or solvate thereof.
8. A compound of the formula
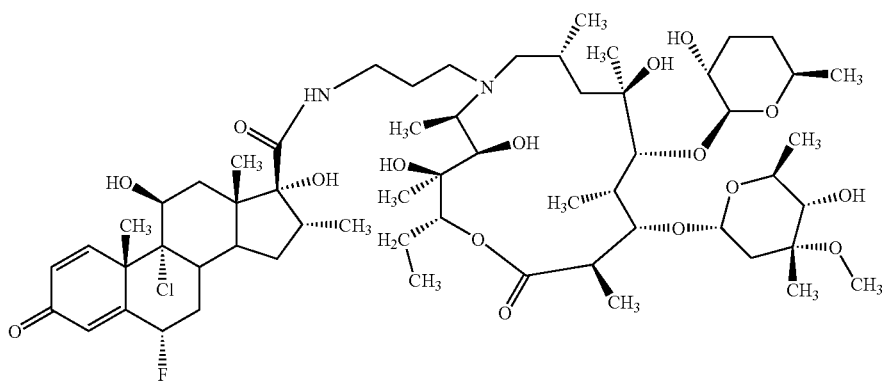
or a pharmaceutically acceptable salt or solvate thereof.
9. A compound of the formula
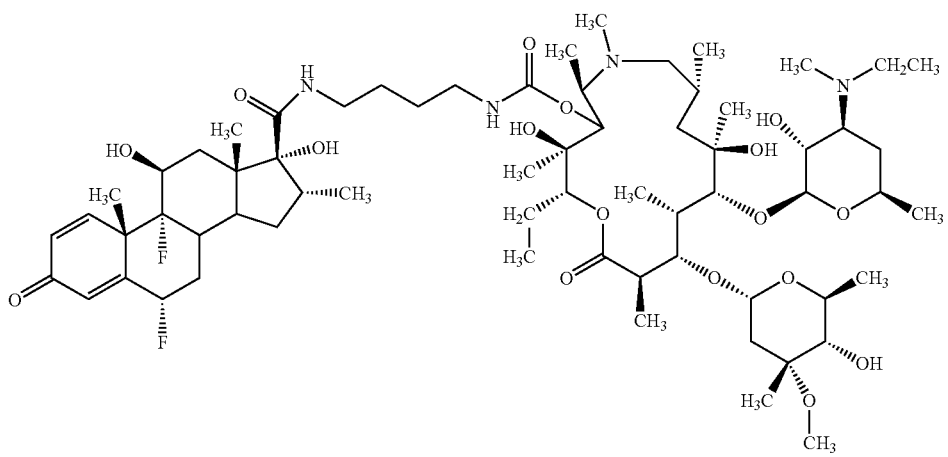
or a pharmaceutically acceptable salt or solvate thereof.

10. A compound of the formula
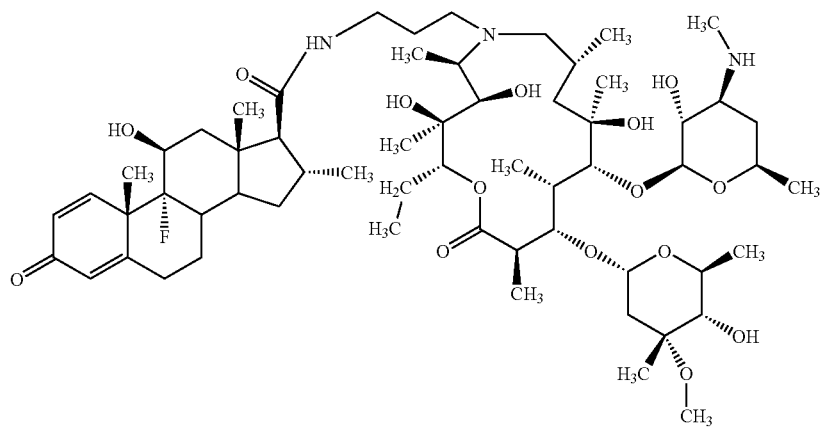
or a pharmaceutically acceptable salt or solvate thereof.
11. A compound of the formula
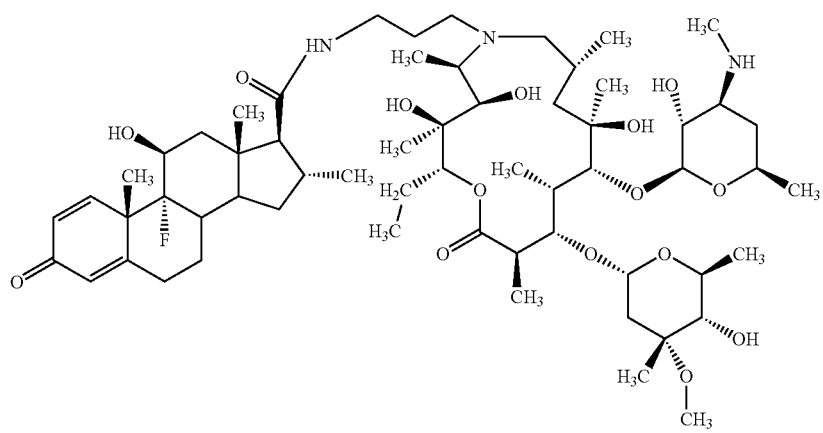
or a pharmaceutically acceptable salt or solvate thereof.
12. A compound of the formula
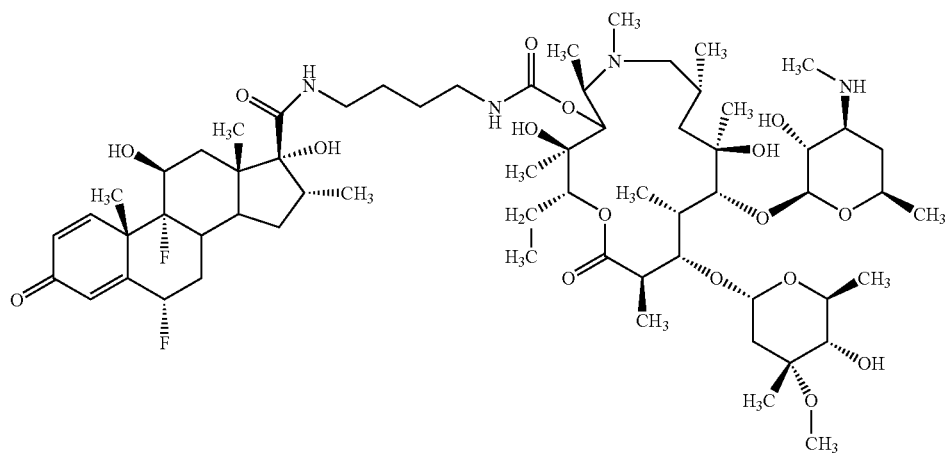
or a pharmaceutically acceptable salt or solvate thereof.

13. A compound of the formula
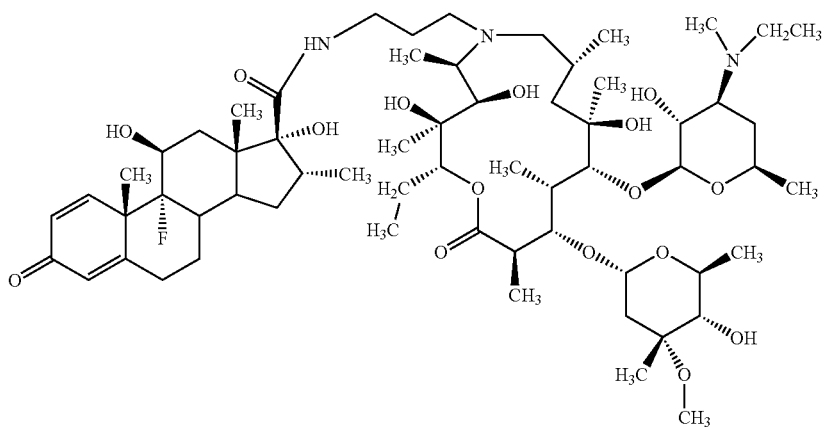
or a pharmaceutically acceptable salt or solvate thereof.
14. A compound of the formula
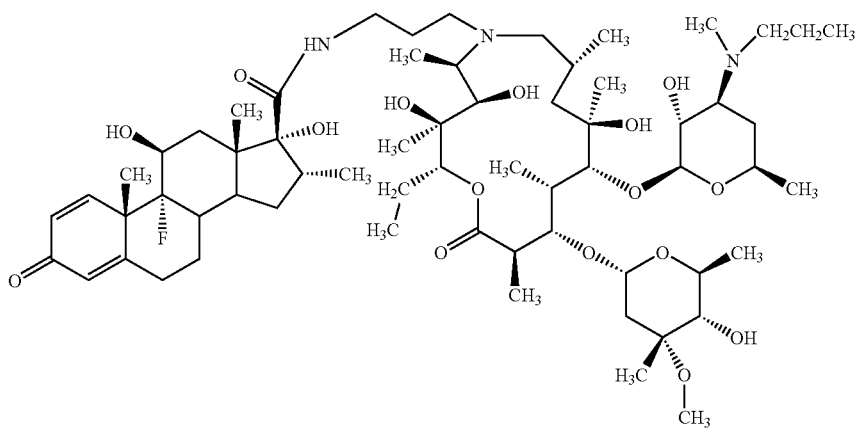
or a pharmaceutically acceptable salt or solvate thereof.
15. A compound of the formula
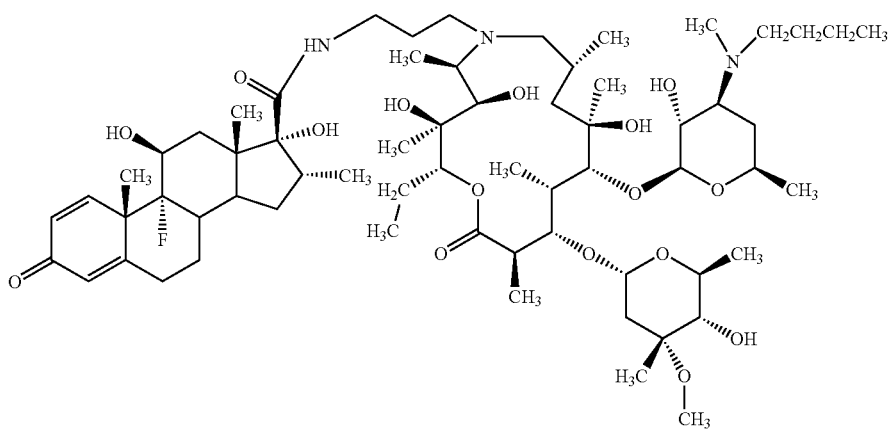
or a pharmaceutically acceptable salt or solvate thereof.

16. A compound of the formula
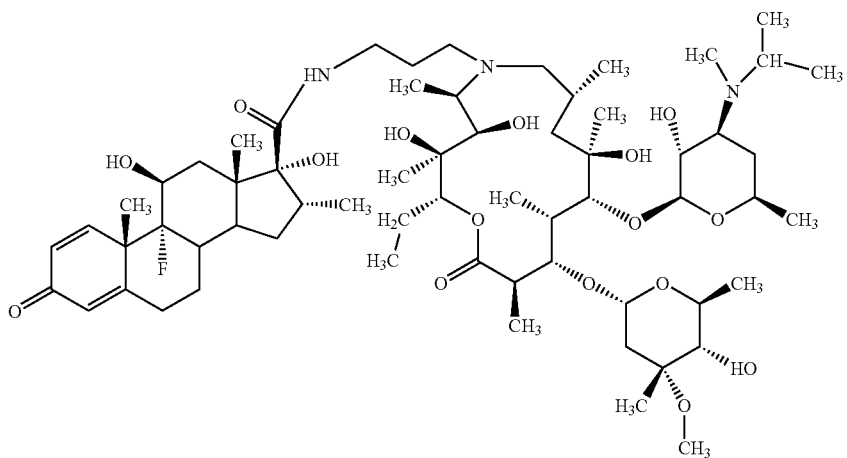
or a pharmaceutically acceptable salt or solvate thereof.
17. A compound of the formula
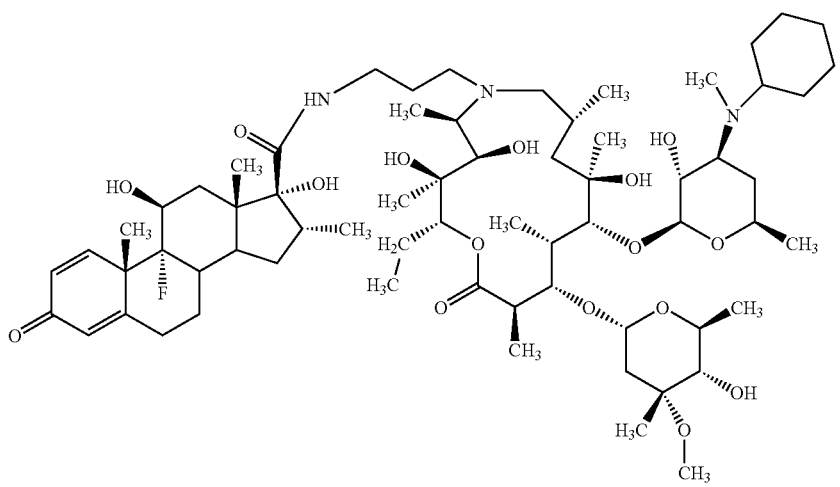
or a pharmaceutically acceptable salt or solvate thereof.
18. A compound of the formula
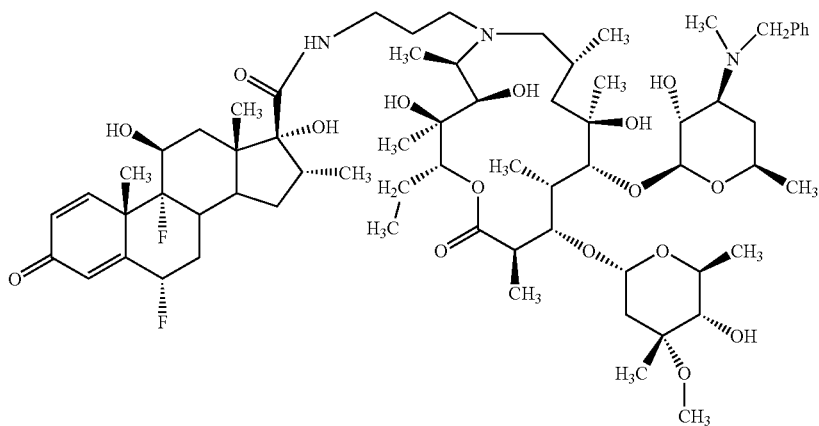
or a pharmaceutically acceptable salt or solvate thereof.

19. A compound of the formula
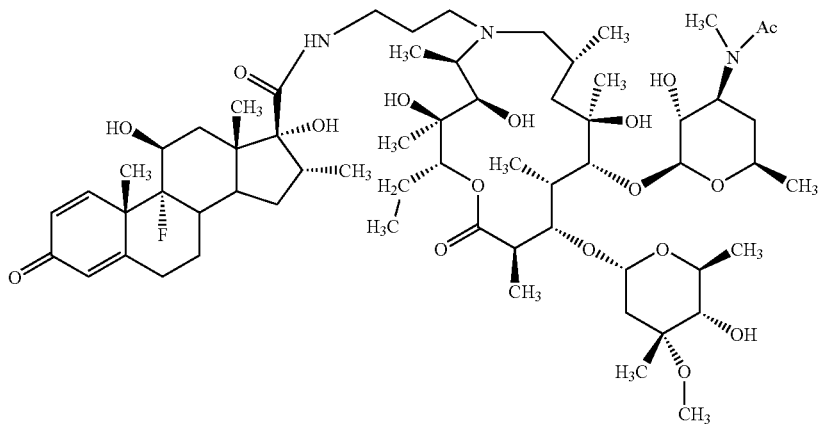
or a pharmaceutically acceptable salt or solvate thereof.
20. A compound of the formula
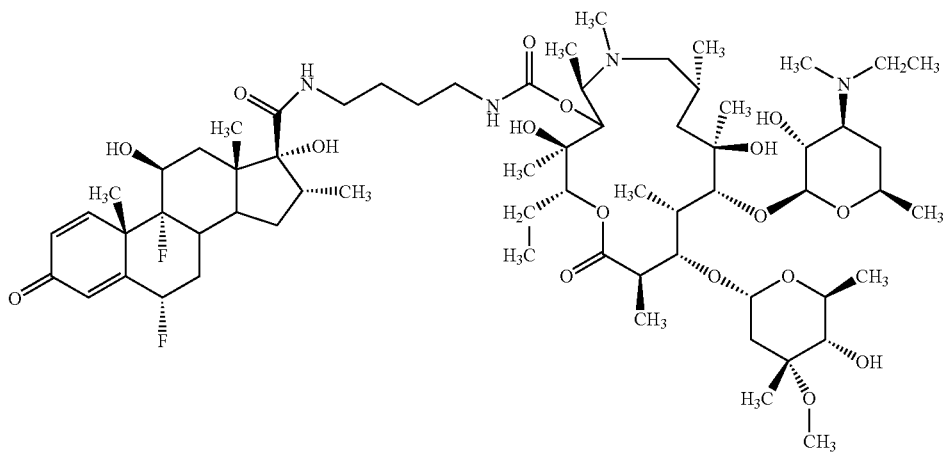
or a pharmaceutically acceptable salt or solvate thereof.
21. A compound of the formula
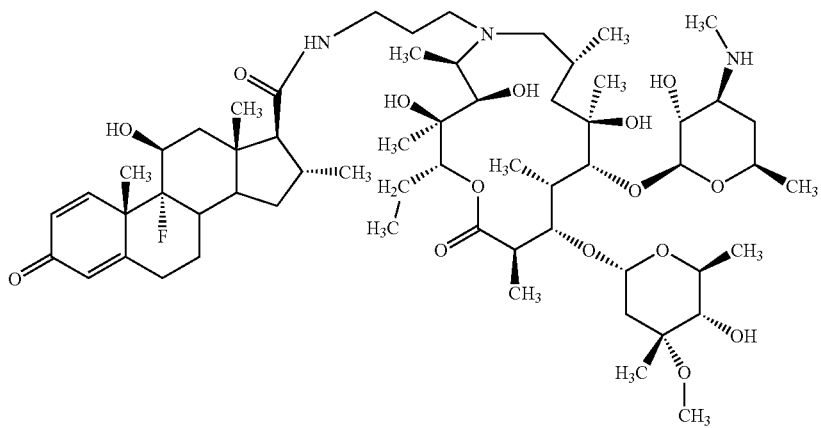
or a pharmaceutically acceptable salt or solvate thereof.

22. A compound of the formula
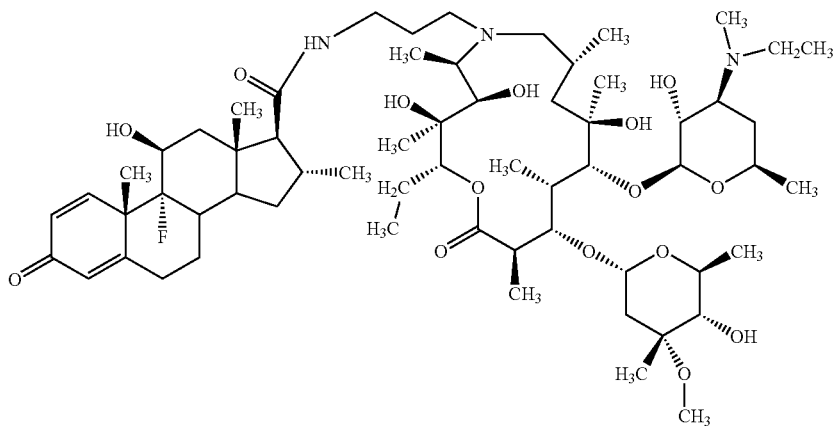
or a pharmaceutically acceptable salt or solvate thereof.
23. A compound of the formula
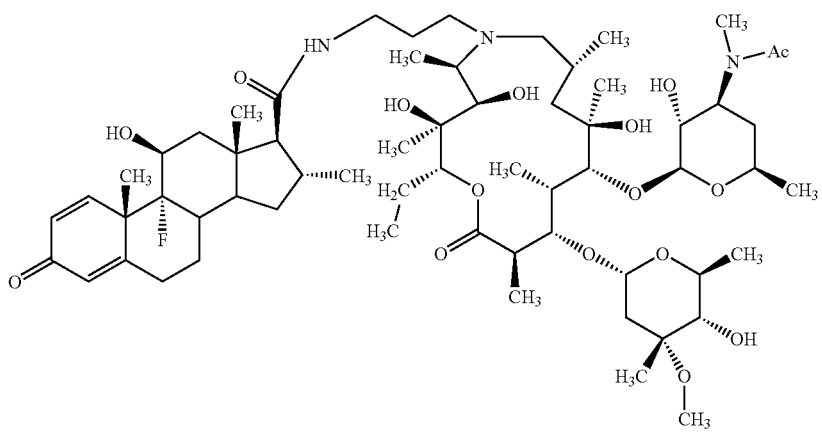
or a pharmaceutically acceptable salt or solvate thereof.
24. A compound of the formula
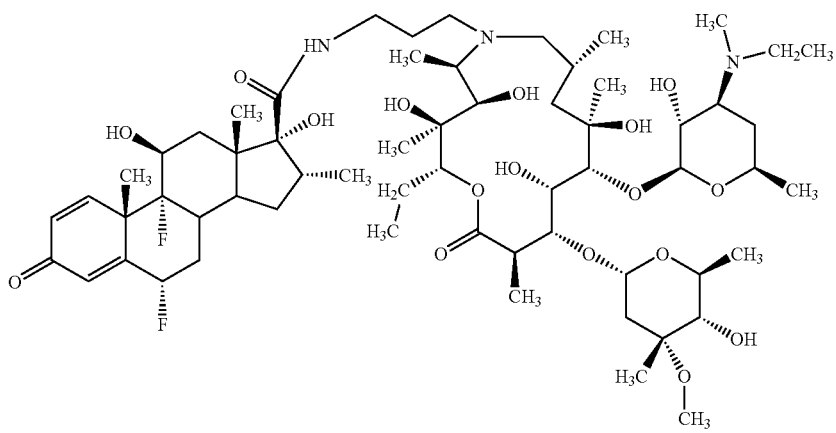
or a pharmaceutically acceptable salt or solvate thereof.

25. A compound of the formula
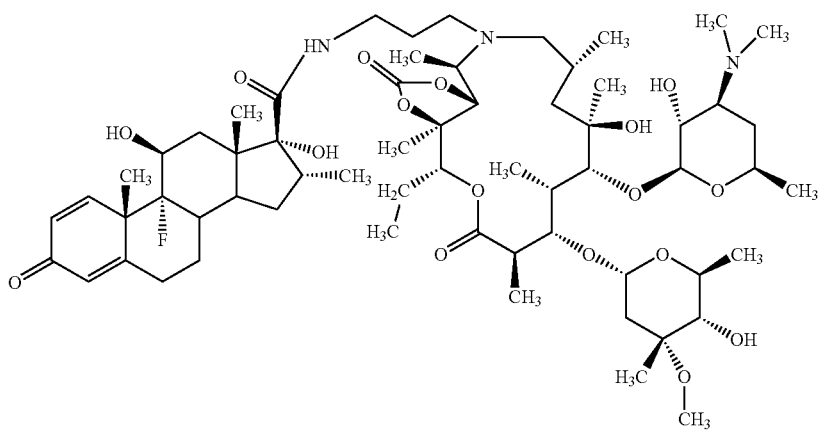
or a pharmaceutically acceptable salt or solvate thereof.
26. A compound of the formula
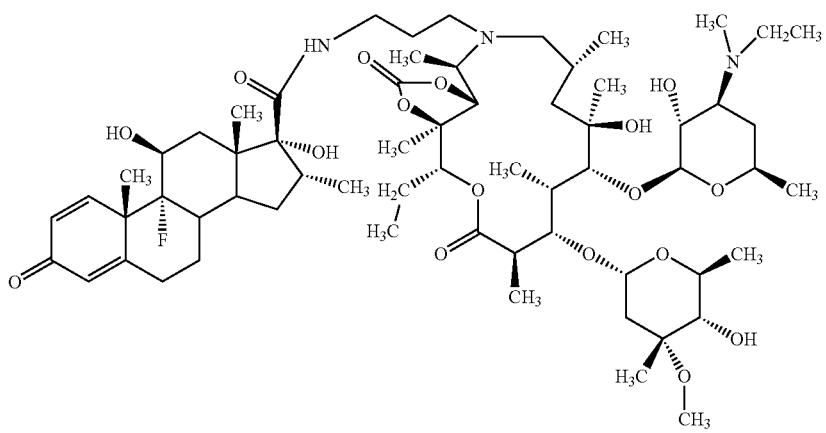
or a pharmaceutically acceptable salt or solvate thereof.
27. A compound of the formula
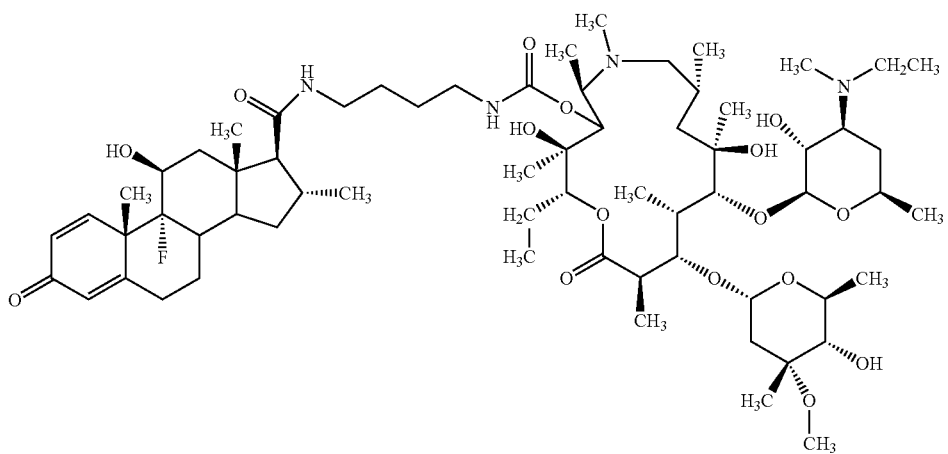
or a pharmaceutically acceptable salt or solvate thereof.

28. A compound of the formula
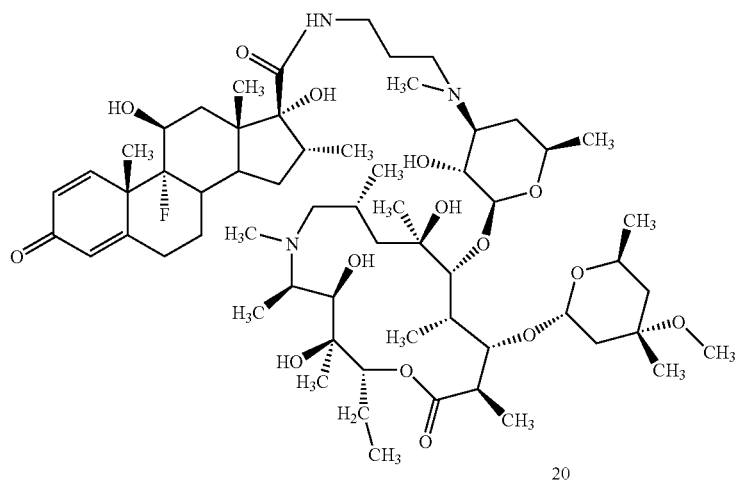
or a pharmaceutically acceptable salt or solvate thereof.
29. A compound of the formula
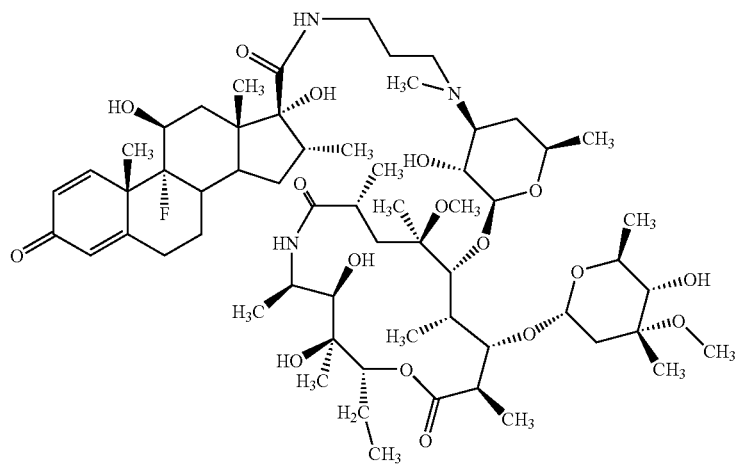
or a pharmaceutically acceptable salt or solvate thereof.
30. A compound of the formula
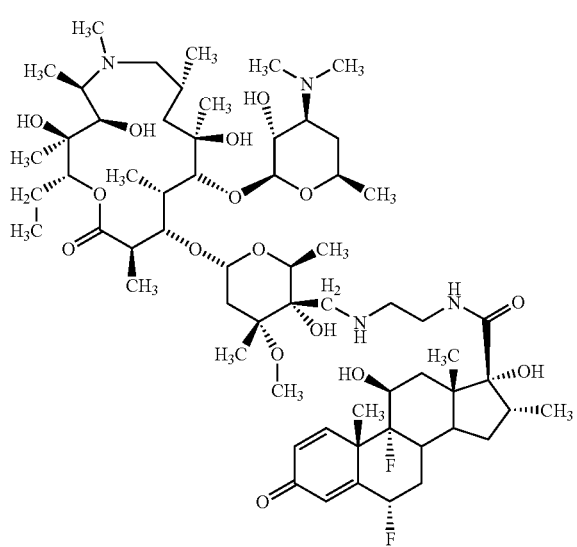
or a pharmaceutically acceptable salt or solvate thereof.
31. A compound of the formula
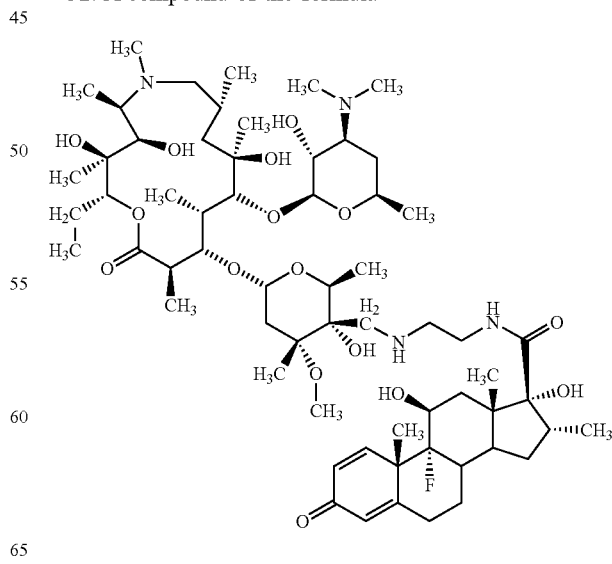
or a pharmaceutically acceptable salt or solvate thereof.

32. A compound of the formula

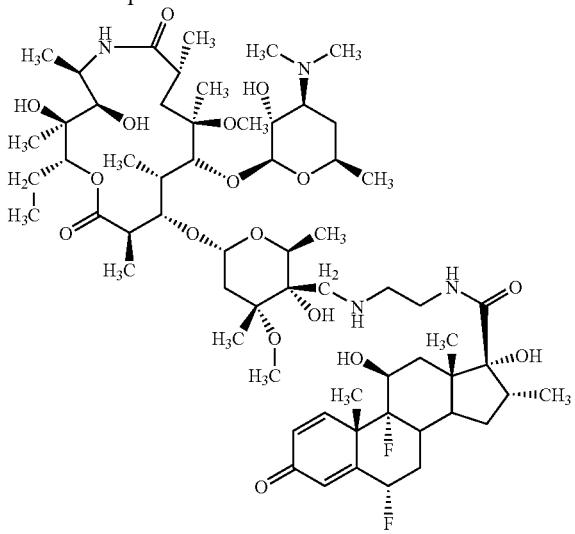

or a pharmaceutically acceptable salt or solvate thereof.

33. A compound of the formula

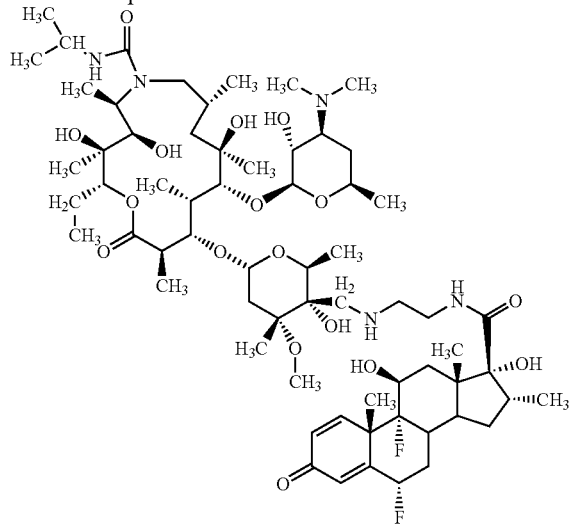

or a pharmaceutically acceptable salt or solvate thereof.

34. A compound of the formula

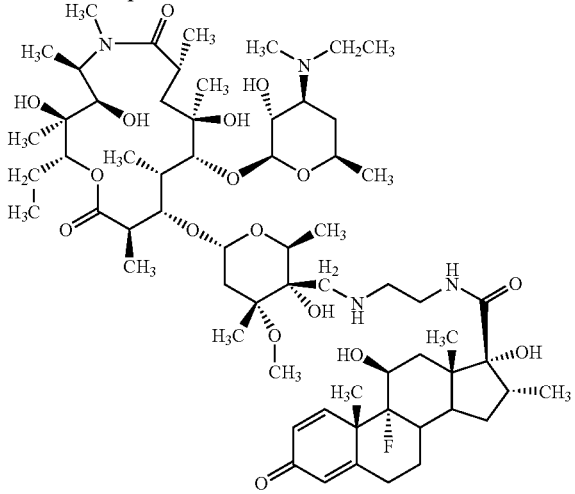

or a pharmaceutically acceptable salt or solvate thereof.

35. A compound of the formula

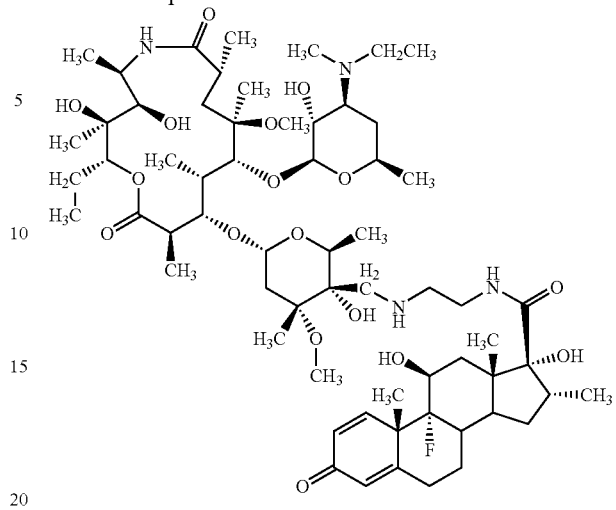

or a pharmaceutically acceptable salt or solvate thereof.

36. A compound of the formula

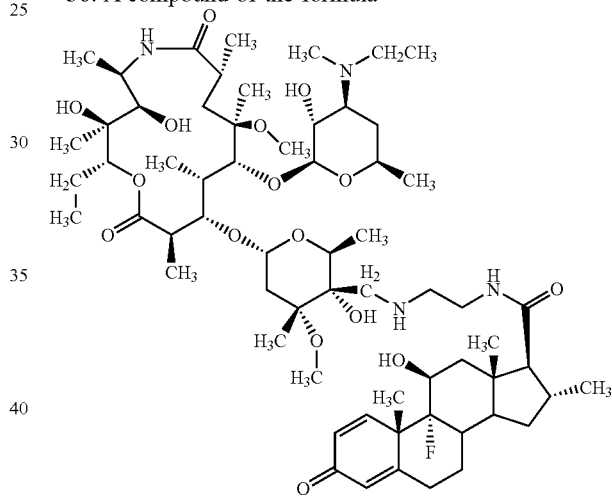

or a pharmaceutically acceptable salt or solvate thereof.

37. A compound of the formula

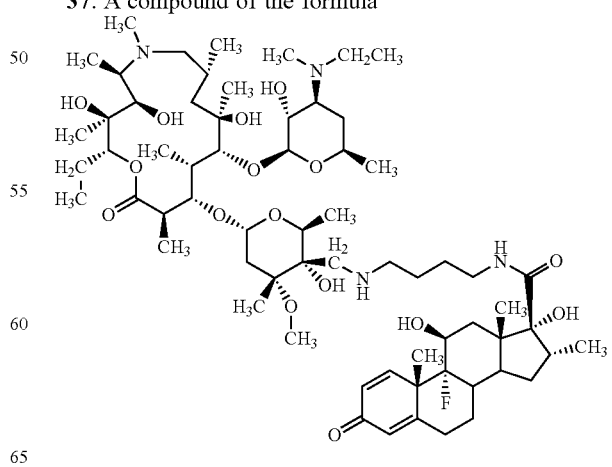

or a pharmaceutically acceptable salt or solvate thereof.

38. A compound of the formula
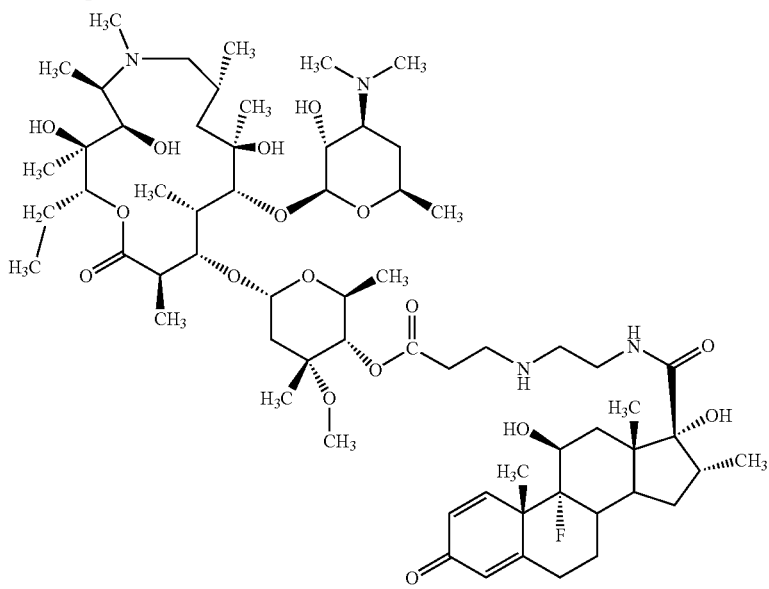
or a pharmaceutically acceptable salt or solvate thereof.
39. A compound of the formula
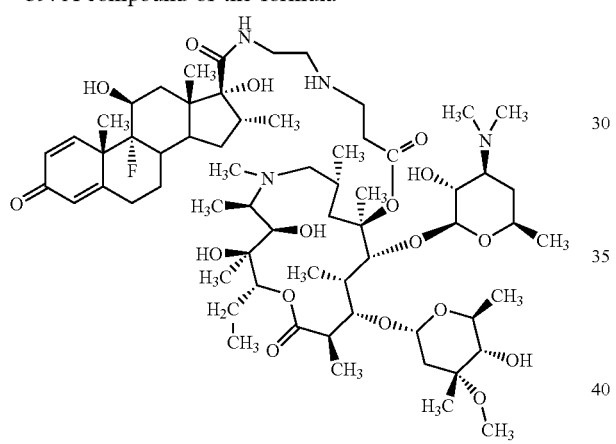
or a pharmaceutically acceptable salt or solvate thereof.
40. A compound of the formula
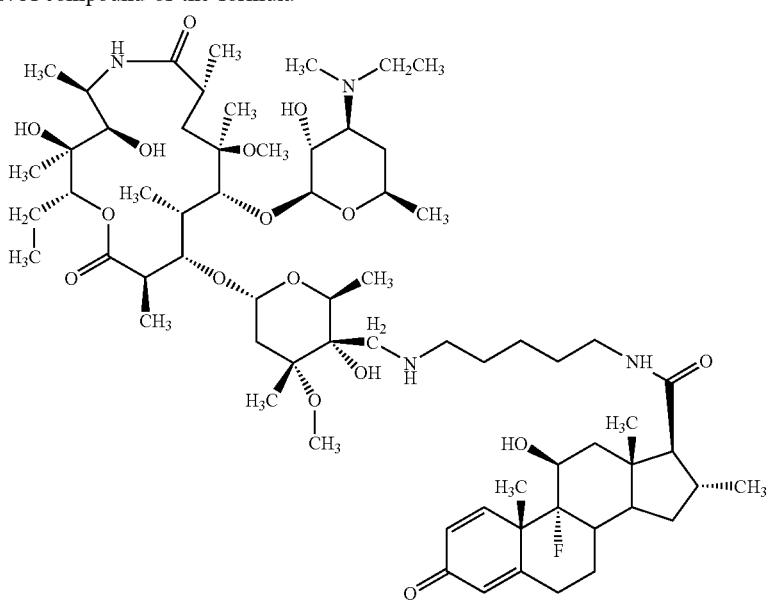

or a pharmaceutically acceptable salt or solvate thereof.
41. A compound of the formula
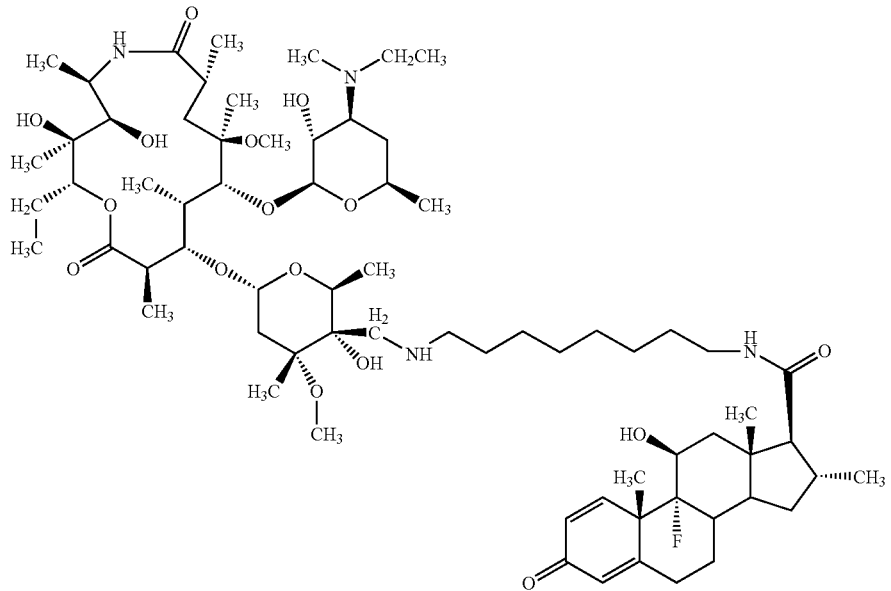
or a pharmaceutically acceptable salt or solvate thereof.
42. A compound of the formula
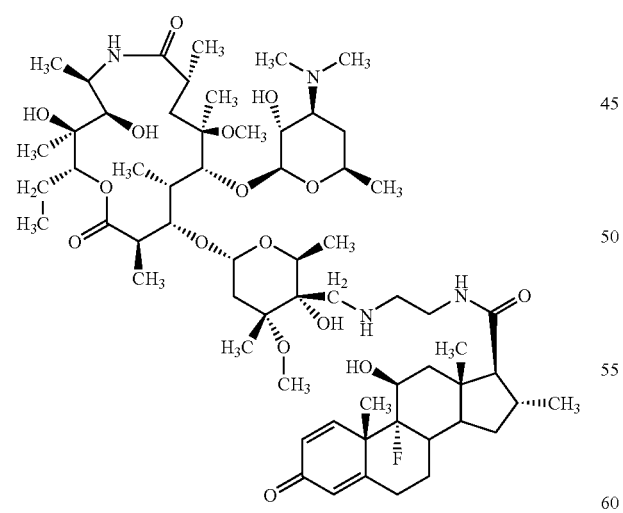
or a pharmaceutically acceptable salt or solvate thereof.

43. A compound of the formula
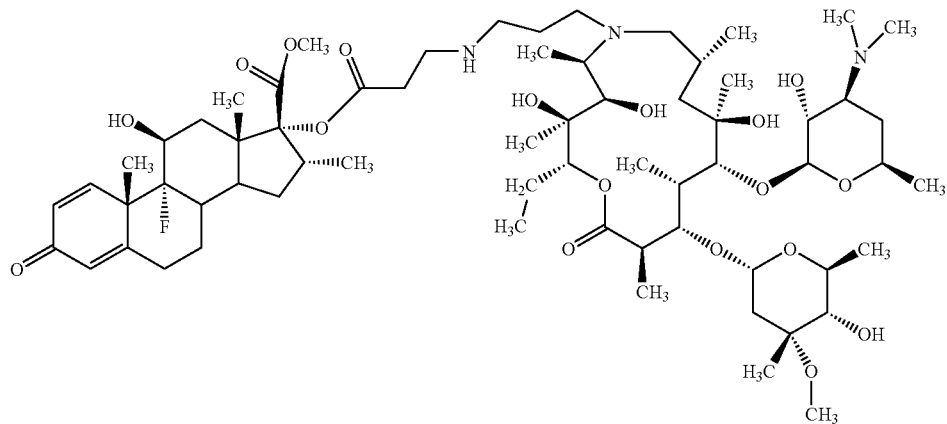
or a pharmaceutically acceptable salt or solvate thereof.
44. A compound of the formula
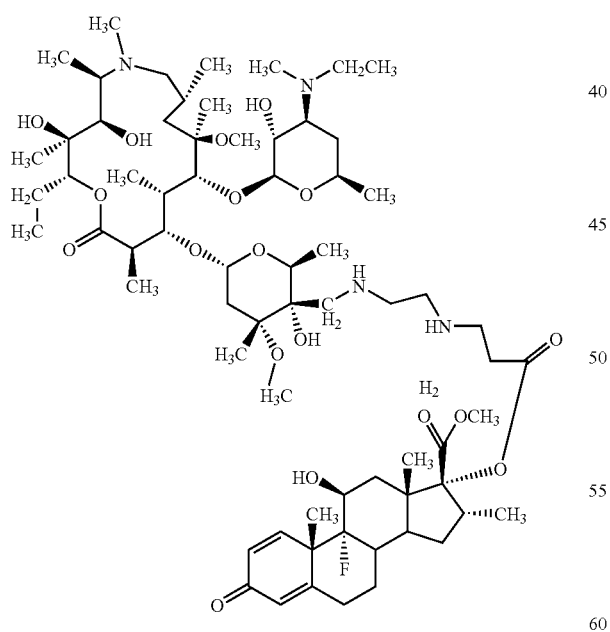
or a pharmaceutically acceptable salt or solvate thereof.

45. A compound of the formula

[chemical structure]

or a pharmaceutically acceptable salt or solvate thereof.

46. A process for the preparation for a compound of Formula I:

[structure: M—L—S]  I wherein M represents a group of Formula II:

[structure of Formula II]  II wherein (i) Z and W independently are >C=O, >CH$_2$, >CH—NR$_t$R$_s$, >N—R$_N$ or >CH—R$_M$, wherein R$_t$ and R$_s$ independently are hydrogen or alkyl;

R$_M$ is hydroxy, alkoxy, substituted alkoxy or OR$^p$;

R$_N$ is hydrogen, R$^p$, alkyl, alkenyl, alkynyl, alkoxy, alkoxyalkyl, or —C(X)—NR$_t$R$_s$; wherein X is =O or =S;

provided that Z and W cannot both simultaneously be, >C=O, >CH$_2$, >CH—NR$_t$R$_s$, >N—R$_N$, >C=N—R$_M$ or a bond;

(ii) U and Y independently are hydrogen, halogen, alkyl, or hydroxyalkyl;

(iii) R$^1$ is hydroxy, OR$^p$, —O—S$^2$ group or an =O;

(iv) S$^1$ is a sugar moiety of Formula III:

[structure of Formula III]  III wherein

R$^8$ and R$^9$ are both hydrogen or together form a bond, or R$^9$ is hydrogen and R$^8$ is —N(CH$_3$)R$^y$, wherein R$^y$ is R$^p$, R$^z$ or —C(O)R$^z$, wherein R$^z$ is hydrogen or alkyl or alkenyl or alkynyl or cycloalkyl or aryl or heteroaryl or alkyl substituted with C$_2$–C$_7$-alkyl, C$_2$–C$_7$-alkenyl, C$_2$–C$_7$-alkynyl, aryl or heteroaryl;

R$^{10}$ is hydrogen or R$^p$;

S$^2$ sugar moiety Formula IV:

[structure of Formula IV]  IV wherein

R$^{3'}$ is hydrogen or methyl;

R$^{11}$ is hydrogen, R$^p$, or O—R$^{11}$ is a group that with R$^{12}$ and with C/4" carbon atom forms a >C=O or epoxy group;

R$^{12}$ is hydrogen or a group that with O—R$^{11}$ group and with C/4" carbon atom forms a >C=O or epoxy group;

(vi) R$^2$ is hydrogen, hydroxy, O—R$^p$ or alkoxy;

(vii) A is hydrogen or methyl;

(viii) B is methyl or epoxy;

(ix) E is hydrogen or halogen;

$R^3$ is hydroxy, $OR^p$, alkoxy or $R^3$ is a group that with $R^5$ and with C/11 and C/12 carbon atoms forms a cycle carbonate or carbamate, or if W or Z is >N—$R_N R^3$ is a group that with W or Z forms a cyclic carbamate;

(xi) $R^4$ is $C_1$–$C_4$ alkyl;

(xii) $R^5$ is hydrogen, hydroxy, $OR^p$, $C_1$–$C_4$ alkoxy, or a group that with $R^3$ and with C/11 and C/12 carbon atoms forms a cyclic carbonate or carbamate;

(xiii) $R^6$ is hydrogen or $C_1$–$C_4$-alkyl; and $R^p$ is hydroxyl or amino protective group;

wherein M has a linkage site though which it is linked to S via linking group L; provided that the linkage site is at one or more of the following:

a) any reactive hydroxy, nitrogen, or epoxy group located on $S^1$, $S^2$, or an aglycone oxygen if $S^1$ and/or $S^2$ is cleaved off;

b) a reactive >N—$R_N$ or —$N_r R_s$ or oxo group located on Z or W;

c) a reactive hydroxy group located at any one of $R^1$, $R^1$, $R^3$, and $R^5$;

d) any other group that can be first derivatized to a hydroxy or —$NR_r R_s$ group; and L represents a group of Formula VA or of Formula VB:

wherein $X^1$ is selected from: —$CH_2$—, —$CH_2NH$—, —C(O)—, —OC(O)—, =N—O— or —OC(O)NH—; —C(O)NH;

$X^2$ is —NH— or —NHC(O)— or —$CH_2$—;

Q is —NH— or —$CH_2$—, wherein each —$CH_2$— or —NH— group may be optionally substituted by $C_1$–$C_7$-alkyl, $C_2$–$C_7$-alkenyl, $C_2$–$C_7$-alkynyl, $C(O)R^x$, $C(O)OR^x$, $C(O)NHR^x$, wherein $R^x$ is $C_1$–$C_7$-alkyl, aryl or heteroaryl;

the symbols m and n independently are a whole number from 0 to 8, with the proviso that if Q is NH, n cannot be 0;

S represents a group of Formula X:

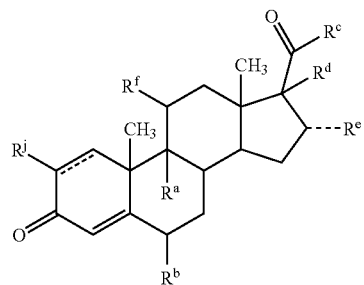

wherein $R^a$ and $R^b$ independently represents, hydrogen or halogen;

$R^c$ is hydroxy, alkoxy, alkyl, thiocarbamoyl, carbamoyl or a valence-bond;

$R^d$ and $R^e$ independently represents: hydrogen, hydroxy, methyl or $C_1$–$C_4$-alkoxy or each are a group that forms a 1,3-dioxolane ring with the other or a valence bond;

$R^f$ is hydrogen, hydroxy, chloro, or forming a keto group with the carbon atom it is attached to;

$R^j$ is hydrogen or halogen;

or a pharmaceutically acceptable salt or solvate;

a) for a compound represented by Formula I comprising the steps of:

where $X^2$ is —NHC(O)—, by reacting a compound of Formula V:

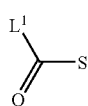

V wherein $L^1$ represents a leaving group, and a free amino group of a macrolide represented by Formula VId:

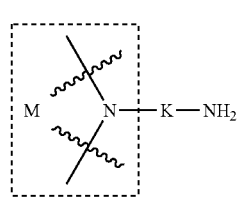

VId b) for a compound represented by Formula I, where $X^2$ is —OC(O)—, by reacting a compound of Formula V and a hydroxyl group of a macrolide represented by Formula VIe:

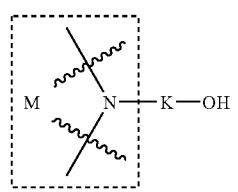

VIe c) for a compound represented by Formula I, wherein $X^1$ is —OC(O)—, Q is NH and $X^2$ is —NHC(O)—, by reacting a macrolide represented by:

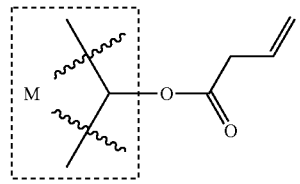

and a free amino group of the compound represented by Formula IVc:

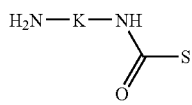

IVc d) for a compound represented by Formula I, where $X^1$ is —OC(O)NH— and $X^2$ is —NHC(O)—, by reacting a macrolide represented by Formula VII and a free amino group of Formula IVc:

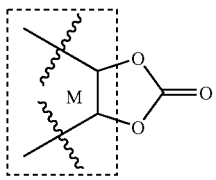
VII e) for a compound represented by Formula I, $X^1$ is —$CH_2$—, Q is —NH— and $X^2$ is —NHC(O)—, by reacting macrolide represented by Formula Va and a compound of Formula V:

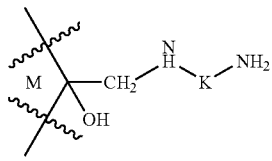
Va f) compound of Formula I by reacting a macrolide represented by Formula VIf or by Formula VIg or by Formula VIh having a leaving group

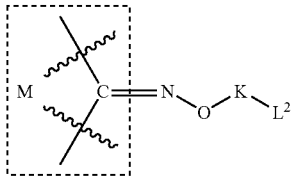
VIh

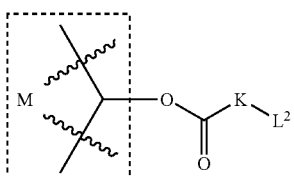
VIf

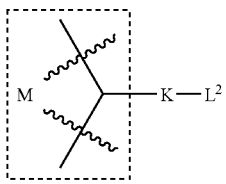
VIg with a free carboxyl acid of steroid represented by Formula IVb

IVb g) for a compound represented by Formula I, wherein X1 is —OC(O)—, Q is NH and $X^2$ is —NH— by reacting a macrolide represented by:

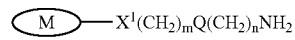
VId and a steroid subunit having a —C═C— bond represented by Formula Sb:

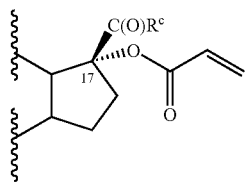
Sb following by modification of $R^c$ group.

47. A pharmaceutical composition comprising a compound according to claim 1 or a pharmaceutically acceptable salt or solvate thereof as well as pharmaceutically acceptable diluent or carrier.

48. A method of treatment of inflammatory diseases, disorders or conditions characterized by or associated with an undesirable inflammatory immune response, and all diseases and conditions induced by or associated with an excessive secretion of TNF-α and IL-1 which comprises administering to a subject in need of treatment a therapeutical effective amount of a compound according to claim 1.

49. A method of treating inflammatory conditions or immune or anaphylactic disorders associated with infiltration of leukocytes into inflamed tissue in a subject in need thereof which comprises administering to said subject a therapeutically effective amount of a compound according to claim 1.

50. The method according to claim 49, wherein inflammatory conditions and immune disorders are selected from the group consisting of asthma, adult respiratory distress syndrome, bronchitis, and cystic fibrosis.

51. A method according to claim 49, wherein said inflammatory conditions and immune disorders are selected from the group consisting of inflammatory conditions or immune disorders of the lungs, joints, eyes, bowel, skin, and heart.

52. A method according to claim 49, wherein said inflammatory conditions and immune disorders are selected from the group consisting of asthma, adult respiratory distress syndrome, bronchitis, cystic fibrosis, rheumatoid arthritis, rheumatoid spondylitis, osteoarthritis, gouty arthritis, uveitis, conjunctivitis, inflammatory bowel conditions, Crohn's disease, ulcerative colitis, distal proctitis, psoriasis, eczema, dermatitis, coronary infarct damage, chronic inflammation, endotoxin shock, and smooth muscle proliferation disorders.

53. A pharmaceutical composition comprising a compound according to claim 2, or pharmaceutically acceptable salt or solvate thereof as well as pharmaceutically acceptable diluent or carrier.

54. A method of treatment of inflammatory diseases, disorders conditions characterized by or associated with an undesirable inflammatory immune response, and all diseases and conditions induced by or associated with an excessive secretion of TNF-α and IL-1 which comprises administering to a subject in need of treatment a therapeutically effective amount of a compound according to claim 2.

55. A method of treating inflammatory conditions or immune or anaphylactic disorders associated with infiltration of leukocytes into inflamed tissue in a subject in need thereof which comprises administering to said subject a therapeutically effective amount of a compound according to claim 2.

56. The method according to claim 55, wherein inflammatory conditions and immune disorders are selected from the group consisting of asthma, adult respiratory distress syndrome, bronchitis, and cystic fibrosis.

57. A method according to claim 55, wherein said inflammatory conditions and immune disorders are selected from the group consisting of inflammatory conditions or immune disorders of the lungs, joints, eyes, bowel, skin, and heart.

58. A method according to claim 55, wherein said inflammatory conditions and immune disorders are selected from the group consisting of asthma, adult respiratory distress syndrome, bronchitis, cystic fibrosis rheumatoid arthritis, rheumatoid spondylitis, osteoarthritis, gouty arthritis, uveitis, conjunctivitis, inflammatory bowel conditions, Crohn's disease, ulcerative colitis distal proctitis, psoriasis, eczema, dermatitis, coronary infarct damage, chronic inflammation, endotoxin shock, and smooth muscle proliferation disorders.

59. A compound of the formula:

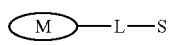

I wherein M represents a group of Formula II:

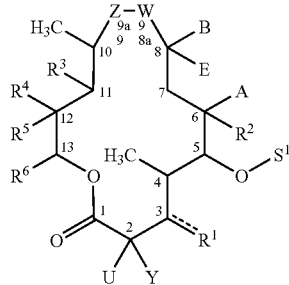

II wherein (i) Z and W independently are >C=O, <CH-$NR_tR_s$, >N-$R_N$ or >C=N-$R_M$, wherein $R_t$ and $R_s$ independently are hydrogen or alkyl;

$R_M$ is hydrogen, $R_P$, alkyl, alkoxy, alkoxyalkyl, or -C(X)-$NR_tR_s$; wherein X is =O or =S;

provided that Z and W cannot both simultaneously be, >C=O, >CH$_2$, >CH-$NR_tR_s$, >N-$R_N$, >C=N-$R_M$ or a bond;

(ii) U an Y independently are hydrogen, halogen, alkyl, or hydroxyalkyl;

(iii) $R_1$ is hydroxy, $OR^p$, -O-$S^2$ group or an =O;

(iv) $S_1$ is a sugar moiety of Formula III:

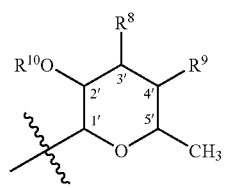

III wherein $R^8$ and $R^9$ are both hydrogen or together form a bond, or $R^9$ is hydrogen and $R^8$ is -N(CH$_3$)$R^y$, wherein $R^y$ is $R^z$ or -C(O)$R^z$, wherein $R^z$ is hydrogen or alkyl or alkenyl or alkynyl or cycloalkyl or aryl or heteroaryl or alkyl substituted with C$_2$-C$_7$-alkyl, C$_2$-C$_7$-alkenyl, C$_2$-C$_7$alkynyl, aryl or heteroaryl;

$R^{10}$ is hydrogen or $R^p$;

$S^2$ sugar moiety of Formula IV:

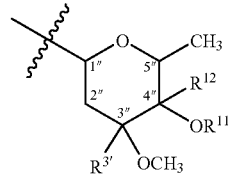

IV wherein $R^3$ is hydrogen or methyl;

$R^{11}$ is hydrogen, or $R^p$.

$R^{12}$ is hydrogen, (vi) $R^2$ is hydrogen, hydroxy, $OR^p$ or alkoxy;

(vii) A is hydrogen or methyl;

(viii) B is methyl or epoxy;

(ix) E is hydrogen or halogen;

$R^3$ is hydroxy, $OR^p$, alkoxy or $R^3$ is a group that with $R^5$ forms a cyclic carbonate or carbamate, or if W or Z is >N-$R_N$ $R^3$ is a group that with W or Z forms a cyclic carbamate;

(xi) $R^4$ is C$_1$-C$_4$ alkyl;

(xii) $R^5$ is hydrogen, hydroxy, $OR^p$, C$_1$-C$_4$ alkoxy, or a group that with $R^3$ forms a cyclic carbonate or carbamate;

(xiii) $R^6$ is hydrogen or C$_1$-C$_4$-alkyl;

$R^p$ is a protective group wherein M has a linkage site through which it is linked to S via linking group L; provided that the linkage site being at one or more of the following:

a) any reactive hydroxy, nitrogen, or epoxy group located on $S^1$, $S^2$, or an aglycone oxygen if $S^1$ and/or $S^2$ is cleaved off;

b) a reactive >N-$R_{N\ or\ -NR_t}R_s$ or oxo group located on Z or W;

c) a reactive hydroxy group located at any one of $R^1$, $R^2$, $R^3$, and $R^5$;

d) any other group that can be first derivatized to a hydroxy or -$NR_tR_s$group of Formula X:

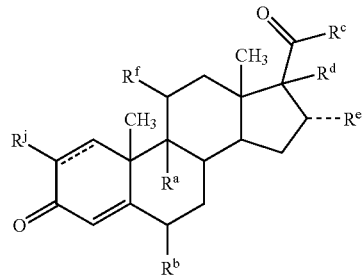

X wherein $R^a$ and $R^b$ independently represents, hydrogen or halogen;

$R^c$ is a valence-bond;

$R^d$ and $R^e$ independently represents: hydrogen, hydroxy, methyl or $C_1$-$C_4$-alkoxy or each are a group that forms a 1,3-dioxolane ring with the other;

$R^f$ is hydrogen, hydroxy, chloro, or forming a keto group with the carbon atom it is attached to;

$R^j$ is hydrogen or chloro; or a pharmaceutically acceptable salt or solvate thereof;

wherein

L is a linker molecule to which each of M and S are covalently linked.

60. The compound according to claim 59 wherein (i) Z is >N-$R_N$ and W is >$CH_2$;

(ii) U is H and Y is $CH_3$;

(iii) $R^1$ is an -O-$S^2$ group;

(iv) $S^1$ is a sugar moiety of Formula IIIa:

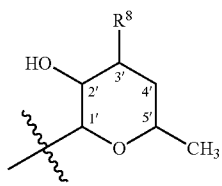

IIIa wherein $R^8$ is H or -N($CH_3$)$R^y$, wherein $R^y$ an alkyl;

$S^2$ sugar moiety of Formula IVa:

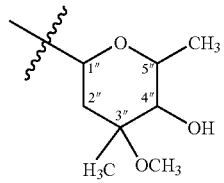

IVa (vi) $R^2$ is hydroxy;

(vii) A is $CH_3$;

(viii) B is $CH_3$;

(ix) E is H;

(x) $R^3$ is OH;

(xi) $R^4$ is $C_1$-$C_4$ alkyl;

(xii) $R^5$ is OH; and (xiii) $R^6$ is $C_1$-$C_4$-alkyl;

$R^d$ is H or OH;

$R^e$ is $CH_3$ ;

$R^f$ is OH; and $R^j$ is H;

or a pharmaceutically acceptable salt or solvate thereof.

* * * * *